(12) United States Patent
Stoessel et al.

(10) Patent No.: US 8,986,852 B2
(45) Date of Patent: Mar. 24, 2015

(54) BENZANTHRACENE DERIVATIVES FOR ORGANIC ELECTROLUMINESCENT DEVICES

(75) Inventors: Philipp Stoessel, Frankfurt am Main (DE); Arne Buesing, Frankfurt (DE); Holger Heil, Frankfurt am Main (DE)

(73) Assignee: Merck Patent GmbH (DE)

( * ) Notice: Subject to any disclaimer, the term of this patent is extended or adjusted under 35 U.S.C. 154(b) by 453 days.

(21) Appl. No.: 12/602,039

(22) PCT Filed: Apr. 29, 2008

(86) PCT No.: PCT/EP2008/003474
§ 371 (c)(1),
(2), (4) Date: Nov. 25, 2009

(87) PCT Pub. No.: WO2008/145239
PCT Pub. Date: Dec. 4, 2008

(65) Prior Publication Data
US 2010/0187505 A1      Jul. 29, 2010

(30) Foreign Application Priority Data
May 29, 2007   (DE) .................. 10 2007 024 850

(51) Int. Cl.
| | |
|---|---|
| *H01L 51/50* | (2006.01) |
| *C07C 211/54* | (2006.01) |
| *C07C 15/28* | (2006.01) |
| *C07C 15/62* | (2006.01) |
| *C07C 39/12* | (2006.01) |
| *C07C 211/61* | (2006.01) |
| *H05B 33/14* | (2006.01) |
| *C09B 57/00* | (2006.01) |
| *C09B 3/02* | (2006.01) |
| *C09B 3/12* | (2006.01) |
| *H01L 51/00* | (2006.01) |

(52) U.S. Cl.
CPC .............. *C07C 211/54* (2013.01); *C07C 15/28* (2013.01); *C07C 15/62* (2013.01); *C07C 39/12* (2013.01); *C07C 211/61* (2013.01); *C09K 2211/1011* (2013.01); *C09K 2211/1014* (2013.01); *C09K 2211/1029* (2013.01); *C09K 2211/1044* (2013.01); *C09K 2211/1059* (2013.01); *H01L 51/0052* (2013.01); *H01L 51/0054* (2013.01); *H01L 51/0058* (2013.01); *H01L 51/006* (2013.01); *H01L 51/0072* (2013.01); *H01L 51/5012* (2013.01); *H01L 51/5048* (2013.01); *H05B 33/14* (2013.01); *C09B 57/001* (2013.01); *C09B 57/008* (2013.01); *C09B 3/02* (2013.01); *C09B 3/12* (2013.01); *Y02E 10/549* (2013.01); *Y10S 428/927* (2013.01)
USPC .......... 428/690; 428/927; 313/504; 313/505; 313/506; 257/40; 257/E51.05; 257/E51.026; 257/E51.032; 546/18; 546/24; 546/79; 546/81; 546/101; 544/234

(58) Field of Classification Search
USPC ..................... 428/690, 917; 257/40, E51.05, 257/E51.026, E51.032; 313/504, 505, 506; 585/27; 546/18, 24, 79, 81, 101; 544/234
See application file for complete search history.

(56) References Cited

U.S. PATENT DOCUMENTS

| | | | |
|---|---|---|---|
| 5,858,563 | A | 1/1999 | Sano et al. |
| 6,203,933 | B1 | 3/2001 | Nakaya et al. |
| 2004/0076853 | A1 | 4/2004 | Jarikov |
| 2006/0216633 | A1 | 9/2006 | Kubota et al. |
| 2007/0202354 | A1 | 8/2007 | Funahashi |
| 2007/0273272 | A1* | 11/2007 | Kubota .................. 313/504 |
| 2008/0207864 | A1 | 8/2008 | Nakagawa et al. |
| 2009/0128010 | A1 | 5/2009 | Hyun et al. |

FOREIGN PATENT DOCUMENTS

| | | |
|---|---|---|
| EP | 0728828 A2 | 8/1996 |
| JP | 8231951 A | 9/1996 |
| JP | 8311442 A | 11/1996 |
| JP | 2000178548 A | 6/2000 |
| JP | 2004-043349 A | 2/2004 |
| JP | 2005302667 A1 | 10/2005 |
| KR | 20070021043 A1 | 2/2007 |
| WO | WO-2005/090365 A1 | 9/2005 |
| WO | WO-2006085434 A1 | 8/2006 |

OTHER PUBLICATIONS

Own et al., Synthesis and rat liver microsomal metabolism of 2-chlorodibenzo[a,1] pyrene and 10-chlorodibenzo[a,1] pyrene, 1996, Polycyclic Aromatic Compounds, vol. 11 (1-4) Abstract.*
Clar, E., et al., "Asymmetric annellation Effects—VI," *Tetrahedron*, 1962, vol. 18, pp. 1471-1475.
Smith, Jr., W.M., et al., "Isocyanates of 9-Methyl- and 9,10-Dimethyl-1,2-benzanthracene," *Journal of the American Chemical Society*, Jan. 1, 1951, vol. 73, No. 1, pp. 319-322.

* cited by examiner

*Primary Examiner* — Gregory Clark
(74) *Attorney, Agent, or Firm* — Drinker Biddle & Reath LLP

(57) ABSTRACT

The present invention relates to the compounds of the formula (1) and to organic electroluminescent devices, in particular blue-emitting devices, in which these compounds are used as host material or dopant in the emitting layer and/or as hole-transport material and/or as electron-transport material.

17 Claims, No Drawings

BENZANTHRACENE DERIVATIVES FOR ORGANIC ELECTROLUMINESCENT DEVICES

CROSS-REFERENCE TO RELATED APPLICATIONS

This application is a national stage application (under 35 U.S.C. §371) of PCT/EP2008/003474, filed Apr. 29, 2008, which claims benefit of German application 10 2007 024 850.6, filed May 29, 2007.

BACKGROUND OF THE INVENTION

The present invention relates to organic semiconductors and to the use thereof in organic electronic devices.

Organic semiconductors are being developed for a number of electronic applications of different types. The structure of organic electroluminescent devices (OLEDs) in which these organic semiconductors are employed as function al materials is described, for example, in U.S. Pat. No. 4,539,507, U.S. Pat. No. 5,151,629, EP 0676461 and WO 98/27136. However, further improvements are still necessary before these devices can be used for high-quality and long-lived displays. Thus, in particular, the inadequate lifetime and the inadequate efficiency of blue-emitting organic electroluminescent devices currently still represent a problem which has not yet been satisfactorily solved. Furthermore, it is necessary for the compounds to have high thermal stability and a high glass-transition temperature and to be sublimable without decomposition. In particular for use at elevated temperature, a high glass-transition temperature is essential in order to achieve long lifetimes.

For fluorescent OLEDs, principally condensed aromatic compounds, in particular anthracene derivatives, are used in accordance with the prior art as host materials, especially for blue-emitting electroluminescent devices, for example 9,10-bis(2-naphthyl)anthracene (U.S. Pat. No. 5,935,721). WO 03/095445 and CN 1362464 disclose 9,10-bis(1-naphthyl) anthracene derivatives for use in OLEDs. Further anthracene derivatives are disclosed in WO 01/076323, in WO 01/021729, in WO 04/013073, in WO 04/018588, in WO 03/087023 or in WO 04/018587. Host materials based on aryl-substituted pyrenes and chrysenes are disclosed in WO 04/016575. For high-quality applications, it is necessary to have improved host materials available.

Prior art which may be mentioned in the case of blue-emitting compounds is the use of arylvinylamines (for example WO 04/013073, WO 04/016575, WO 04/018587). However, these compounds are thermally unstable and cannot be evaporated without decomposition, which requires high technical complexity for OLED production and thus represents a technical disadvantage. It is therefore necessary for high-quality applications to have improved emitters available, particularly with respect to device and sublimation stability and emission colour.

There thus continues to be a demand for improved materials, in particular host materials for fluorescent emitters, especially for blue-fluorescent emitters, and fluorescent materials which are thermally stable, result in good efficiencies and at the same time in long lifetimes in organic electronic devices, give reproducible results during the production and operation of the device and are readily accessible synthetically. Further improvements are also necessary in the case of hole- and electron-transport materials.

Surprisingly, it has been found that benz[a]anthracene derivatives which are substituted in at least one of positions 2, 3, 4, 5 or 6 by an aromatic or heteroaromatic group, by a diarylamino group or by one of the other groups defined below are very highly suitable for use in organic electroluminescent devices. These compounds enable an increase in the efficiency and especially the lifetime of the organic electronic device compared with materials in accordance with the prior art. This applies, in particular, to blue-fluorescent devices. Furthermore, these compounds have high thermal stability. In general, these materials are very highly suitable for use in organic electronic devices since they have a high glass-transition temperature. The present invention therefore relates to these materials and to the use thereof in organic electronic devices.

Benz[a]anthracene derivatives which are substituted in these positions by aromatic substituents have already been described sporadically in the literature (for example K. Maruyama et al., *Chem. Lett.* 1975, (1), 87-88; C. L. L. Chai et al., *Austr, J. Chem.* 1995, 48(3), 577-591, M. C. Kloetzel of al., *J. Org. Chem.* 1961, 26, 1748-1754 etc.). However, only the synthesis and reactivity of these compounds have been investigated. The use of these compounds in organic electronic devices has not been proposed. Furthermore, WO 05/090365 has disclosed a multiplicity of organosilane compounds containing polycyclic aromatic groups, inter alia also for use in organic electroluminescent devices, also including, besides numerous other compounds, a compound which is an aryl-substituted benzanthracene. The particular effect of these compounds is attributed here to the presence of the organosilyl group and not to the substituted benzanthracene skeleton.

For reasons of clarity, the structure and numbering of benz [a]anthracene are shown below:

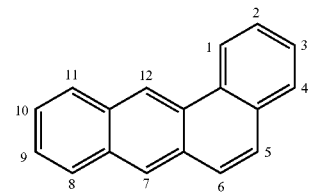 [SMILES: c1ccc2cc3c(ccc4ccccc43)cc2c1]

BRIEF SUMMARY OF THE INVENTION

The invention relates to uncharged compounds of the formula (1)

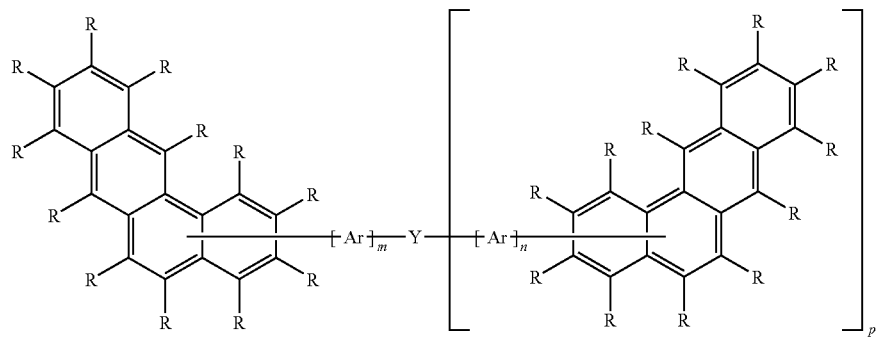

Formula (1)

where the group Ar or Y is bonded via one of positions 2, 3, 4, 5 or 6 of the benz[a]anthracene and correspondingly no radical R is bonded at this position and where the following applies to the symbols and indices:

Ar is on each occurrence, identically or differently, a divalent aromatic or heteroaromatic ring system having 5 to 40 aromatic ring atoms, which may be substituted by one or more radicals R;

Y is, depending on the index p, a mono-, di-, tri-, tetra-, penta- or hexavalent aromatic or heteroaromatic ring system having 5 to 40 aromatic ring atoms, which may be substituted by one or more radicals R; or Y is, if p=0, an $N(Ar^1)_2$, $C(=O)Ar^1$ or $P(=O)(Ar^1)_2$ group; or Y is, if p=1, a single bond or C=O, O, S, SO, $SO_2$, $NR^1$, $NAr^1$, $PAr^1$, $P(=O)$ $Ar^1$, $P(=S)Ar^1$, $O-B(Ar^1)-O$, $O-BR^1-O$, $BAr^1$, $-CR^1=CR^1-$, $-C\equiv C-$, an alkylene or alkylidene group having 1 to 20 C atoms, each of which may also be substituted by one or more radicals $R^1$, where one or more non-adjacent $CH_2$ groups may be replaced by $R^1C=CR^1$, $C\equiv C$, $Si(R^1)_2$, $Ge(R^1)_2$, $Sn(R^1)_2$, C=O, C=S, C=Se, $C=NR^1$, $P(=O)(R^1)$, SO, $SO_2$, $NR^1$, O, S or $CONR^1$ and where one or more H atoms may be replaced by F, Cl, Br, I, CN or $NO_2$; or Y is, if p=2, equal to B, $B_3O_3$, $CR^1$, $CAr^1$, N, P, P=O or P=S;

R is, identically or differently on each occurrence, H, D, F, Cl, Br, I, CHO, $N(Ar^1)_2$, $N(R^2)_2$, $C(=O)Ar^1$, $P(Ar^1)_2$, $P(=O)$ $(Ar^1)_2$, $S(=O)Ar^1$, $S(=O)_2Ar^1$, $CR^1=CR^1Ar^1$, CN, $NO_2$, $Si(R^1)_3$, $B(OAr^1)_2$, $B(OR^1)_2$, $OSO_2R^1$, OH, a straight-chain alkyl or thioalkoxy group having 1 to 40 C atoms or a straight-chain alkoxy group having 2 to 40 C atoms or a branched or cyclic alkyl, alkoxy or thioalkoxy group having 3 to 40 C atoms, each of which may be substituted by one or more radicals $R^1$, where one or more non-adjacent $CH_2$ groups may be replaced by $R^1C=CR^1$, C=O, $Si(R^1)_2$, $Ge(R^1)_2$, $Sn(R^1)_2$, C=O, C=S, C=Se, $C=NR^1$, $P(=O)(R^1)$, SO, $SO_2$, $NR^1$, O, S or $CONR^1$ and where one or more H atoms may be replaced by D, F, Cl, Br, I, CN or $NO_2$, or an aromatic or heteroaromatic ring system having 5 to 60 aromatic ring atoms, which may be substituted by one or more non-aromatic radicals R, or an aryloxy or heteroaryloxy group having 5 to 60 aromatic ring atoms, which may be substituted by one or more non-aro matic radicals R, or a combination of these systems; two or more adjacent substituents R here may also form a mono- or polycyclic aliphatic ring system with one another;

$Ar^1$ is on each occurrence, identically or differently, an aromatic or heteroaromatic ring system having 5 to 30 aromatic ring atoms, which may be substituted by one or more non-aromatic radicals R; two radicals $Ar^1$ which are bonded to the same nitrogen or phosphorus atom may also be linked to one another here by a single bond or by a bridge selected from $B(R^1)$, $C(R^1)_2$, $Si(R^1)_2$, C=O, $C=NR^1$, $C=C(R^1)_2$, O, S, S=O, $SO_2$, N(R), $P(R^1)$ and $P(=O)R^1$;

$R^1$ is on each occurrence, identically or differently, H or an aliphatic, aromatic and/or heteroaromatic hydrocarbon radical having 1 to 20 C atoms, in which, in addition, one or more H atoms may be replaced by F; two or more adjacent substituents $R^1$ here may also form a mono- or polycyclic aliphatic or aromatic ring system with one another;

m, n are on each occurrence, identically or differently, 0, 1, 2 or 3;

p is 0, 1, 2, 3, 4 or 5;

the following compounds are excluded from the invention:

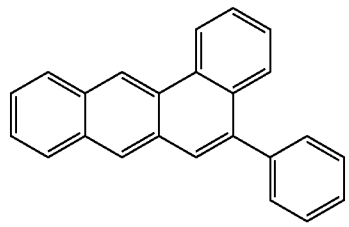

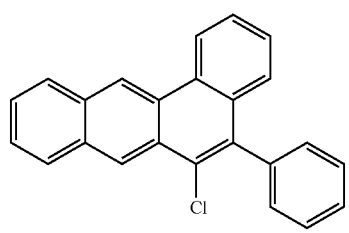

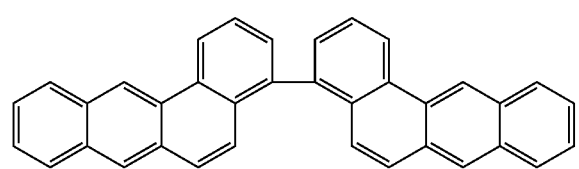

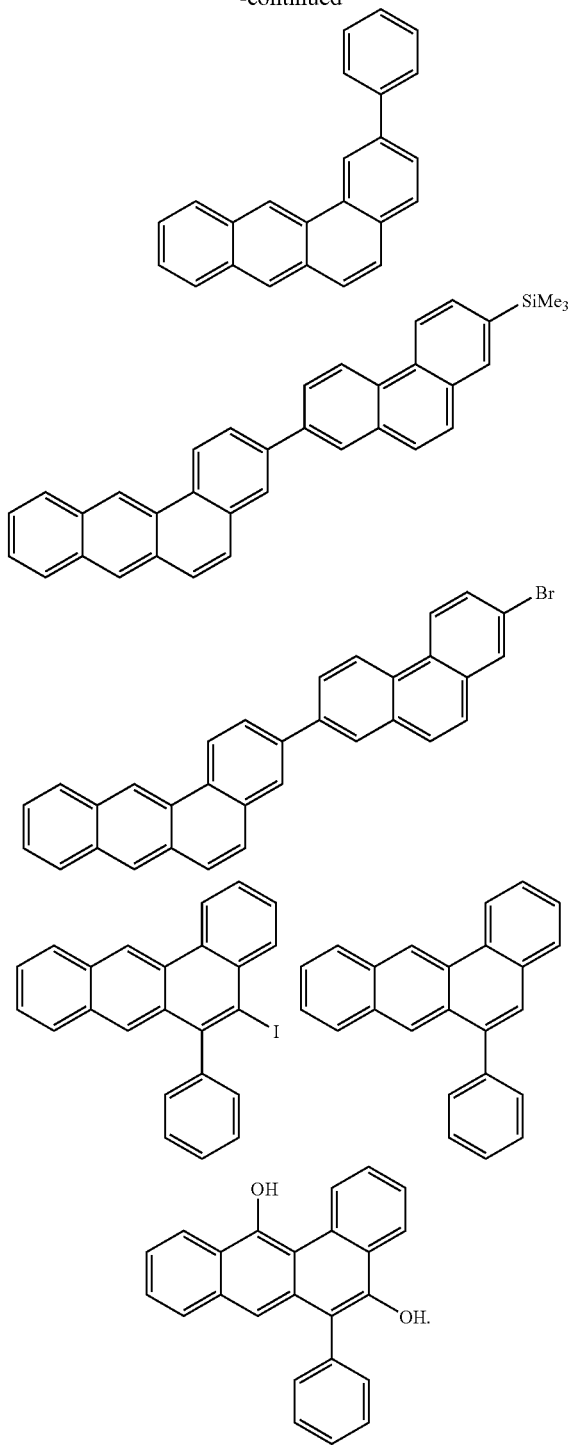

DETAILED DESCRIPTION OF THE INVENTION

The compounds of the formula (1) preferably have a glass-transition temperature $T_g$ of greater than 70° C., particularly preferably greater than 100° C., very particularly preferably greater than 130° C.

For the purposes of this invention, an aryl group contains 6 to 60 C atoms; for the purposes of this invention, a heteroaryl group contains 2 to 60 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed aryl or heteroaryl group, for example naphthalene, anthracene, pyrene, quinoline, isoquinoline, benzimidazole, phenanthrene, etc.

For the purposes of this invention, an aromatic ring system contains 6 to 40 C atoms in the ring system. For the purposes of this invention, a heteroaromatic ring system contains 2 to 40 C atoms and at least one heteroatom in the ring system, with the proviso that the sum of C atoms and heteroatoms is at least 5. The heteroatoms are preferably selected from N, O and/or S. For the purposes of this invention, an aromatic or heteroaromatic ring system is intended to be taken to mean a system which does not necessarily contain only aryl or heteroaryl groups, but instead in which a plurality of aryl or heteroaryl groups may also be interrupted by a short non-aromatic unit (preferably less than 10% of the atoms other than H), such as, for example, an $sp^3$-hybridised C, N or O atom. Thus, for example, systems such as 9,9'-spirobifluorene, 9,9-diarylfluorene, triarylamine, diaryl ether, stilbene, benzophenone, etc., are also intended to be taken to mean aromatic ring systems for the purposes of this invention. Likewise, an aromatic or heteroaromatic ring system is taken to mean systems in which a plurality of aryl or heteroaryl groups are linked to one another by single bonds, for example biphenyl, terphenyl or bipyridine.

For the purposes of the present invention, a $C_1$- to $C_{40}$-alkyl group, in which, in addition, individual H atoms or $CH_2$ groups may be substituted by the above-mentioned groups, is particularly preferably taken to mean the radicals methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. A $C_1$- to $C_{40}$-alkoxy group is particularly preferably taken to mean methoxy, trifluoromethoxy, ethoxy, n-propoxy, i-propoxy, n-butoxy, i-butoxy, s-butoxy, t-butoxy or 2-methylbutoxy. An aromatic or heteroaromatic ring system having 5-40 aromatic ring atoms, which may in each case also be substituted by the above-mentioned radicals R and which may be linked via any desired positions on the aromatic or heteroaromatic ring system, is taken to mean, in particular, groups derived from benzene, naphthalene, anthracene, phenanthrene, pyrene, chrysene, perylene, fluoranthene, naphthacene, pentacene, benzanthracene, dibenzanthracene, benzopyrene, biphenyl, biphenylene, terphenyl, terphenylene, fluorene, spirobifluorene, dihydrophenanthrene, dihydropyrene, tetrahydropyrene, cis- or transindenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthroimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6- diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

A preferred embodiment of the present invention relates to compounds of the formula (2)

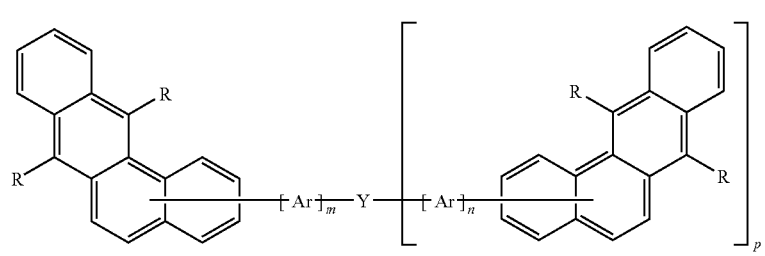

Formula (2)

where the group Ar or Y is bonded via one of positions 2, 3, 4, 5 or 6 of the benz[a]anthracene and where the symbols and indices have the same meaning as described above. If only one of the two substituents R on a benz[a]anthracene in formula (2) is not equal to hydrogen, this is preferably the substituent in the 7-position of the benz[a]anthracene.

As described above, the group Ar or Y is bonded to the benz[a]anthracene via position 2, 3, 4, 5 or 6. If the compound of the formula (1) or (2) contains a plurality of benz[a]anthracene units, i.e. if the index p is 1 or greater, each of these units may be bonded via the same position of the benz[a]anthracene or via different positions of the benz[a]anthracene. A bond via the same position of the benz[a]anthracene has the advantage that the compounds are more readily accessible synthetically. A bond via different positions of the benz[a]anthracene results in asymmetrical compounds, which generally have the advantage that they are more soluble and have a higher glass-transition temperature.

In a preferred embodiment of the invention, the group Ar or Y in formula (1) or formula (2) is bonded via position 2 or 3 of the benz[a]anthracene, meaning that the benz[a]anthracene has no substituents or protons in the peri-position to Ar or Y. In these cases, formation of atropisomers about the benz[a]anthracene-Ar or benz[a]anthracene-Y bond is not possible, even in the case of bulky groups Ar or Y, such as, for example, anthracone.

In a further preferred embodiment of the invention, the group Ar or Y in formula (1) or formula (2) is bonded via position 4, 5 or 6 of the benz[a]-anthracene, meaning that the benz[a]anthracene has either a substituent or a proton in the peri-position to Ar or Y. In these cases, the formation of atropisomers about the benz[a]anthracene-Ar or benz[a]anthracene-Y bond is possible in the case of bulky groups Ar or V, such as, for example, anthracene.

For the purposes of this invention, the peri-position on the benz[a]anthracene is intended to be defined analogously to naphthalene.

Particularly preferred embodiments of the structures of the formula (1) are the structures of the formulae (3) to (24):

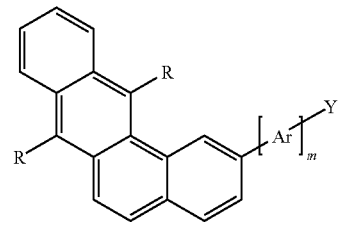

Formula (3)

-continued

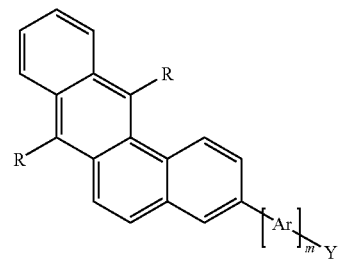

Formula (4)

Formula (5)

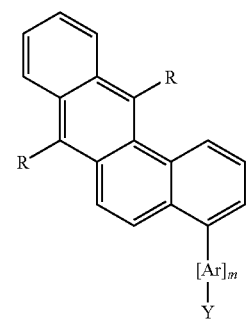

Formula (6)

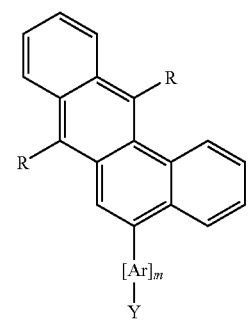

-continued
Formula (7)
Formula (8)
Formula (9)
Formula (10)
Formula (11)
Formula (12)
-continued
Formula (13)
Formula (14)
Formula (15)
Formula (16)
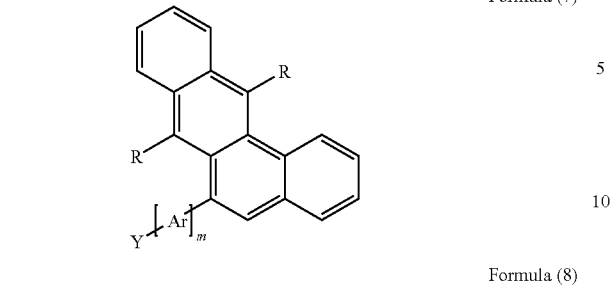
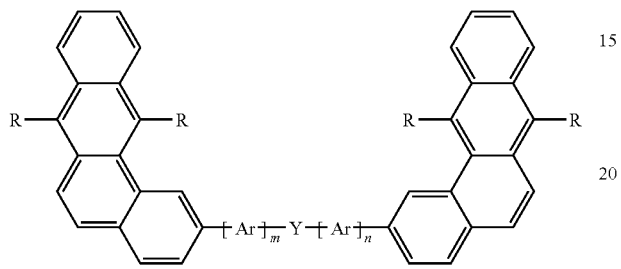
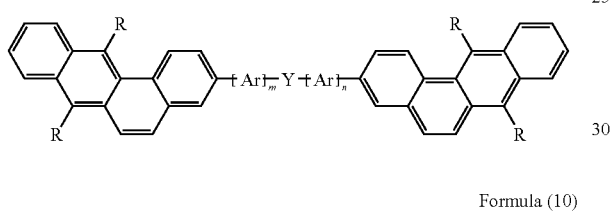
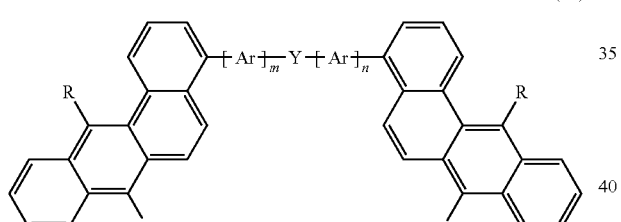

Formula (17)

Formula (18)

Formula (19)

Formula (20)

Formula (21)

Formula (22)

Formula (23)

Formula (24)

where the symbols and indices have the same meaning as described above, where the benz[a]anthracene skeleton may also carry deuterium instead of hydrogen and where the group Y in formulae (3) to (7) stands for a monovalent aromatic or heteroaromatic ring system or an $N(Ar^1)_2$ group.

In the structures of the formulae (3) to (24), the substituent R in the 12-position is preferably hydrogen or deuterium, in particular hydrogen. It is particularly preferred for both substituents R, i.e. the substituents in the 7- and 12-positions, to be hydrogen or deuterium, in particular hydrogen.

Preference is furthermore given to compounds of the formula (1) or of the formulae (3) to (7) in which the symbol Y stands for a purely aromatic or heteroaromatic system which contains no non-aromatic groups and which may be condensed or uncondensed or for an aromatic amino group. The group Y is particularly preferably built up from the aryl or heteroaryl groups benzene, naphthalene, anthracene, carbazole, phenanthrene, benzanthracene, chrysene, pyrene, phenanthroline, 1,3,5-triazine, benzimidazole and phenanthroimidazole or, if p=0, represents an $N(Ar^1)_2$ group. Very particularly preferred groups Y for p=0 or for compounds of the formulae (3) to (7) are the groups of the following formulae (25) to (33):

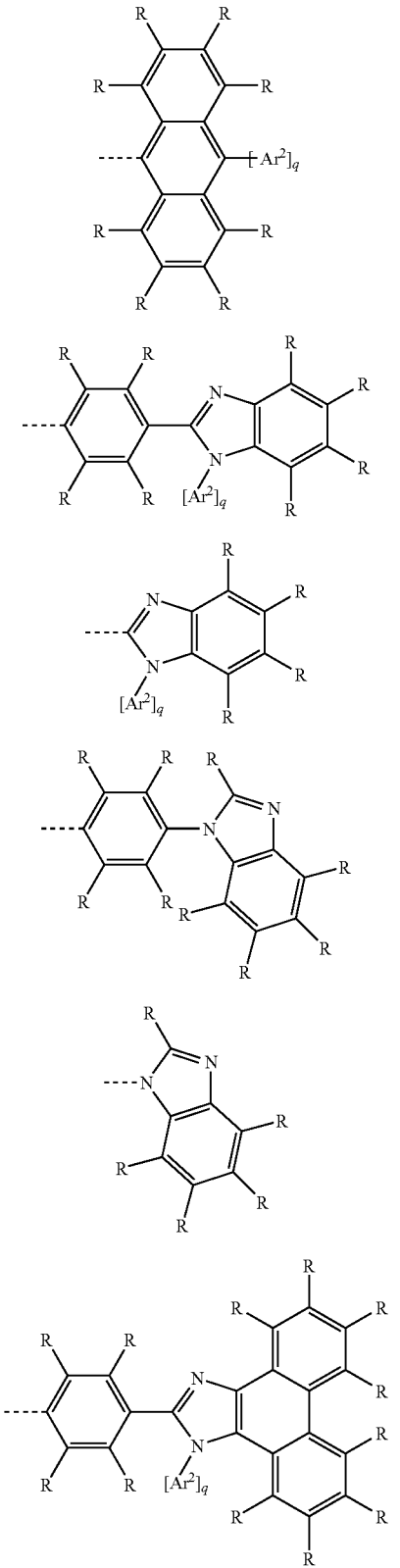

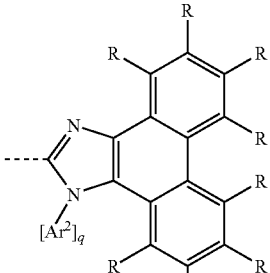

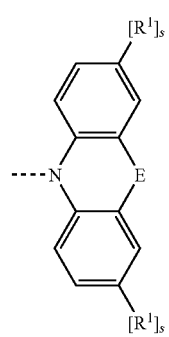

where R and R¹ have the meaning indicated above and furthermore:

Ar² is an aryl or heteroaryl group having 5 to 16 aromatic ring atoms, preferably phenyl, 1-naphthyl, 2-naphthyl, 9-anthryl, chrysenyl, 1-pyrenyl, 2-pyrenyl, 2-phenanthrenyl, 3-phenanthrenyl, 9-phenanthrenyl, 2-benzimidazole or fluoranthenyl, each of which may be substituted by one or more radicals R¹, or in formula (25) a group of the formula (32) or (33);

Ar³ is, identically or differently on each occurrence, an aryl or heteroaryl group having 5 to 20 aromatic ring atoms or a triarylamine group having 15 to 30 aromatic ring atoms, each of which may be substituted by one or more radicals R¹, preferably an aryl or heteroaryl group having 6 to 14 aromatic ring atoms or a triarylamine group having 18 to 30 aromatic ring atoms, preferably having 18 to 22 aromatic ring atoms, each of which may be substituted by one or more radicals R¹;

E stands for a single bond, O, S, N(R¹) or C(R¹)₂, where the two radicals R¹ may also form a spiro system through ring formation;

q is 1, 2 or 3;

s is on each occurrence, identically or differently, 0 or 1.

Particularly preferred systems for q=2 are ortho-biphenyl, meta-biphenyl, para-biphenyl, phenylene-1-naphthyl, phenylene-2-naphthyl, N-phenyl-2-benzimidazole, 2-fluorenyl and 2-spirobifluorenyl.

Ar³ in formula (33) particularly preferably stands, identically or differently, for phenyl, 1-naphthyl, 2-naphthyl, 2-, 3- or 4-triphenylamine, 1- or 2-naphthyldiphenylamine, each of which may be bonded via the naphthyl or the phenyl group, or 1- or 2-dinaphthylphenylamine, each of which may be bonded via the naphthyl or the phenyl group. These groups may each be substituted by one or more alkyl groups having 1 to 4 C atoms or by one or more cyclic or bicyclic alkyl groups having 3 to 8 C atoms or by fluorine.

Preference is furthermore given to compounds of the formulae (1) to (24) in which the symbol Ar, identically or differently on each occurrence, stands for a divalent aromatic or heteroaromatic ring system selected from 1,2-phenylene, 1,3-phenylene, 1,4-phenylene, 1,4-naphthylene, 9,10-anthrylene, 2,7-phenanthrenylene, 3,6-phenanthrenylene, 1,6-pyrenylene, 2,7-pyrenylene, 2,6-pyridinylene, 2,5-pyridinylene, 2,2'-biphenyl, 3,3'-biphenyl, 4,4'-biphenyl, 2,7-fluorenyl and 2,7-spirobifluorenyl. It should expressly be emphasised at this point that the Ar groups in formula (1) or in formula (2) or in formulae (8) to (24) can be selected to be identical or different.

Preference is furthermore given to compounds of the formula (1) and formula (2) where p=1 and of the formulae (8) to (12) and (15) to (24) in which the symbol Y stands for a single bond or for a divalent group selected from C=O, O, NAr$^2$, POAr$^2$, O—B(Ar$^2$)—O, a divalent alkylene or alkylidene group having 1 to 6 C atoms or a divalent aromatic or heteroaromatic ring system having 5 to 14 aromatic ring atoms. Preference is furthermore given to compounds of the formula (1) and formula (2) where p=2 and of the formula (13) or (14) in which the symbol Y stands for N or a trivalent aromatic or heteroaromatic ring system having 5 to 14 aromatic ring atoms, in particular for 1,3,6-benzene or 1,3,5-triazine. In compounds of the formula (1) and formula (2) where p>2, Y preferably stands for a correspondingly polyvalent aromatic or heteroaromatic ring system having 5 to 14 aromatic ring atoms.

In the compounds of the formula (1) or (2) or of the formulae (8) to (24), all indices m and n can be selected to be identical, which results in symmetrical compounds, or they can be selected to be different, which results in asymmetrical compounds. As already mentioned above, symmetrical compounds have the advantage of easier synthetic accessibility and asymmetrical compounds have the advantage of more suitable physical properties.

Preference is furthermore given to compounds of the formula (1) or (2) or of the formulae (3) to (24) in which the indices m and n stand for 0 or 1.

Preference is furthermore given to compounds of the formula (1) or (2) or of the formulae (3) to (24) in which the index p stands for 0, 1 or 2, particularly preferably for 0 or 1.

If a radical R stands for an N(Ar$^1$)$_2$ group, this group is preferably selected from the groups of the formula (32) or of the formula (33) depicted above.

Examples of preferred compounds of the formula (1) are structures (1) to (338) depicted below.

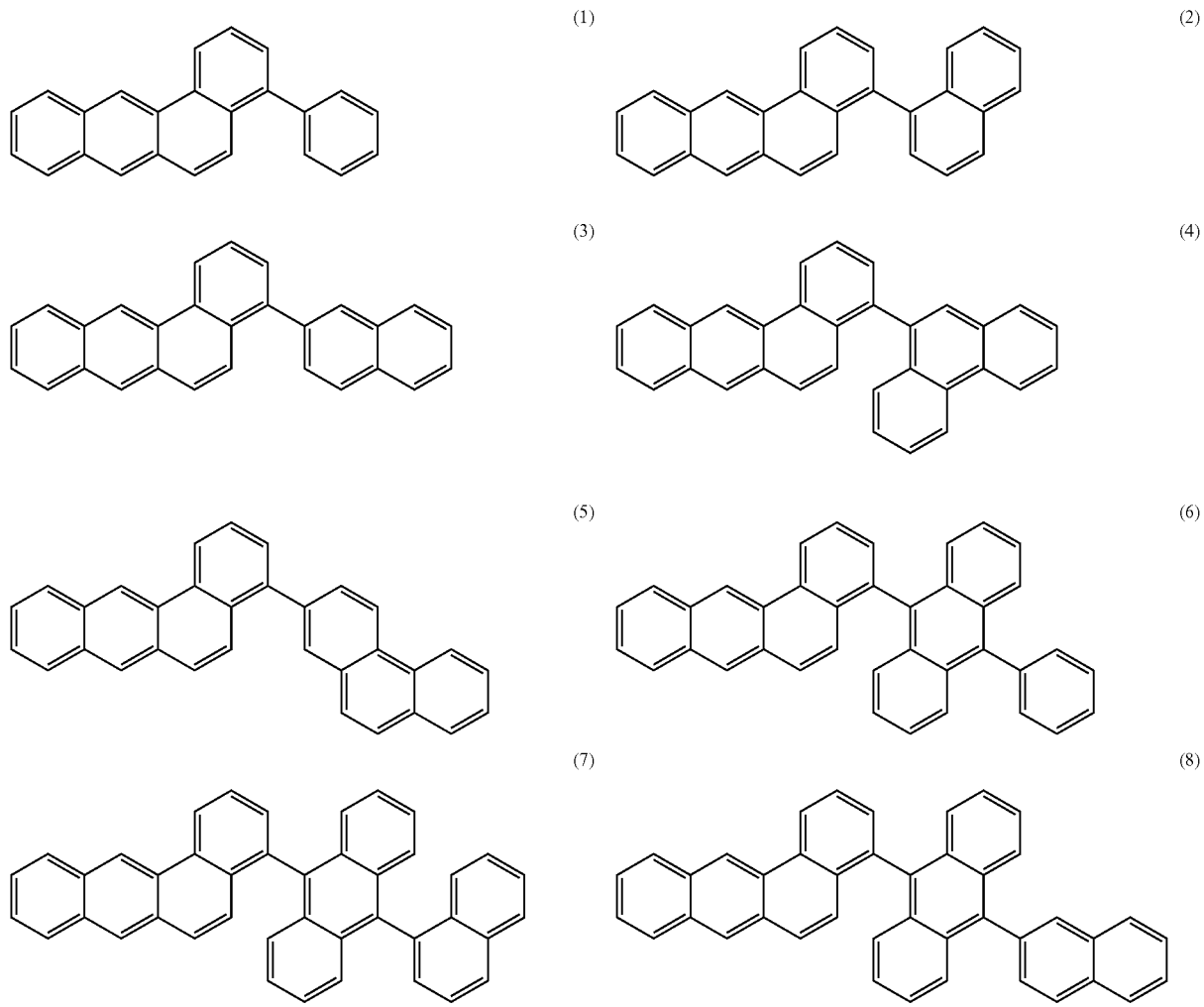

(9)
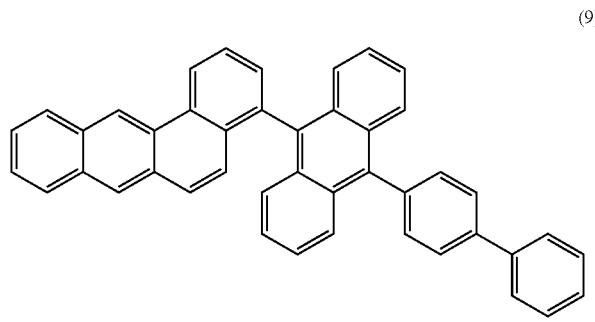
(10)
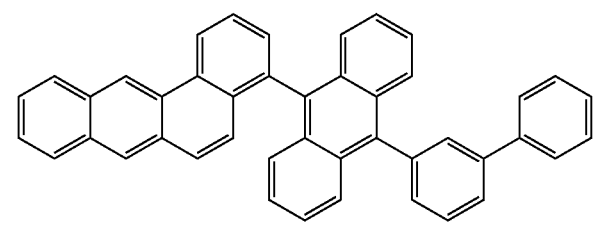
(11)
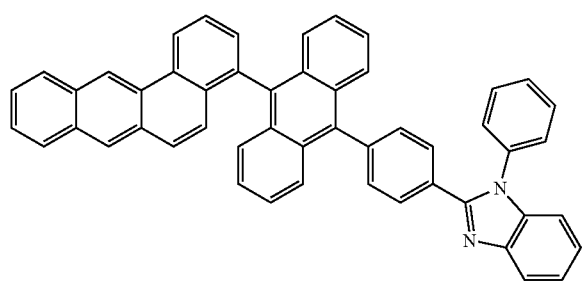
(12)
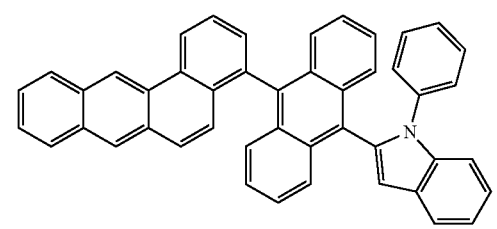
(13)
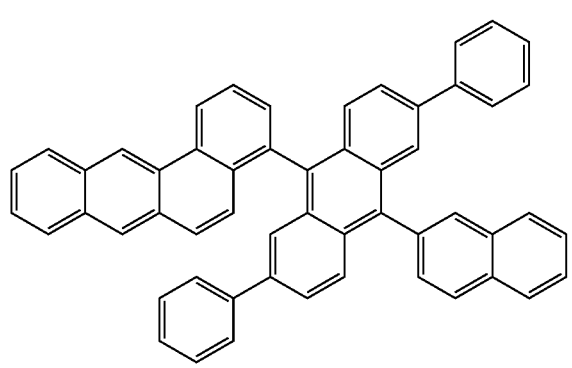
(14)
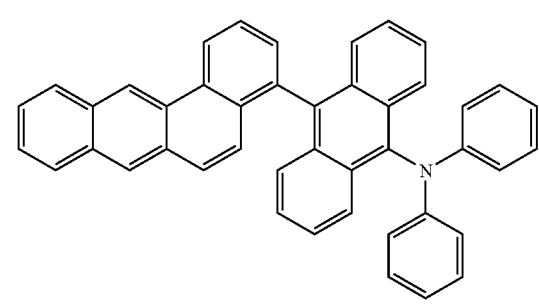
(15)
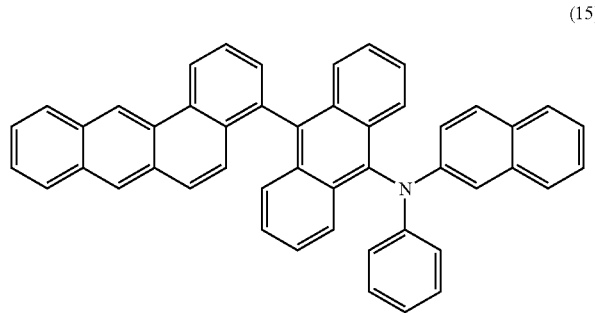
(16)
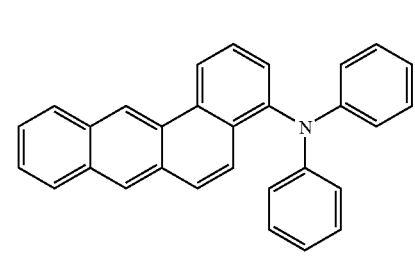

(17)
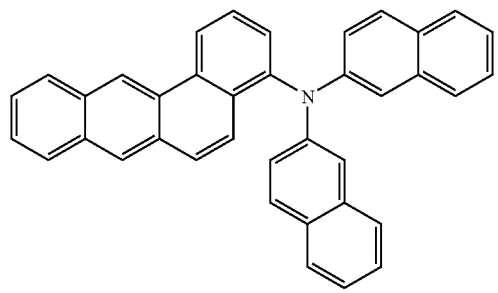
(18)
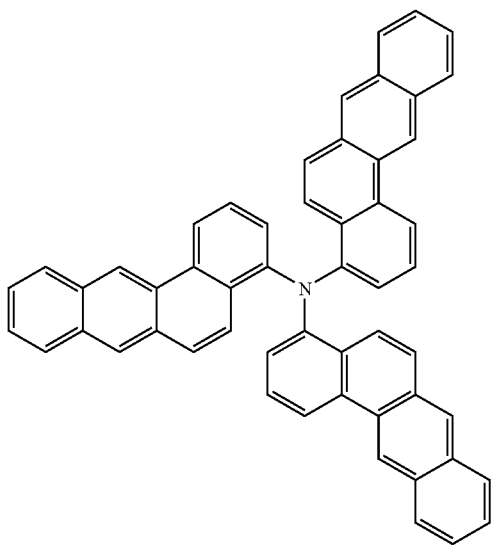
(19)
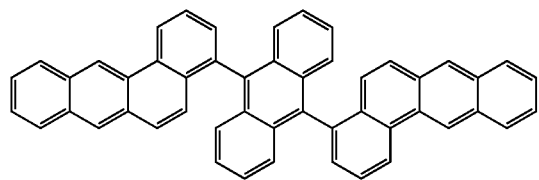
(20)
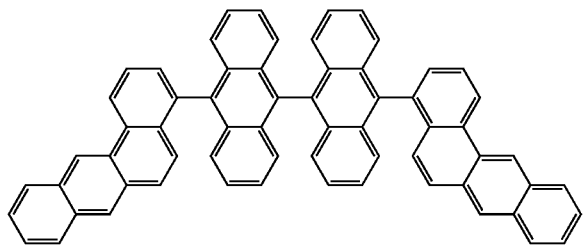
(21)
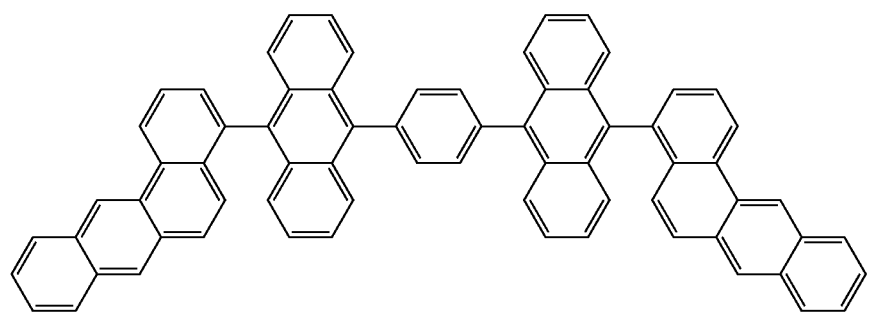

(22)
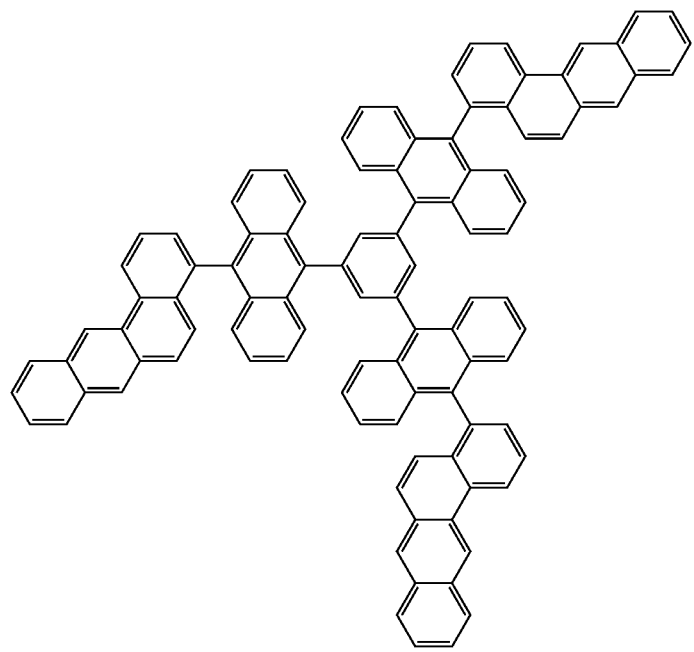
(23)
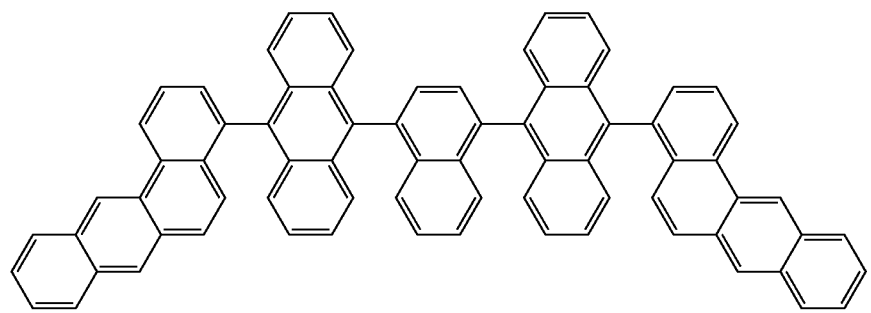
(24)
(25)
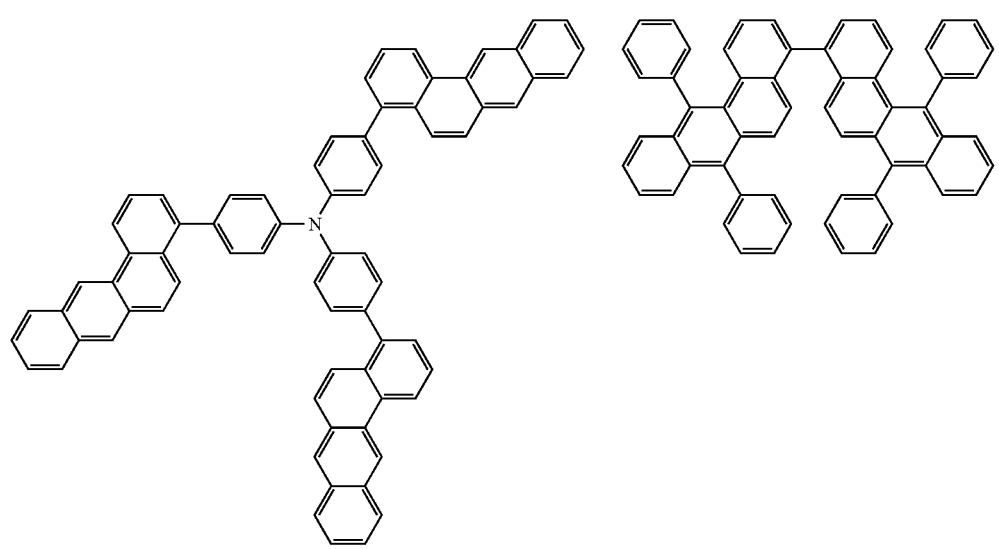

(26)
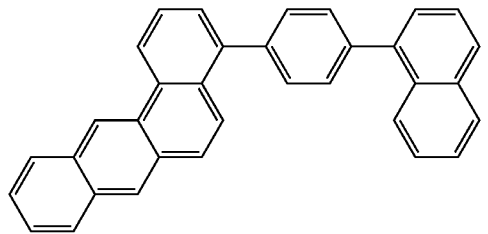
(27)
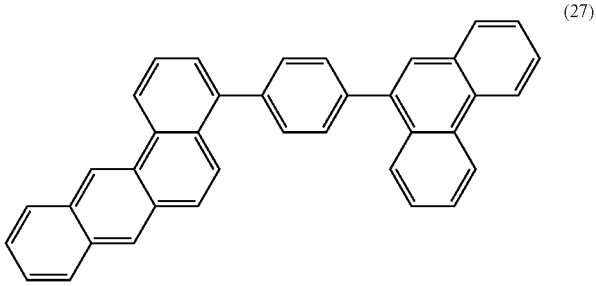
(28)
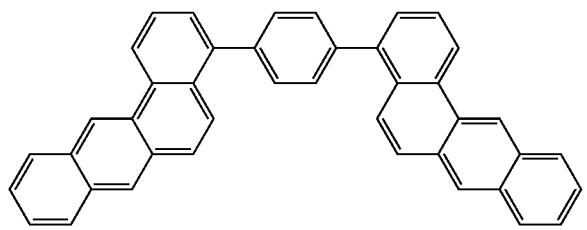
(29)
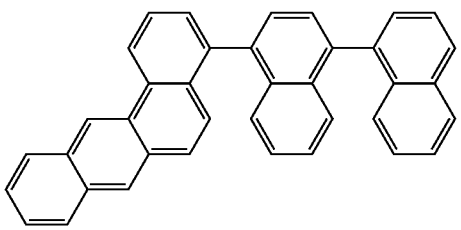
(30)
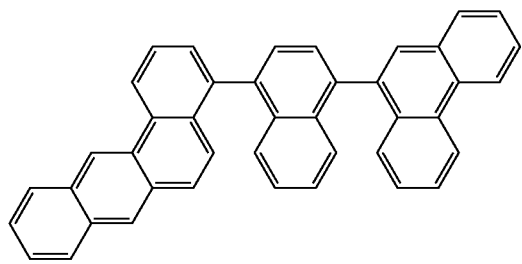
(31)
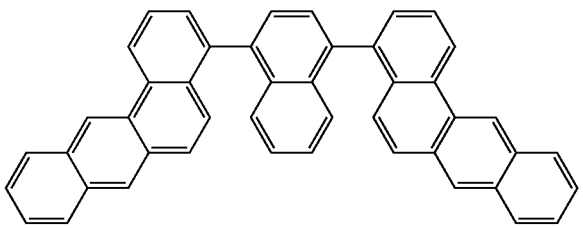
(32)
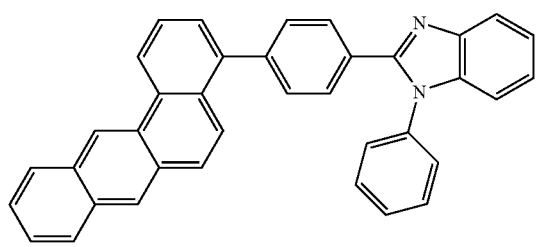
(33)
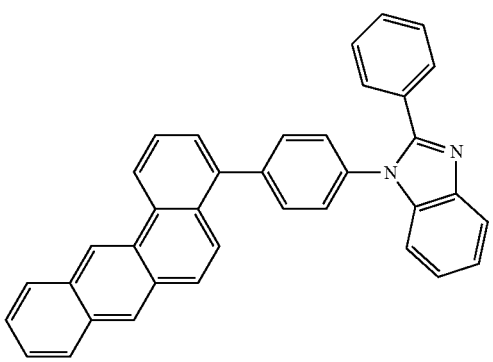

(34)
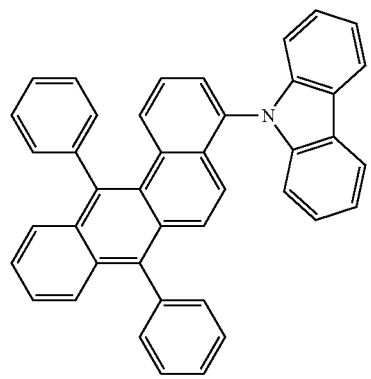
(35)
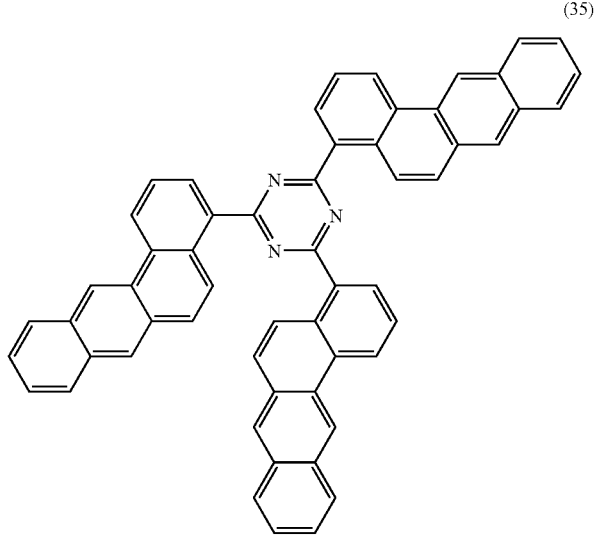
(36)
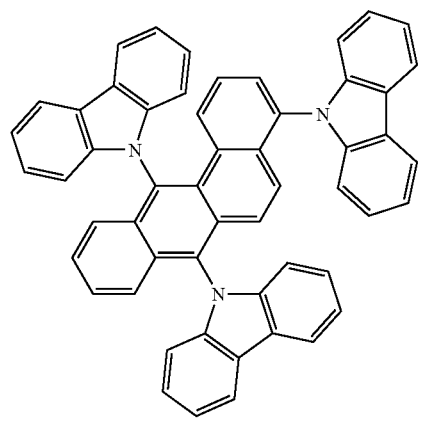
(37)
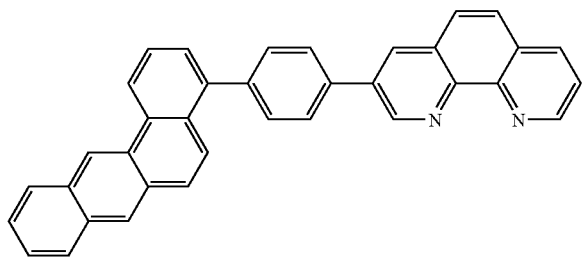
(38)
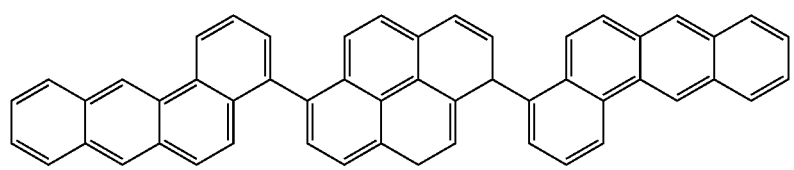
(39)
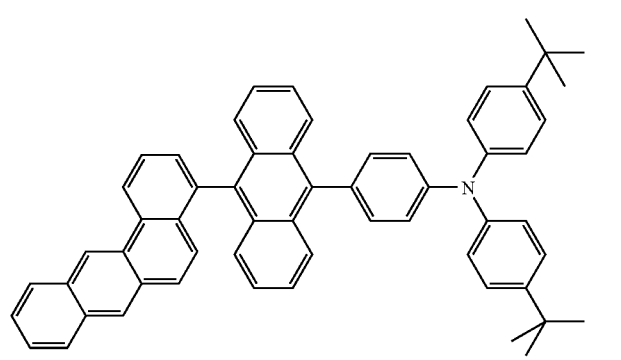
(40)
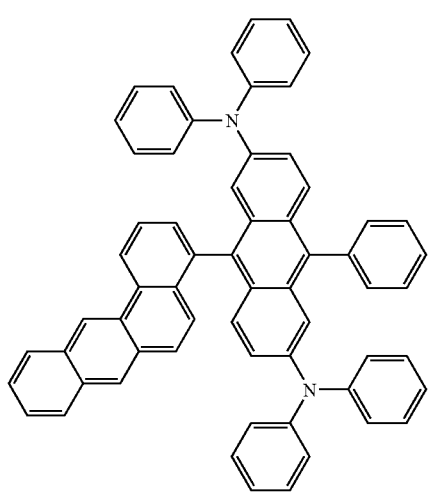

(41)
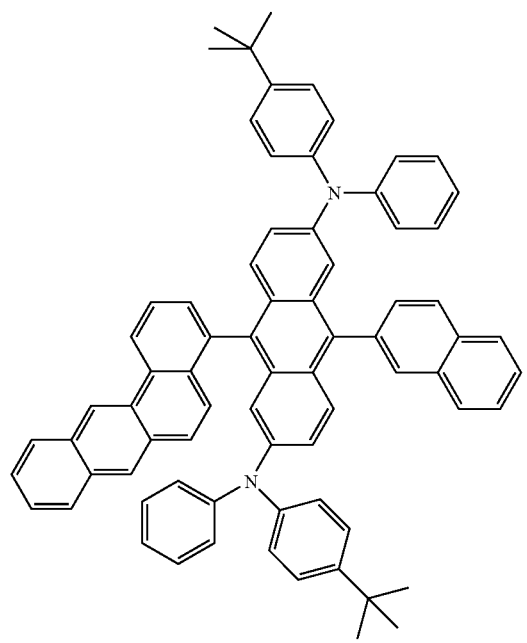
(42)
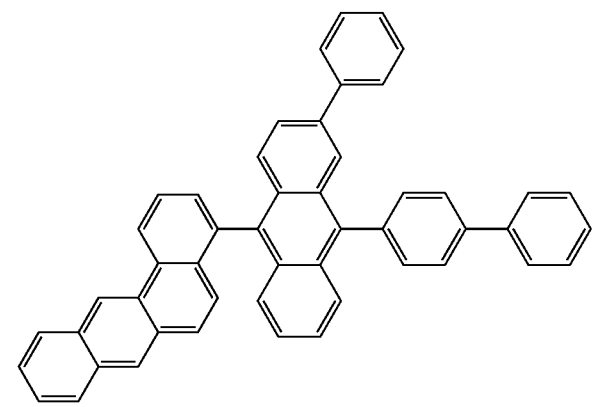
(43)
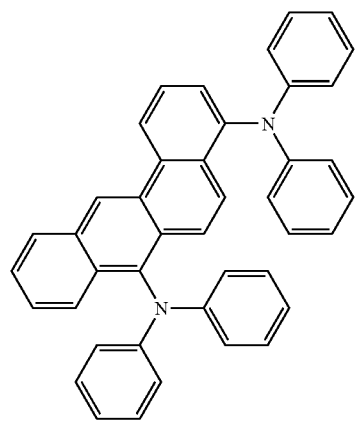
(44)
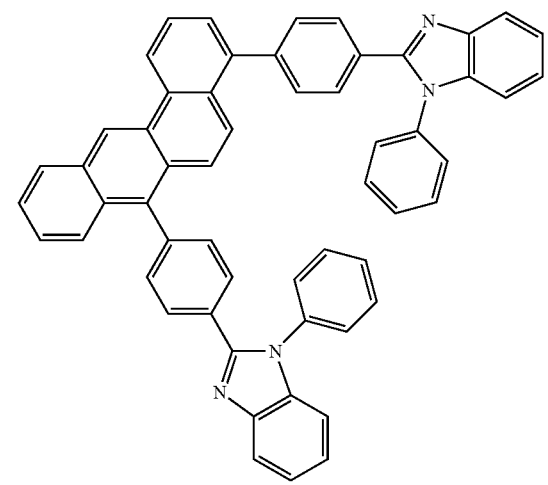
(45)
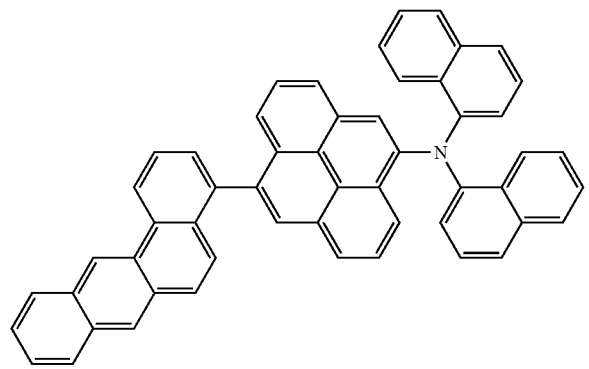
(46)
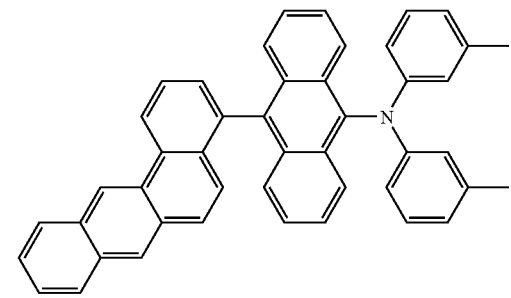

-continued
(47)
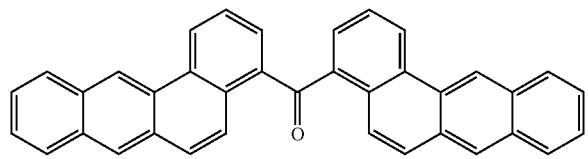
(48)
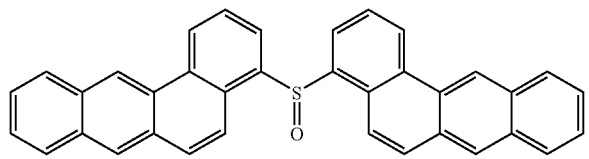
(49)
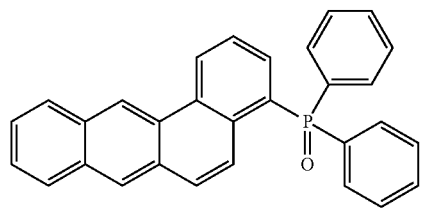
(51)
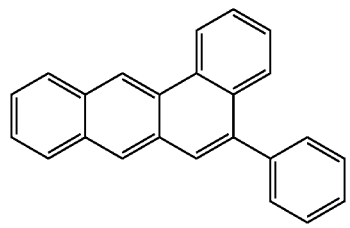
(52)
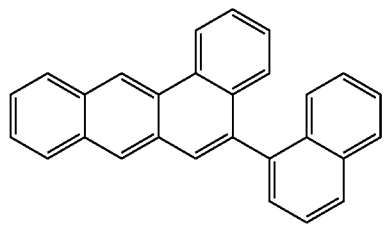
(53)
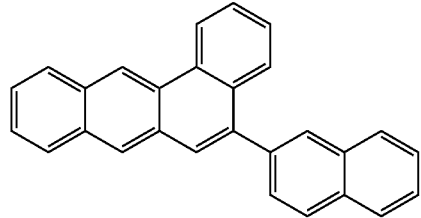
(54)
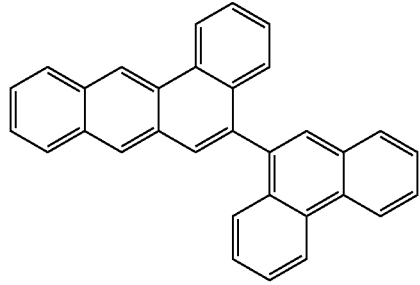
(55)
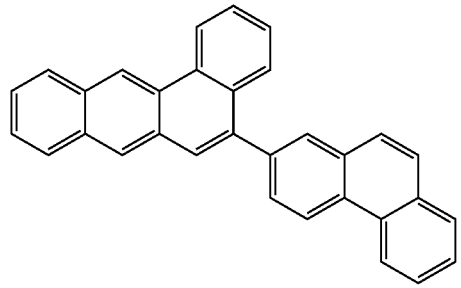
(56)
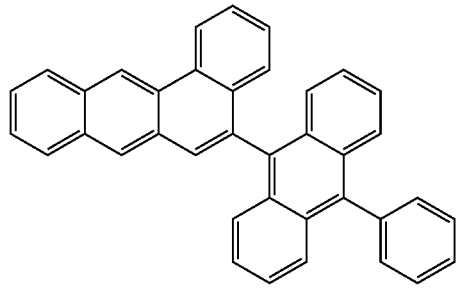
(57)
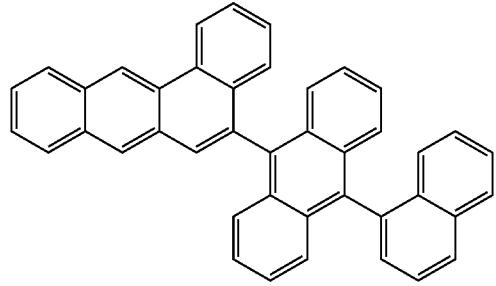
(58)
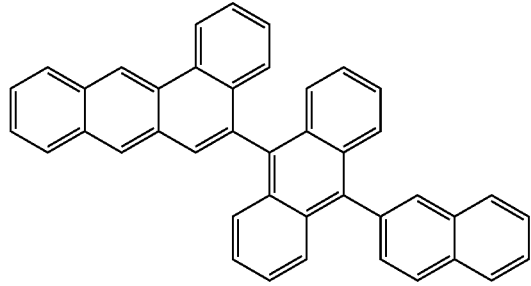

-continued
(59)
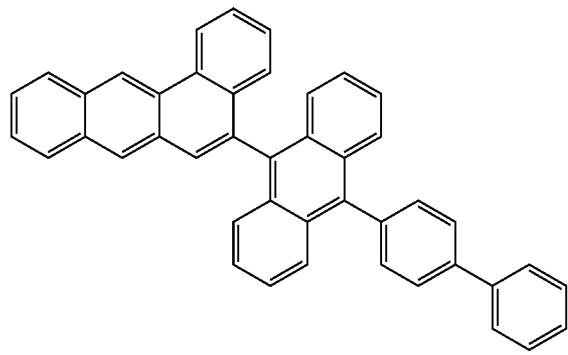
(60)
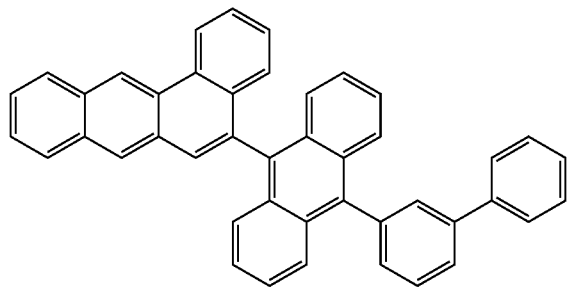
(61)
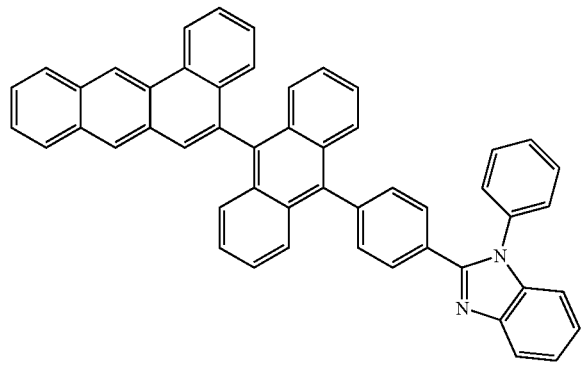
(62)
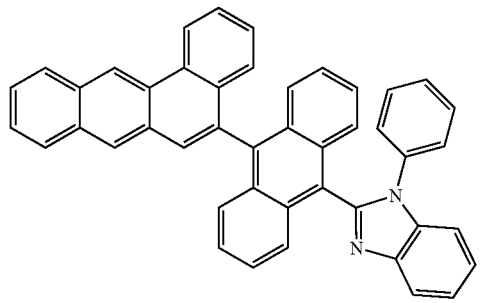
(63)
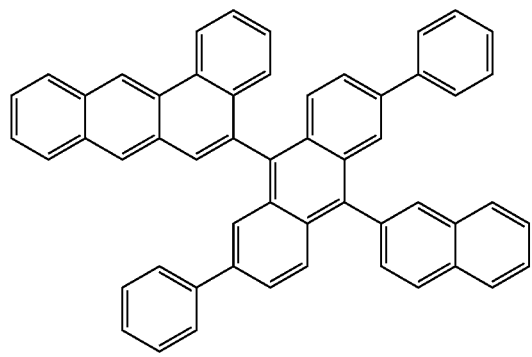
(64)
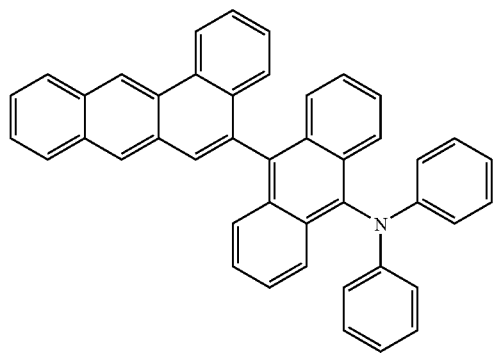
(65)
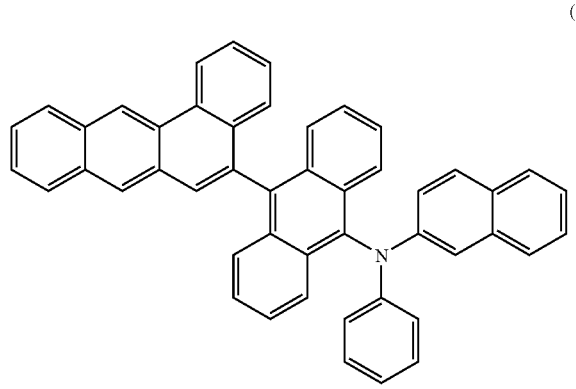
(66)
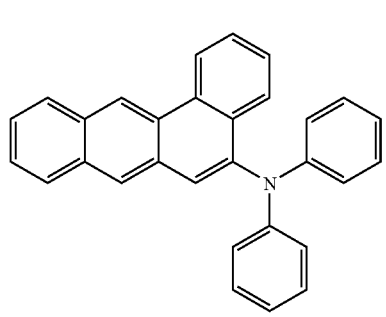

-continued
(67)
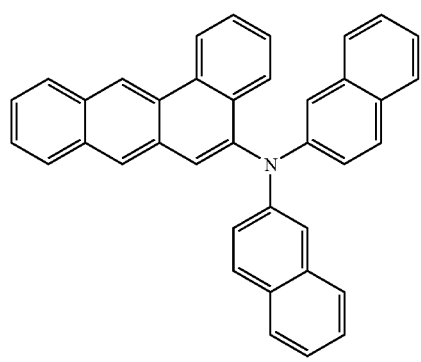
(68)
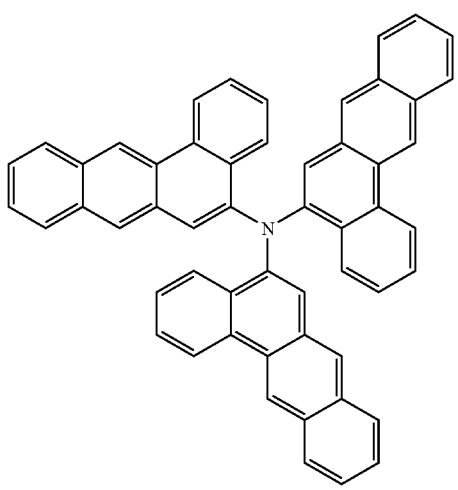
(69)
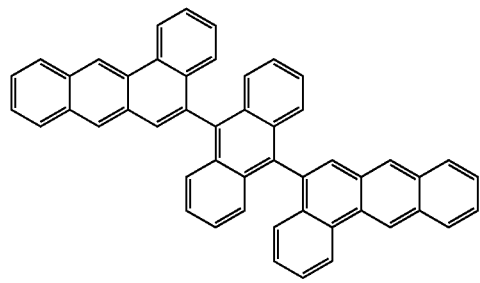
(70)
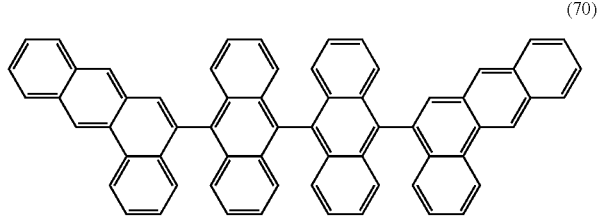
(71)
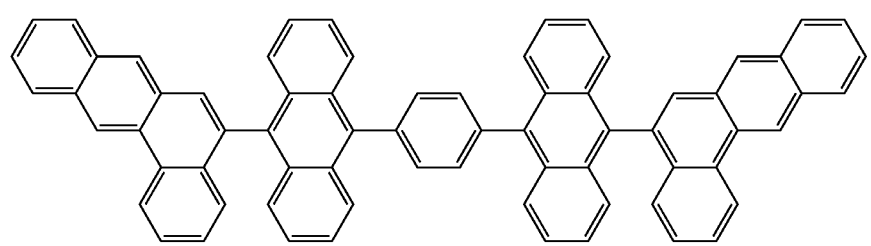
(72)
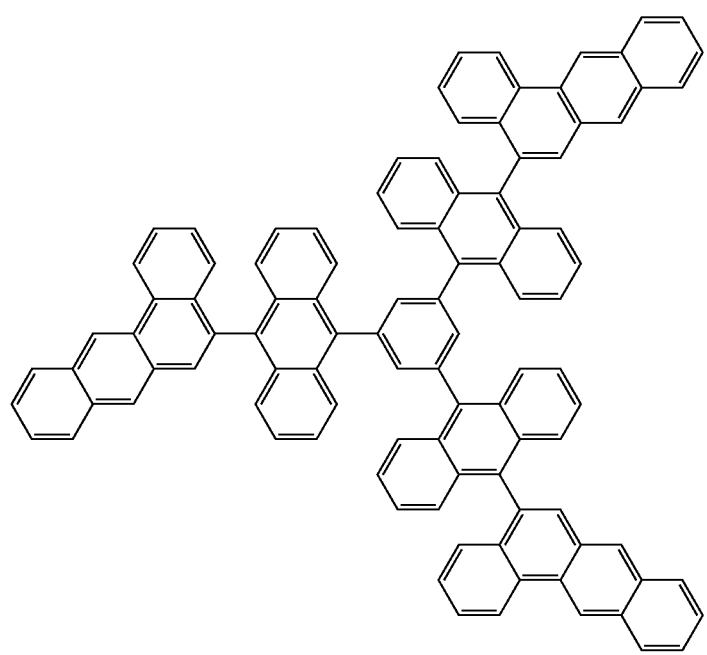

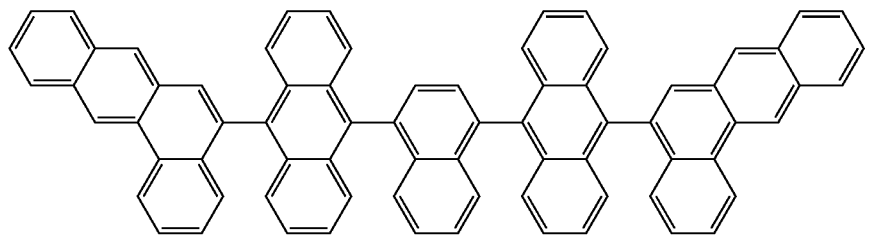
(73)
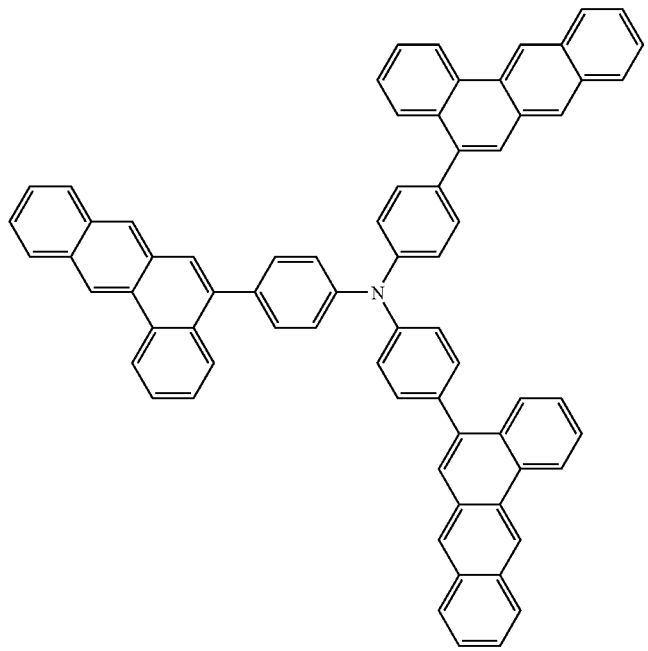
(74)
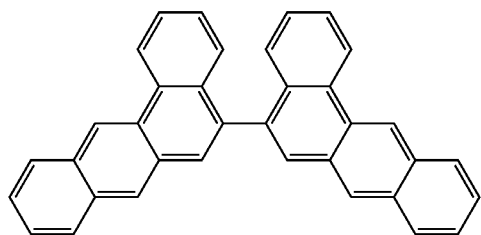
(75)
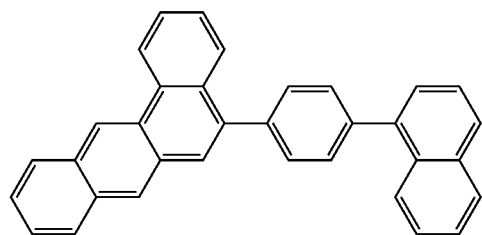
(76)
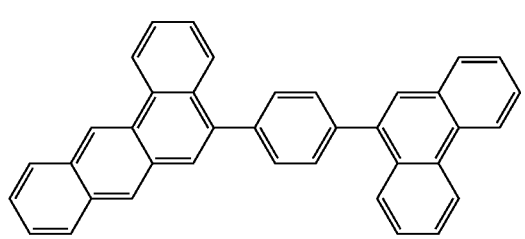
(77)
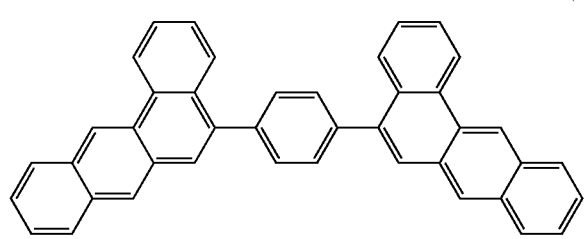
(78)
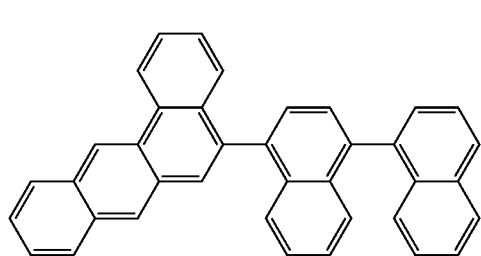
(79)
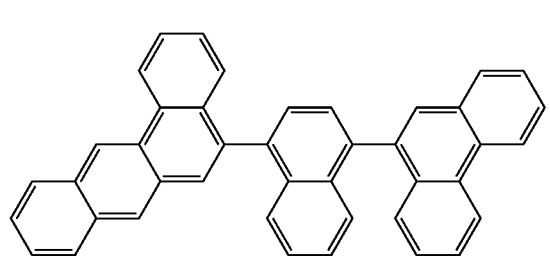
(80)

(81)
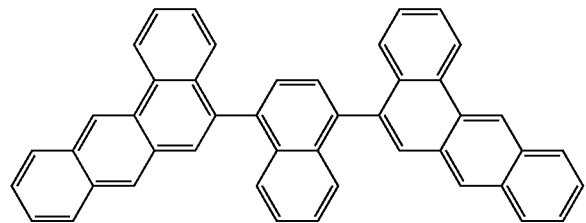
(82)
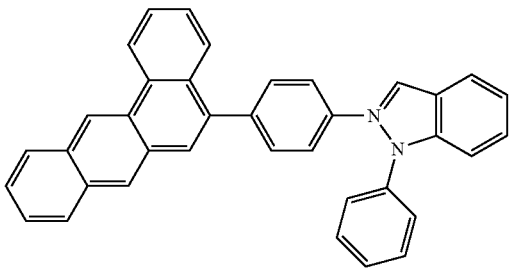
(83)
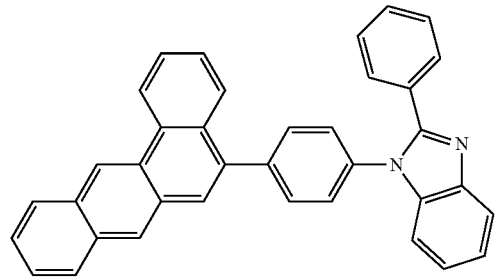
(84)
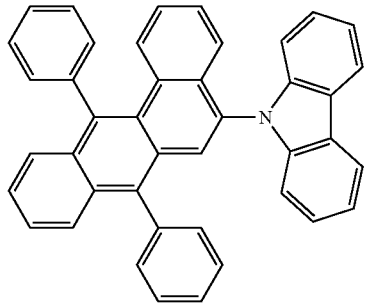
(85)
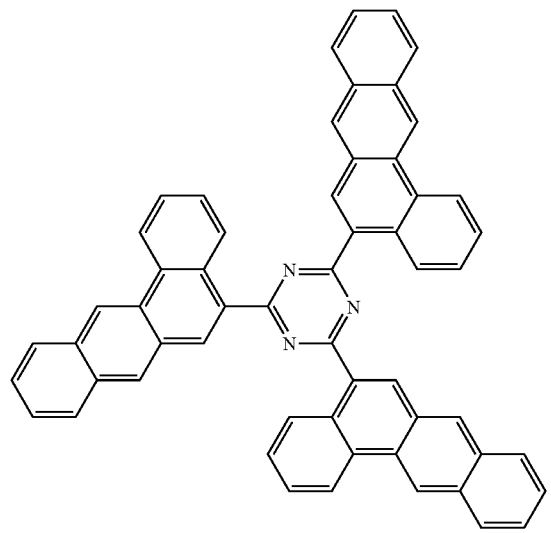
(86)
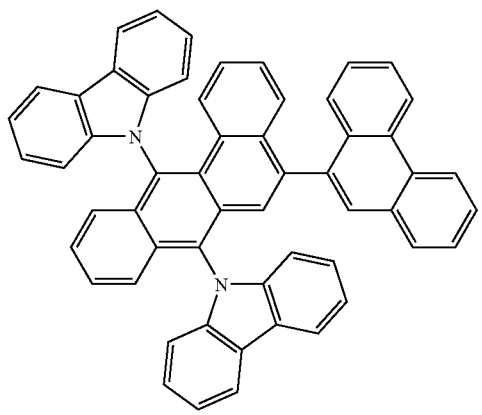
(87)
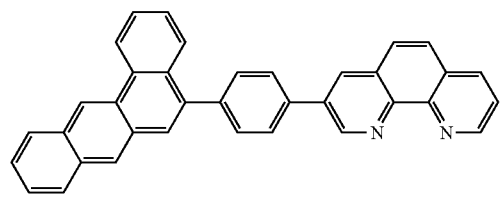
(88)
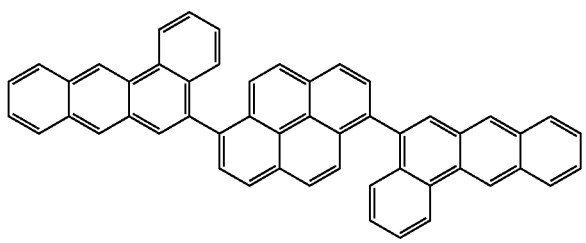
(89)
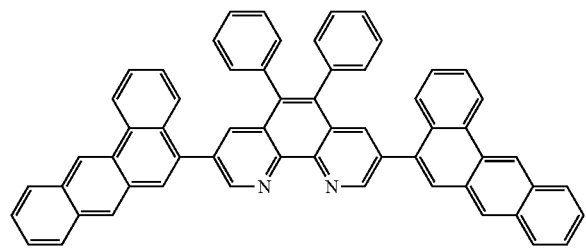
(90)
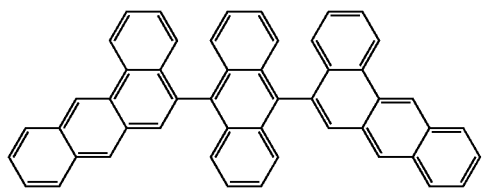

(91)
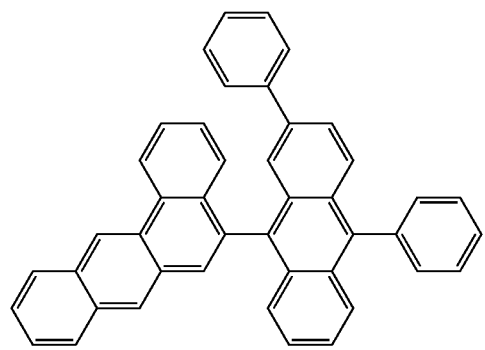
(92)
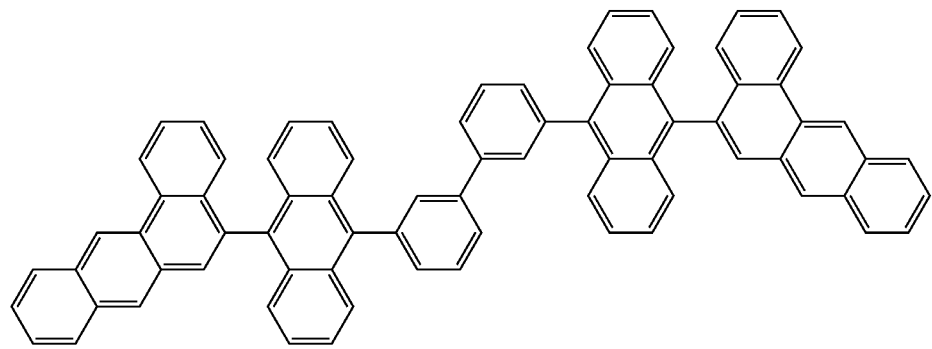
(93)
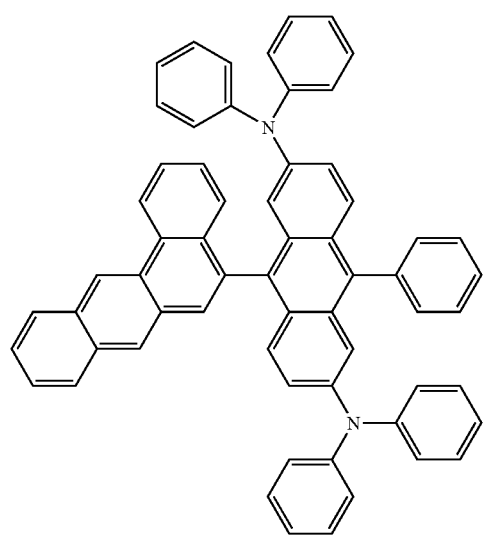
(94)
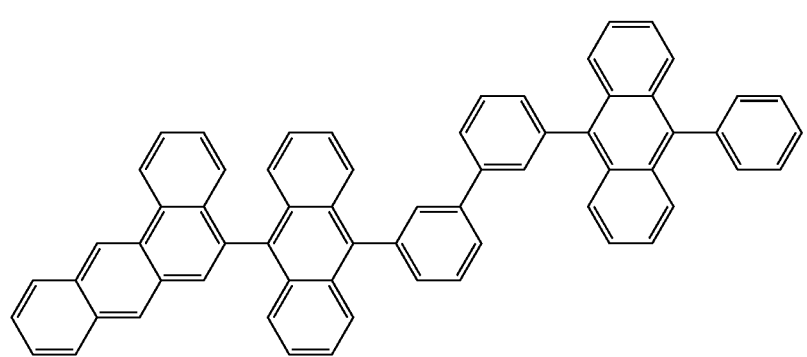

-continued
(95)
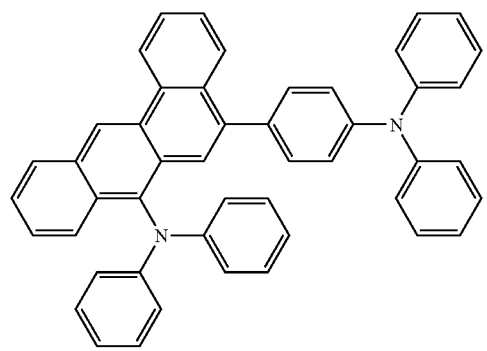
(96)
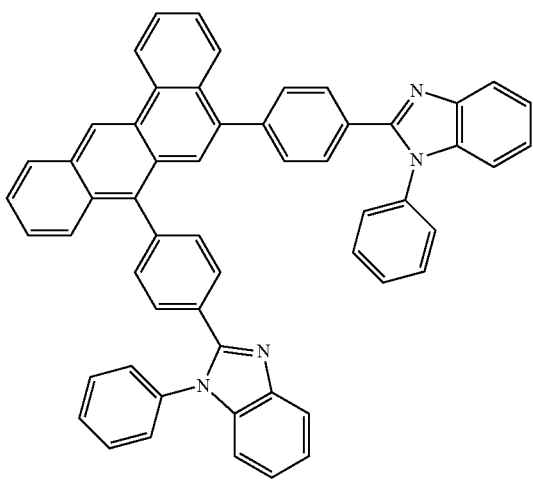
(97)
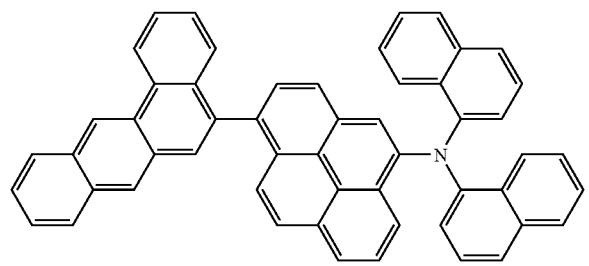
(98)
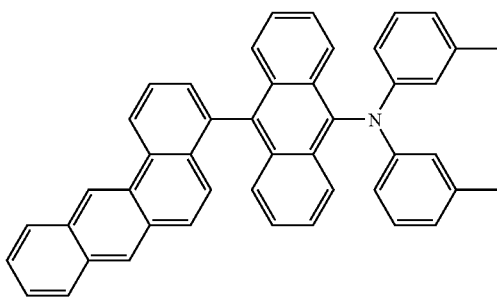
(99)
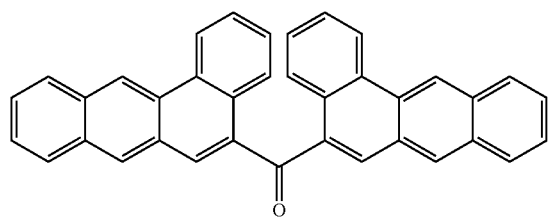
(100)
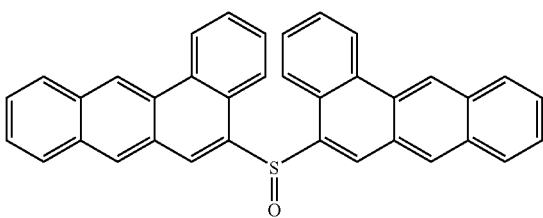
(101)
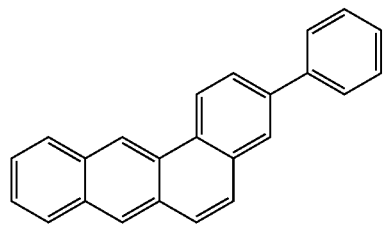
(102)
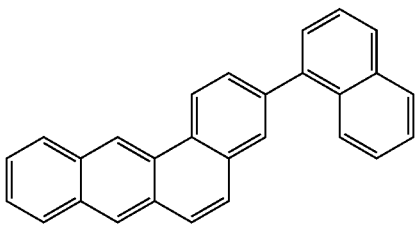
(103)
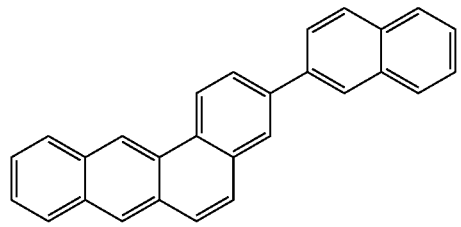
(104)

-continued
(105)
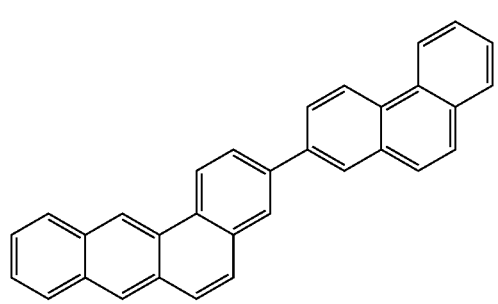
(106)
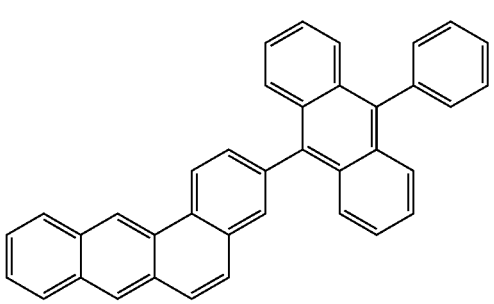
(107)
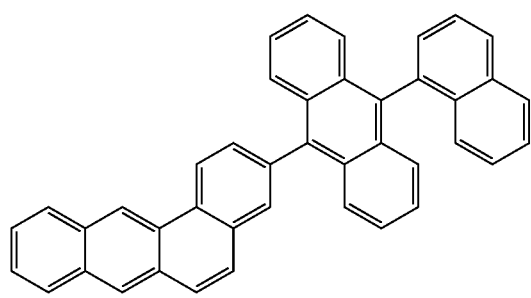
(108)
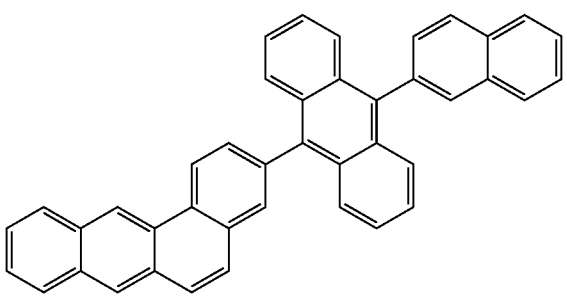
(109)
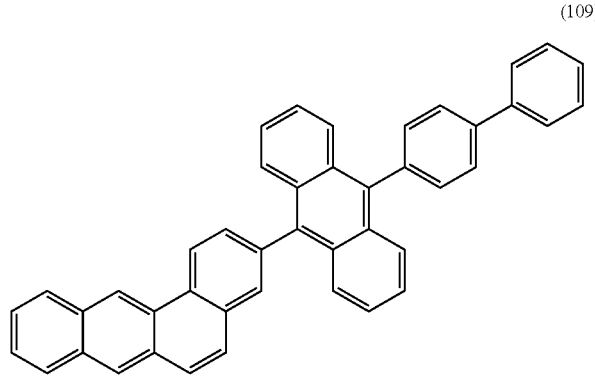
(110)
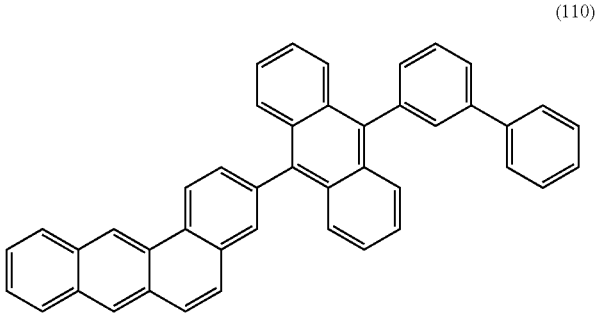
(111)
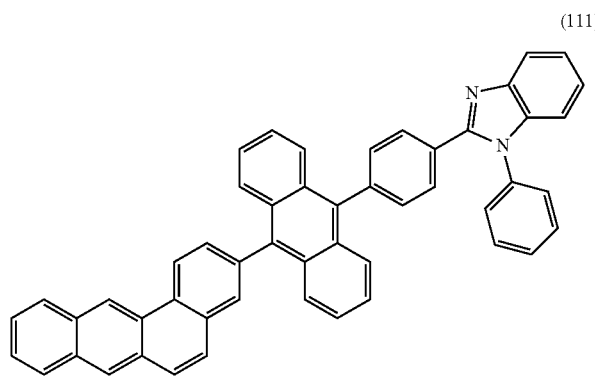
(112)
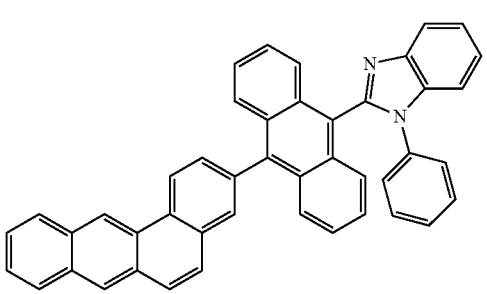

(113)
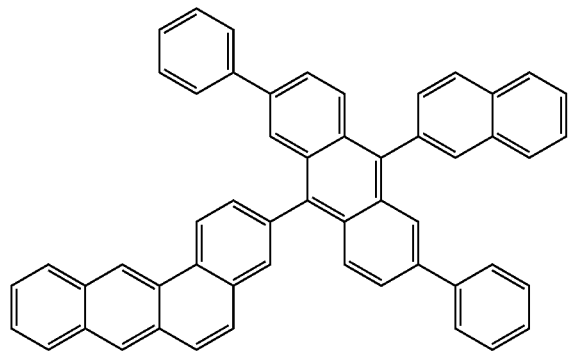
(114)
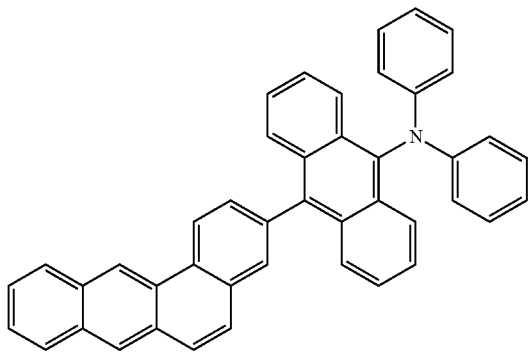
(115)
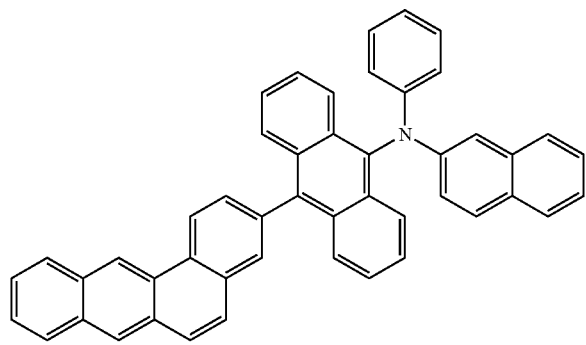
(116)
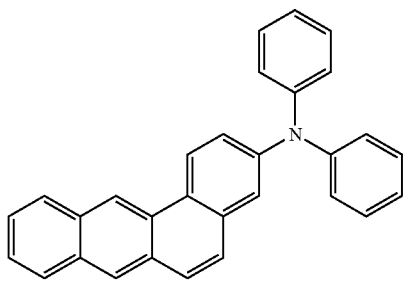
(117)
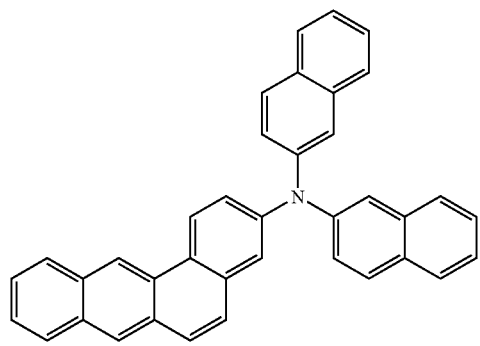
(118)
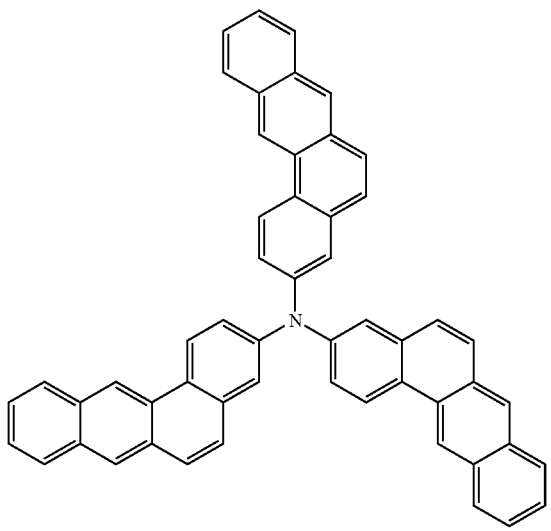

-continued
(119)
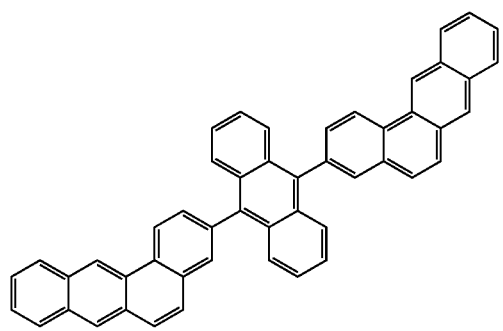
(120)
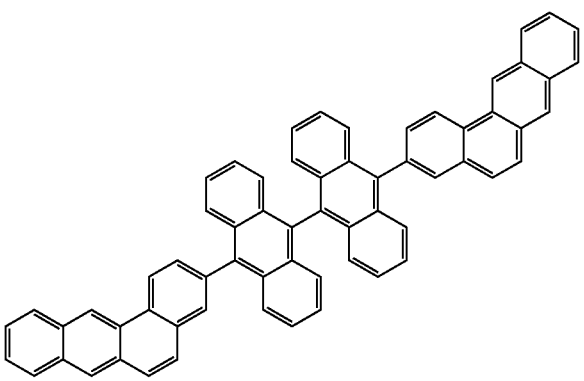
(121)
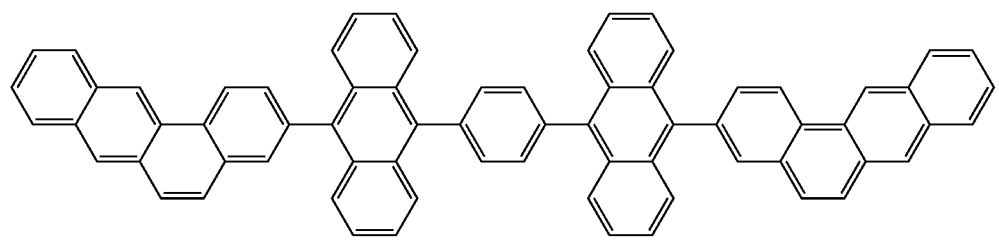
(122)
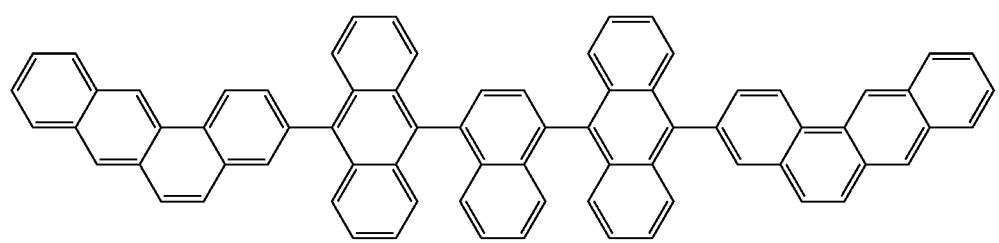
(123)
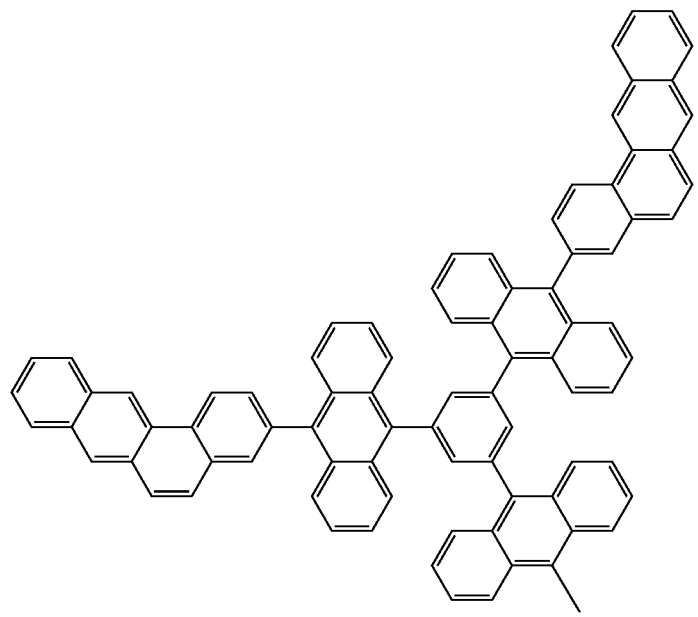

-continued
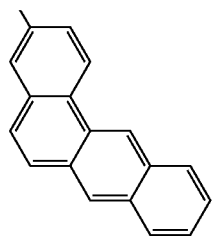
(124)
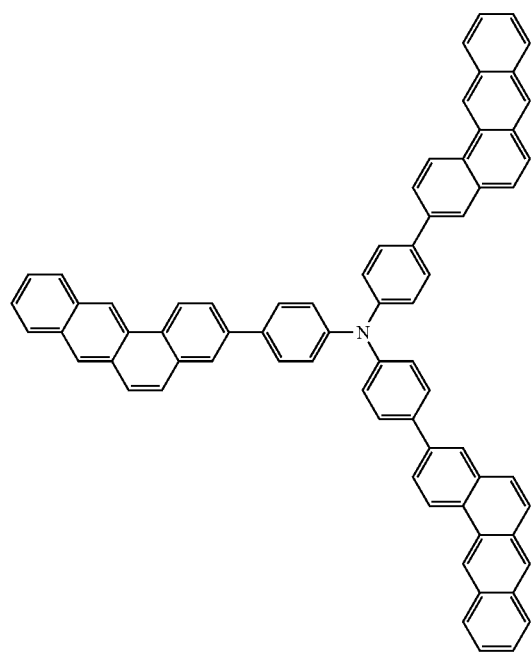
(125)
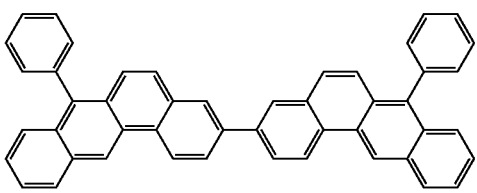
(126)
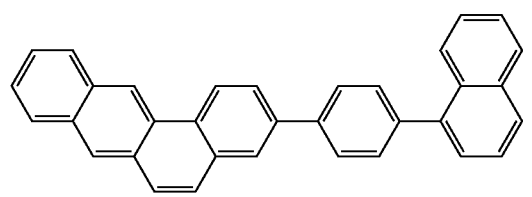
(127)
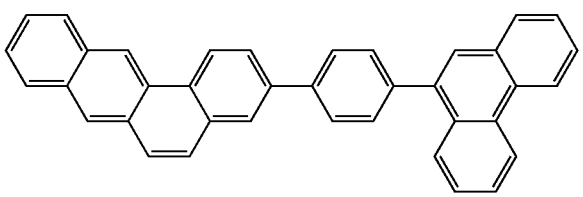
(128)
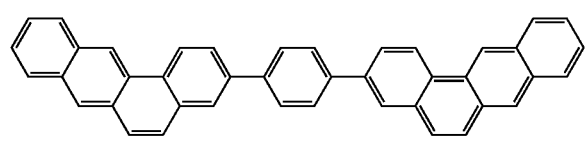
(129)
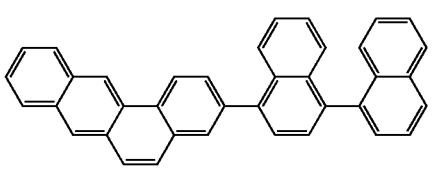
(130)
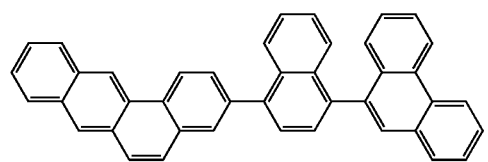
(131)
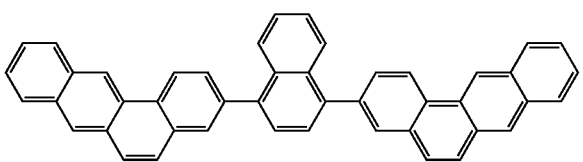

(132)
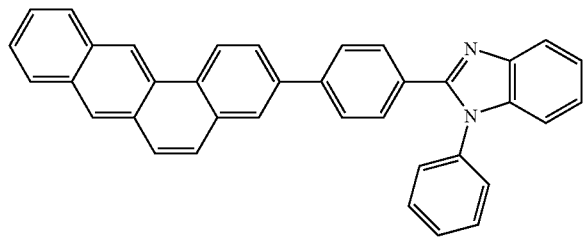
(133)
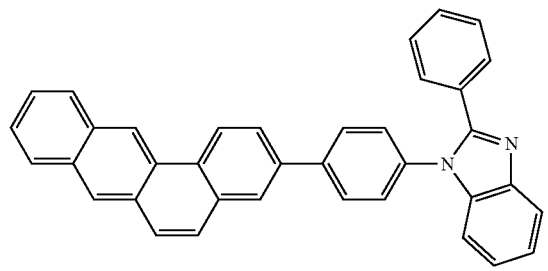
(134)
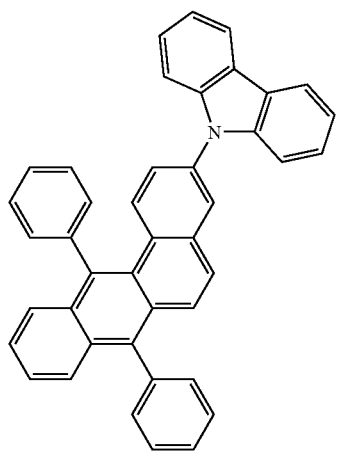
(135)
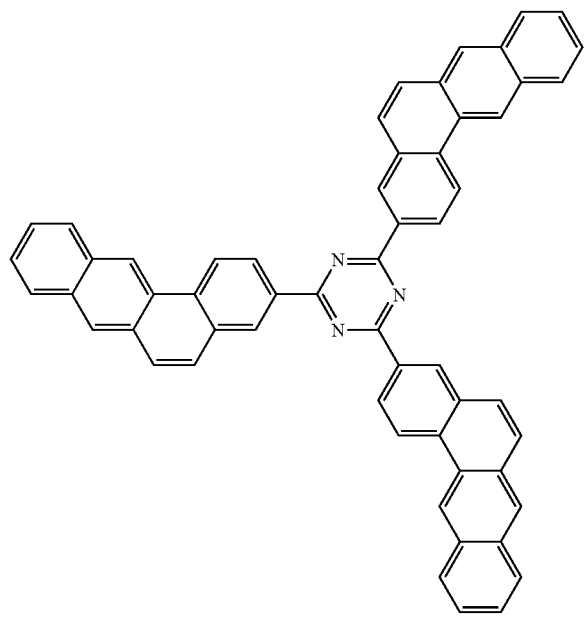
(136)
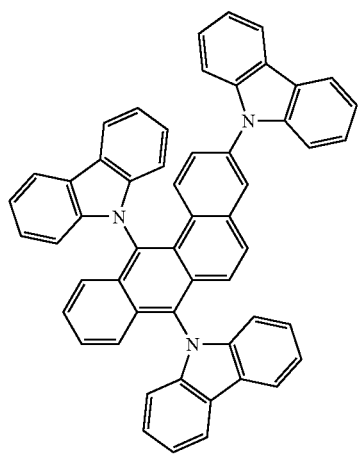
(137)
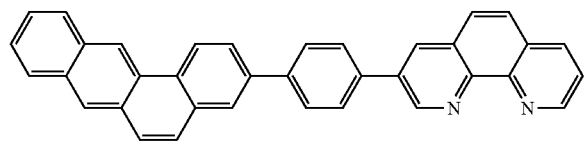

-continued
(138)
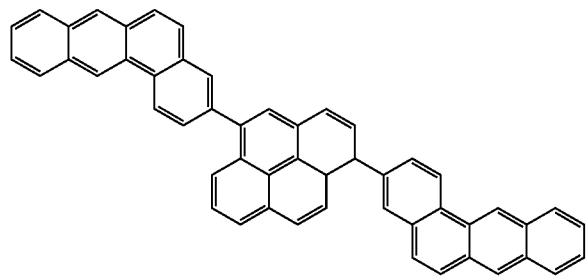
(139)
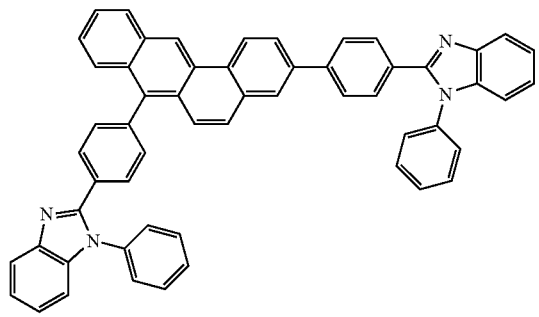
(140)
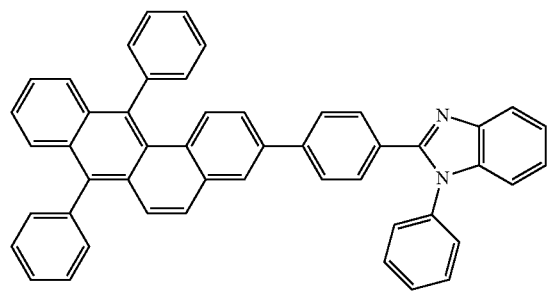
(141)
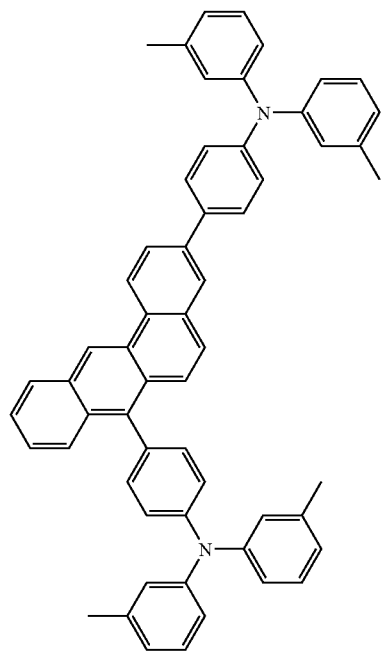
(142)
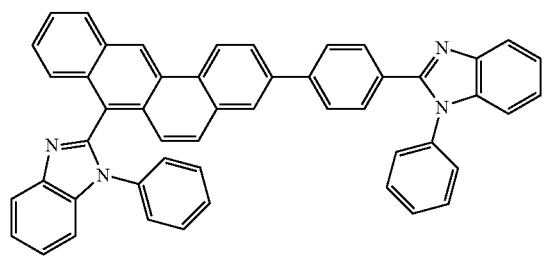
(143)
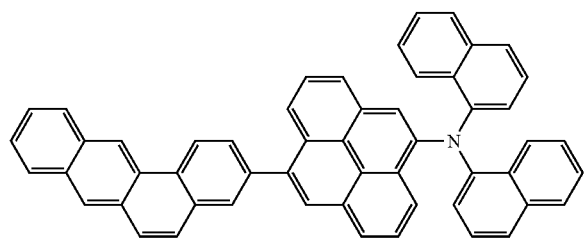
(144)
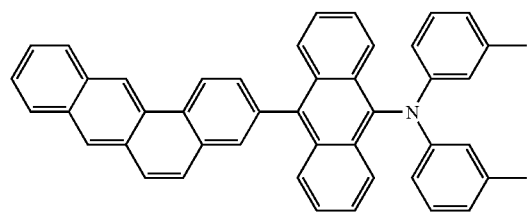
(145)
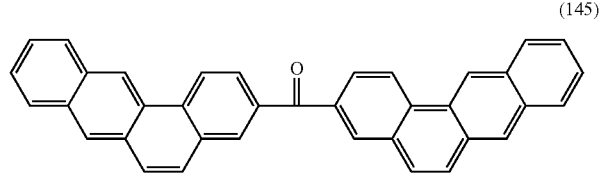

-continued
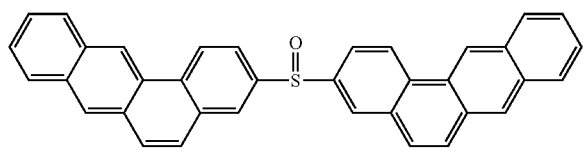
(146)
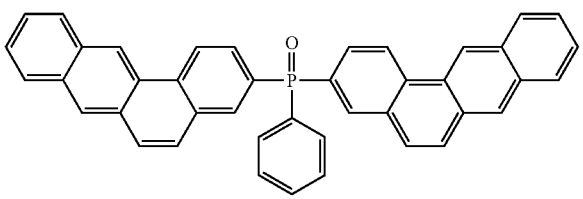
(147)
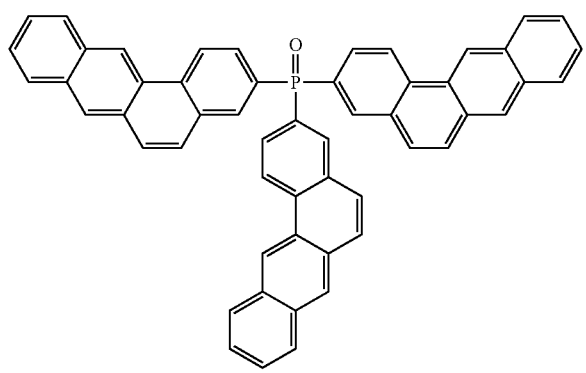
(148)
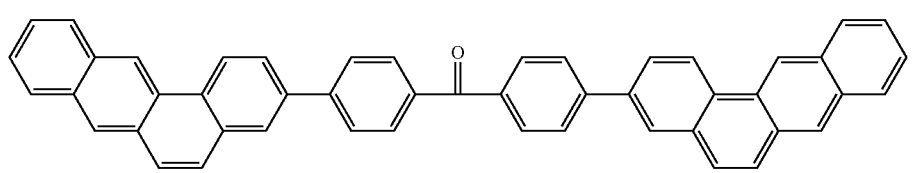
(149)
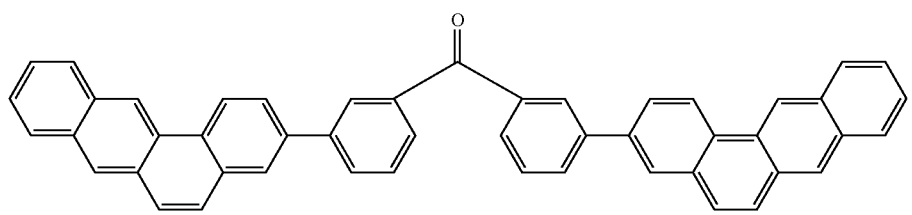
(150)
(151) (152)
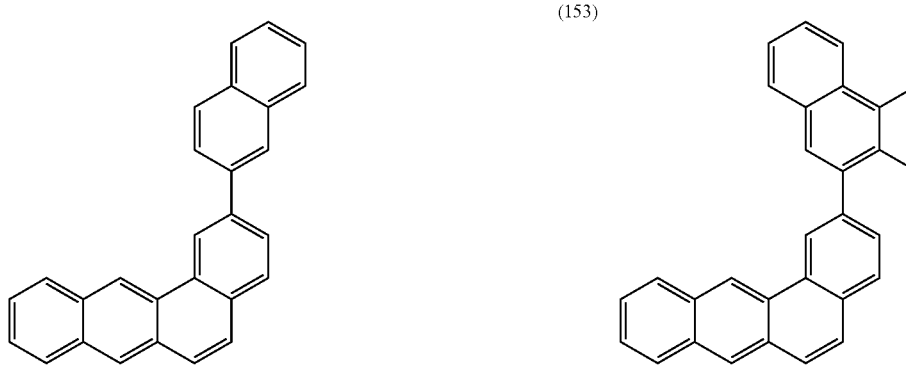
(153) (154)

-continued
(155)
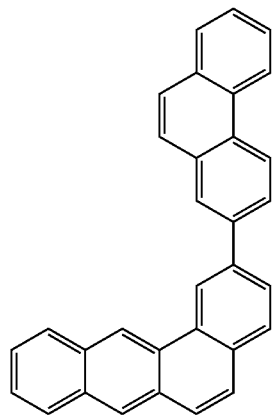
(156)
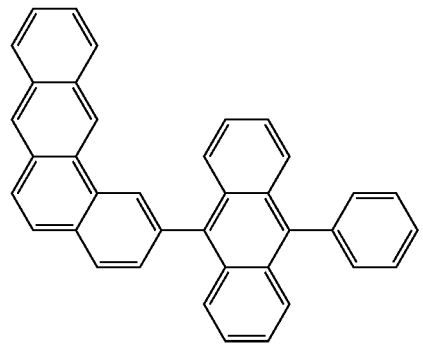
(157)
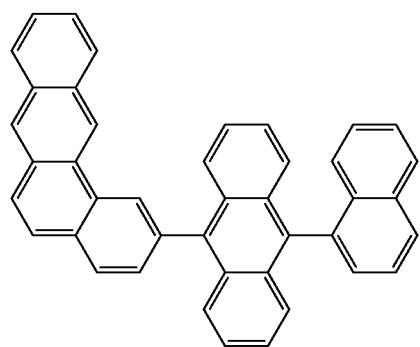
(158)
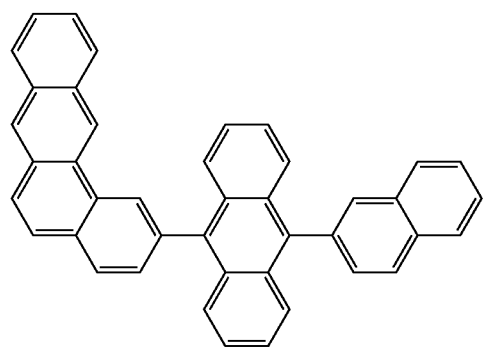
(159)
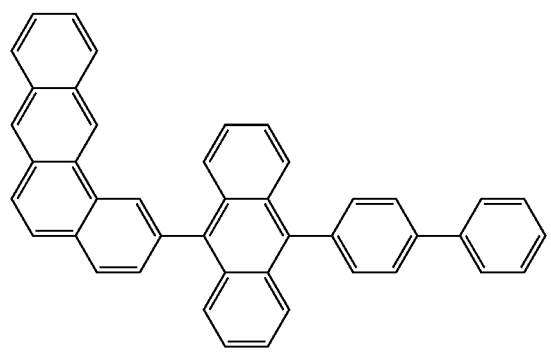
(160)
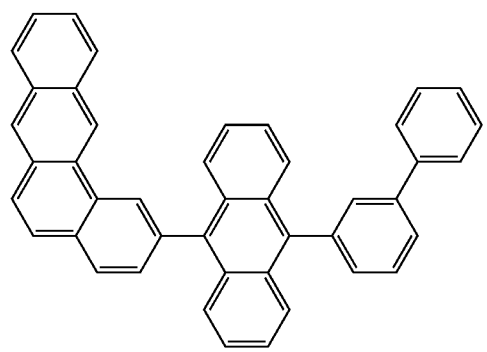
(161)
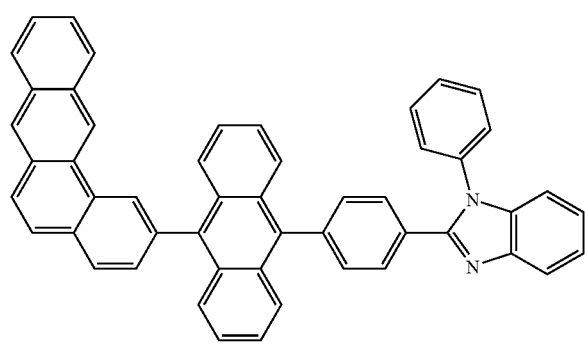
(162)
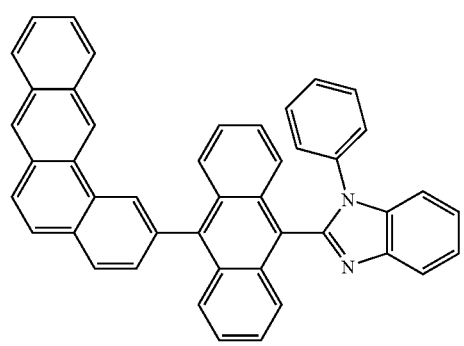

-continued
(163)
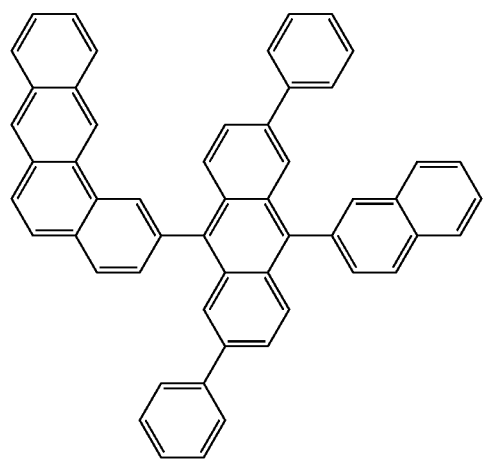
(164)
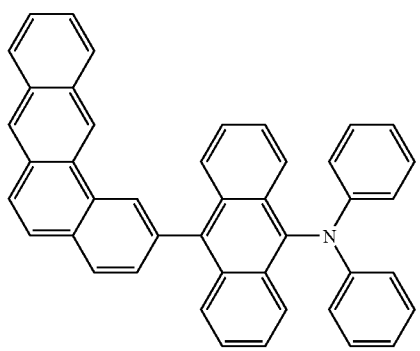
(165)
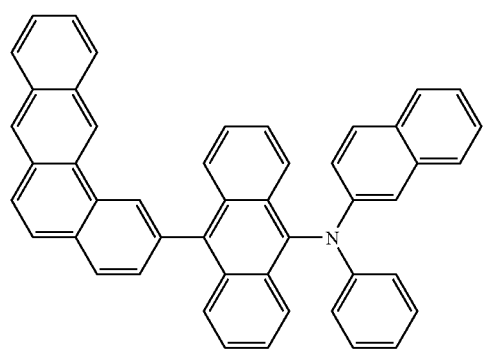
(166)
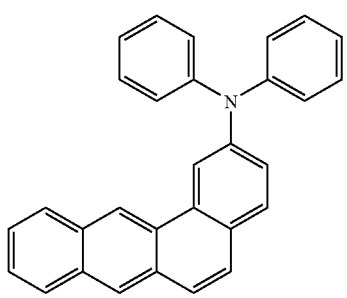
(167)
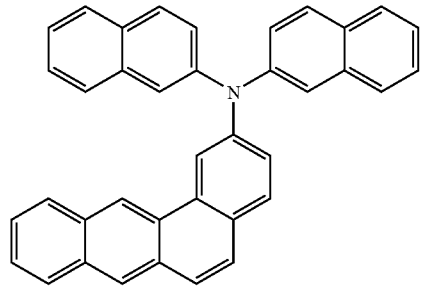
(168)
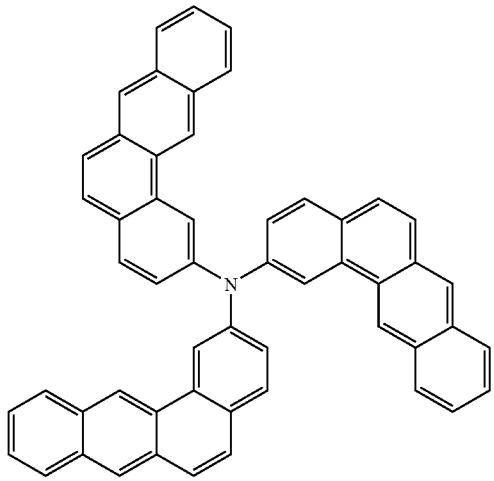
(169)
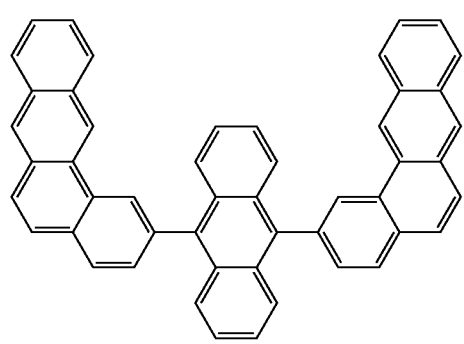
(170)
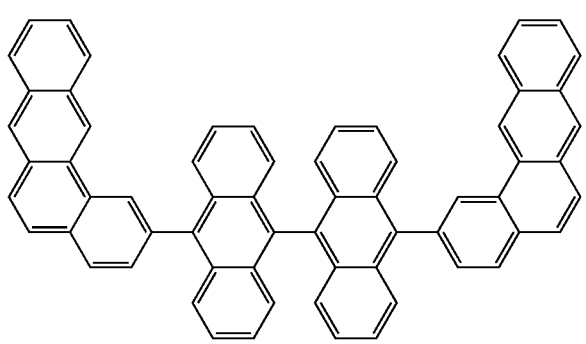

-continued
(171)
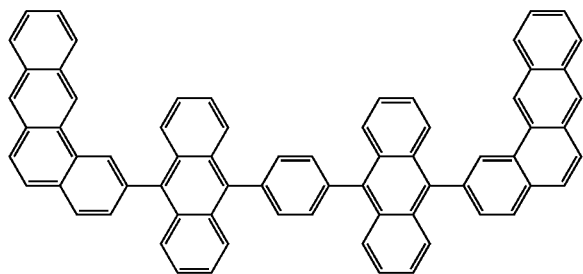
(172)
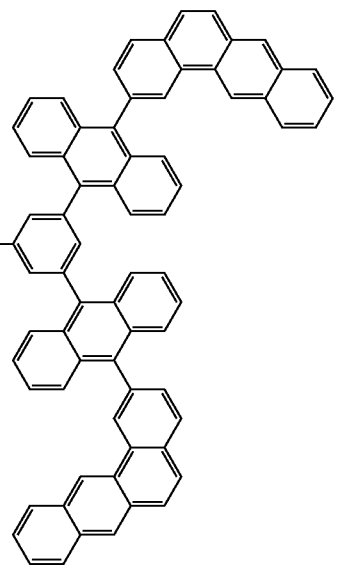
(173)
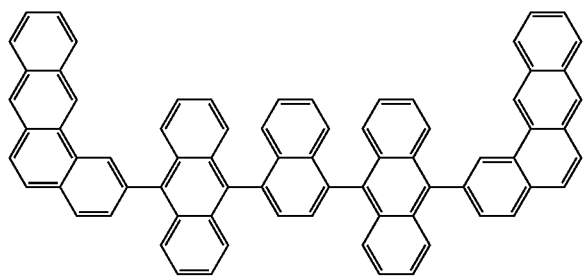
(174)
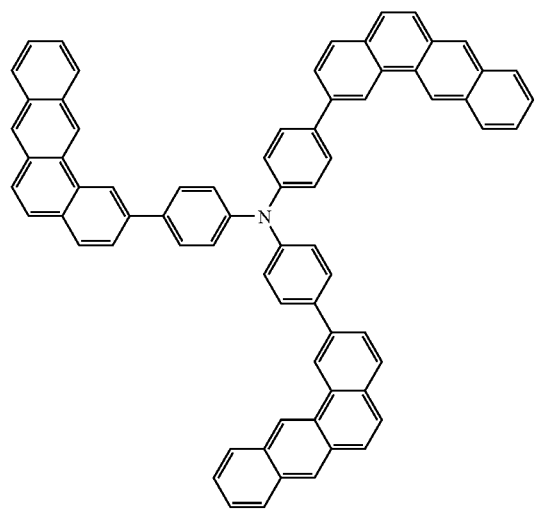
(175)
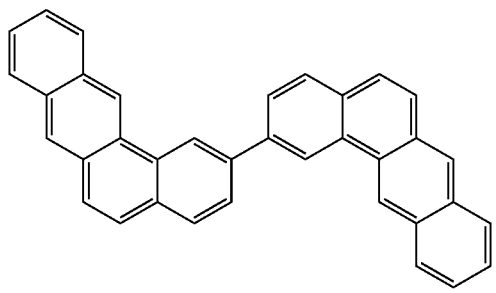
(176)
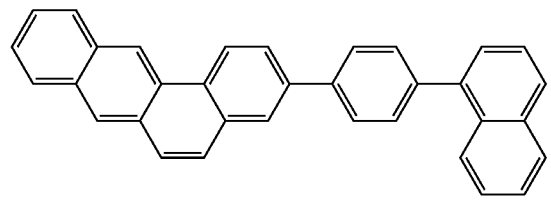
(177)
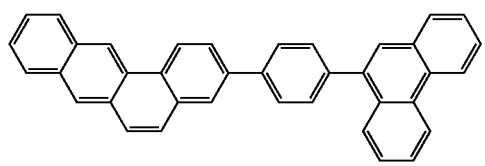
(178)
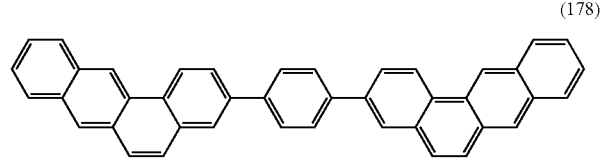

(179) 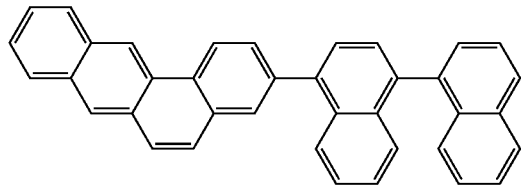
(180) 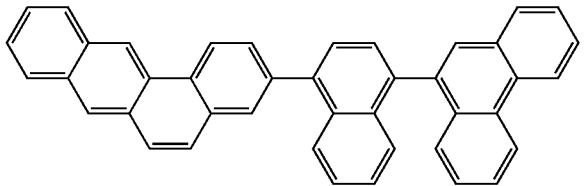
(181) 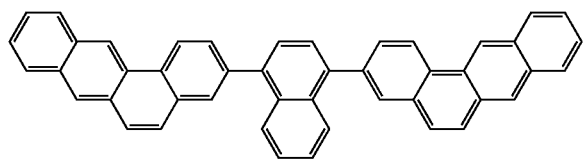
(182) 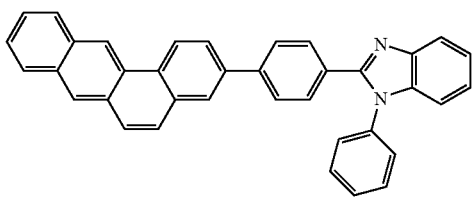
(183) 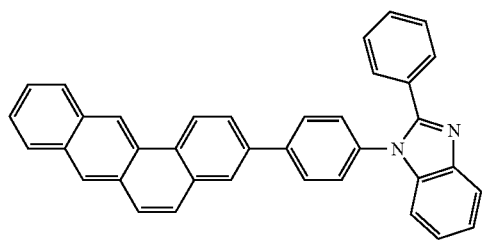
(184) 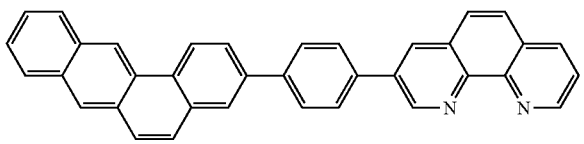
(185) 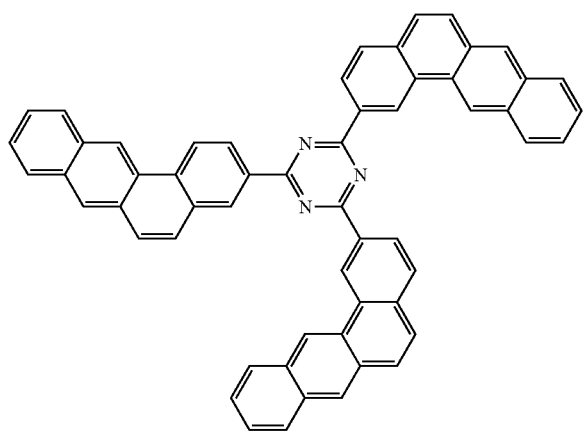
(186) 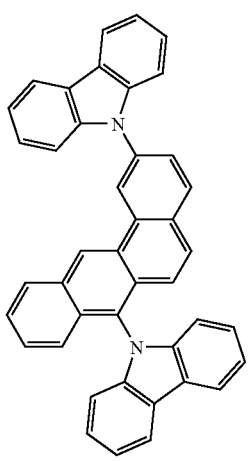

-continued
(187)
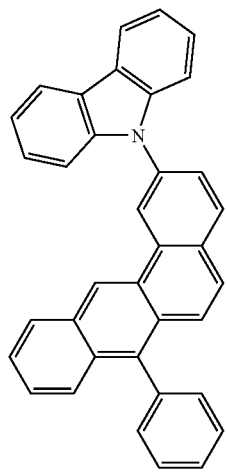
(188)
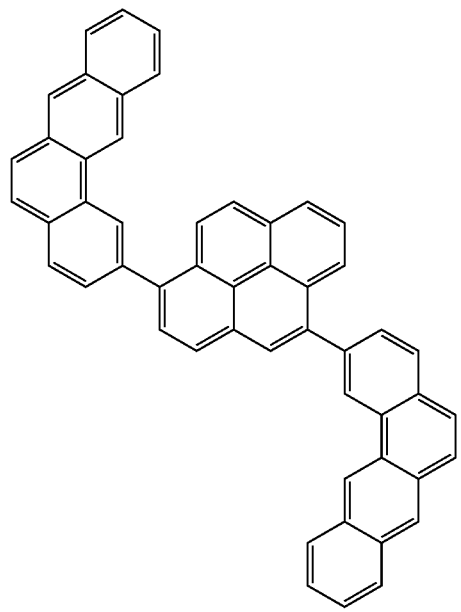
(189)
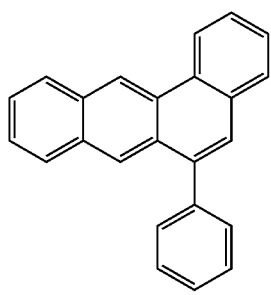
(190)
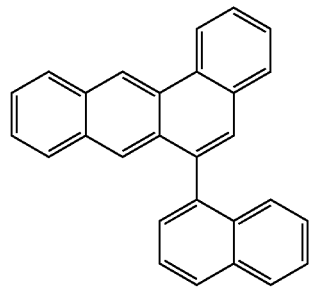
(191)
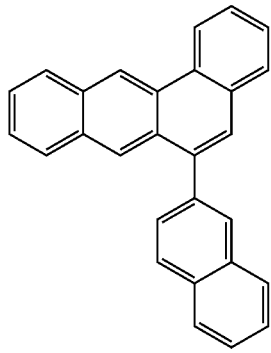
(192)
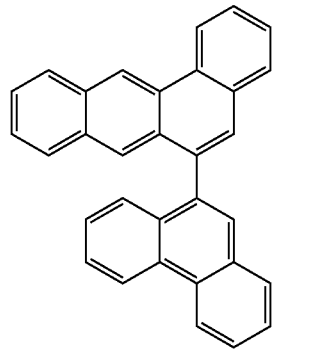
(193)
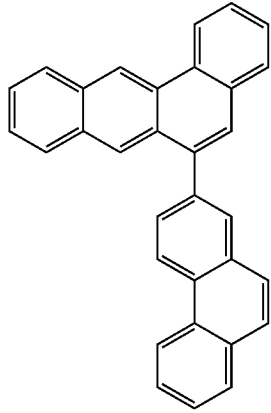
(194)
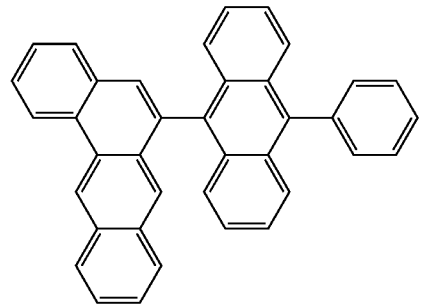

-continued
(195)
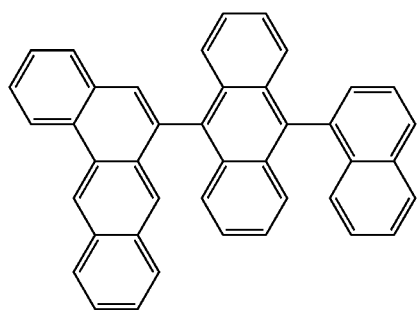
(196)
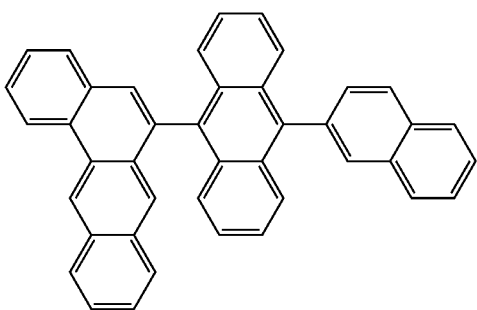
(197)
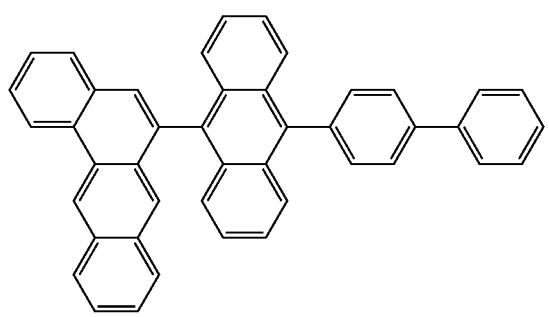
(198)
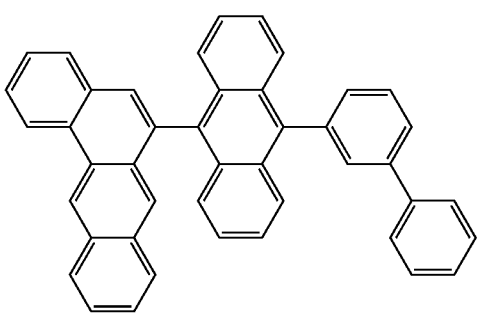
(199)
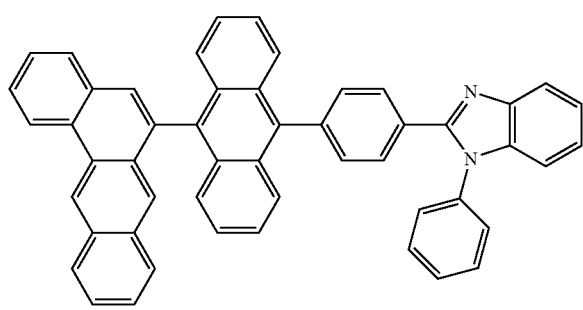
(200)
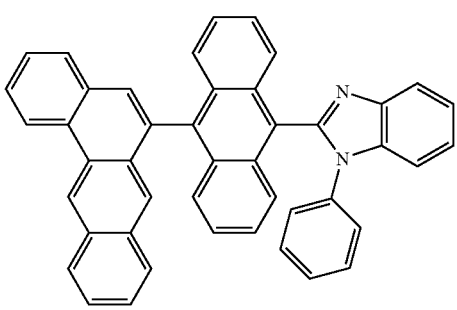
(201)
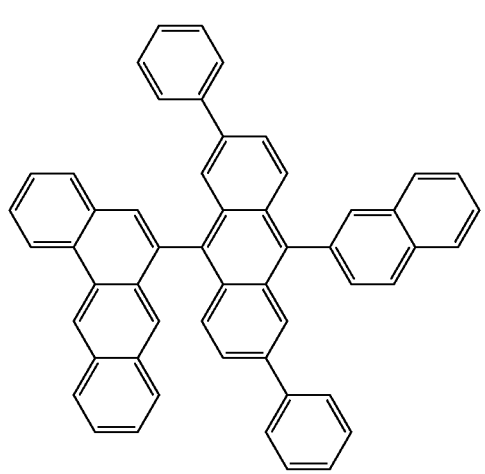
(202)
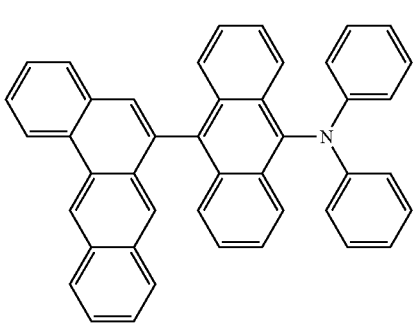

-continued
(203)
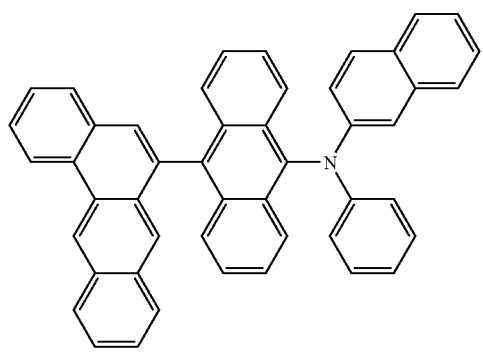
(204)
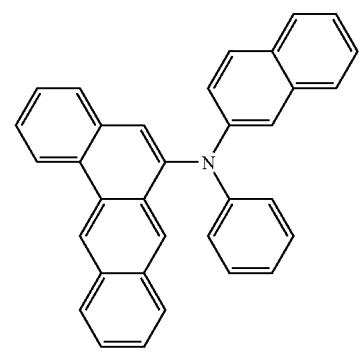
(205)
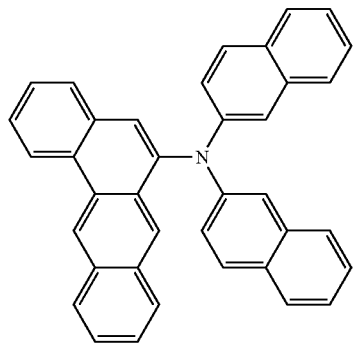
(206)
(207)
(208)
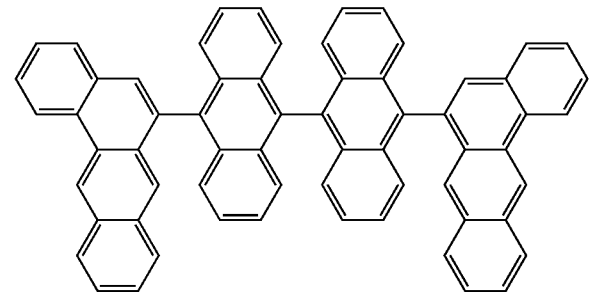
(209)
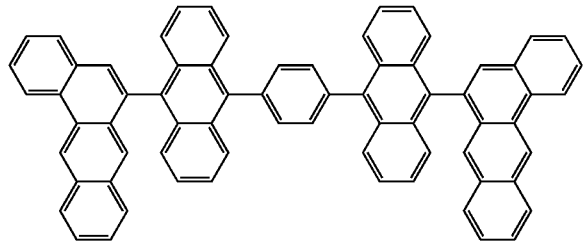
(210)
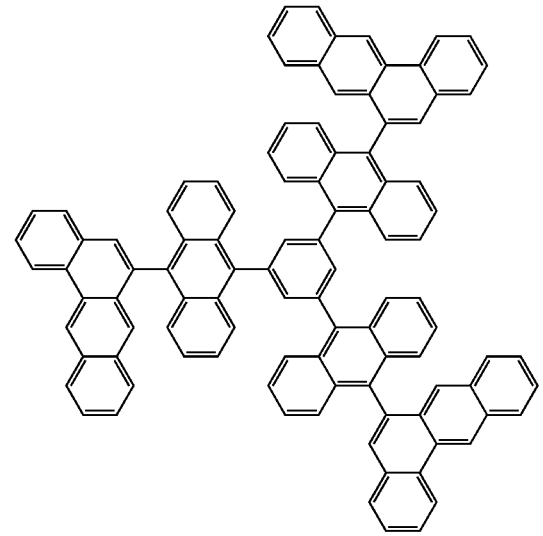

-continued
(211)
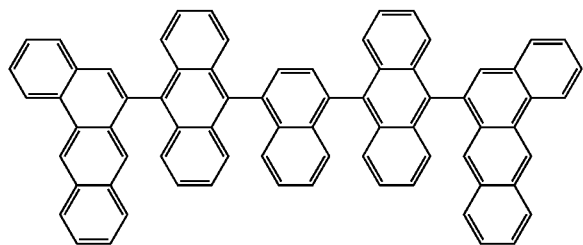
(212)
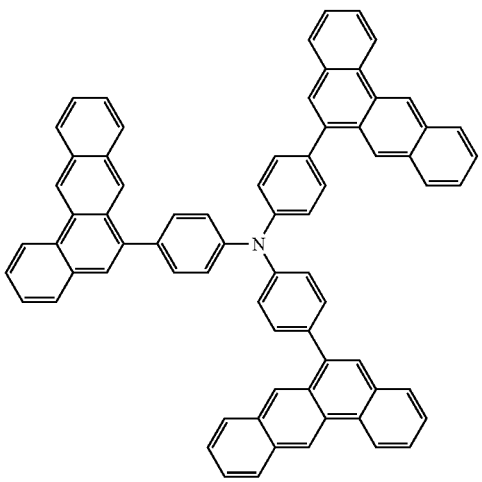
(213)
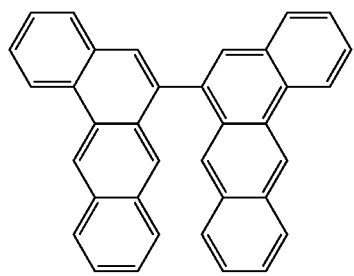
(214)
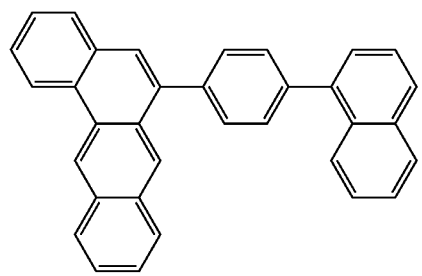
(215)
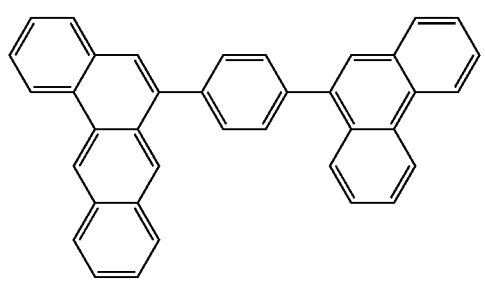
(216)
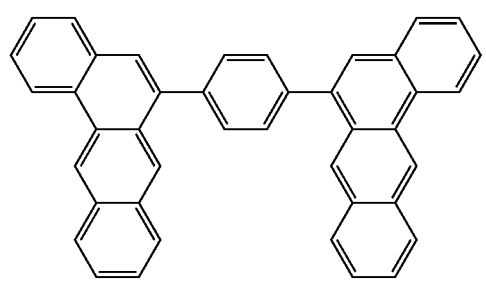
(217)
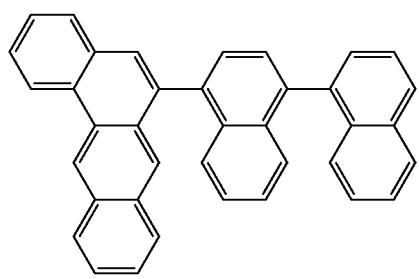
(218)
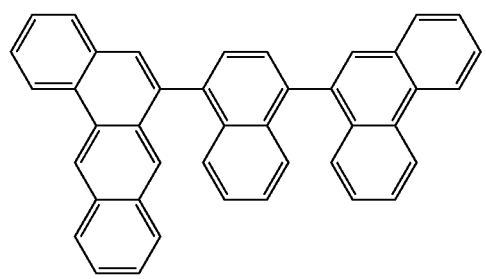
(219)
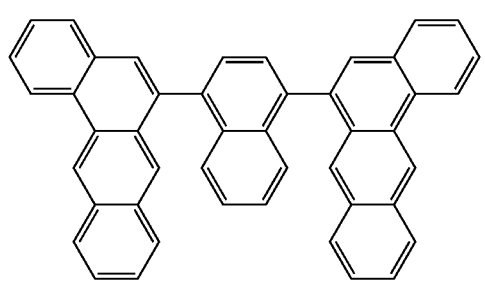
(220)
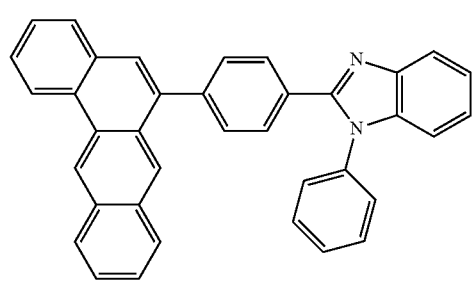

-continued
(221)
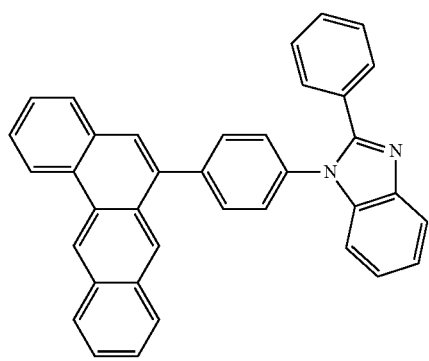
(222)
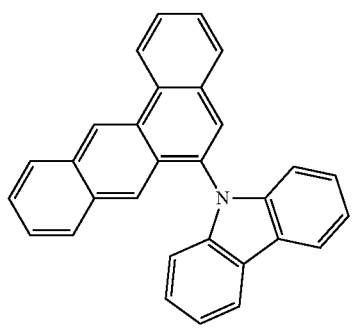
(223)
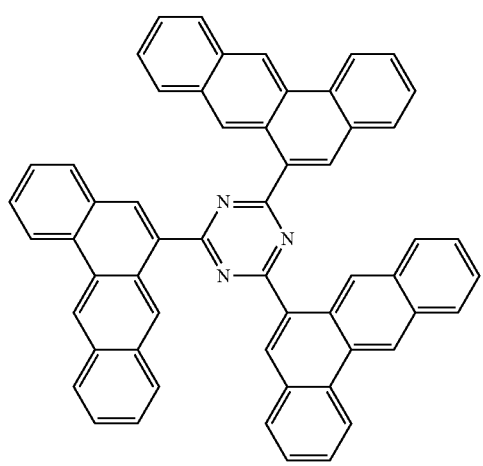
(224)
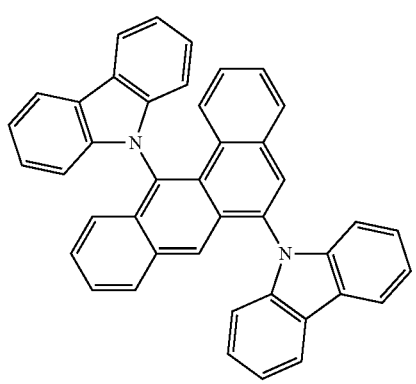
(225)
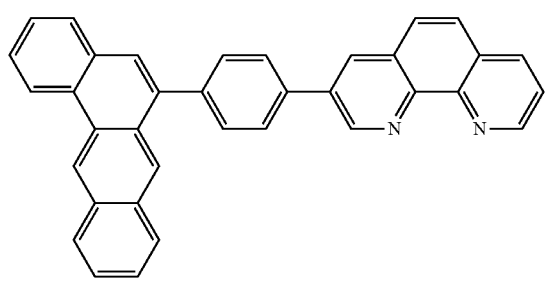
(226)
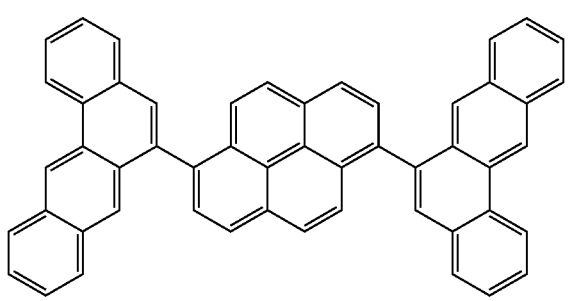
(227)
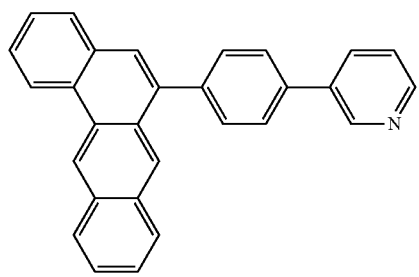
(228)
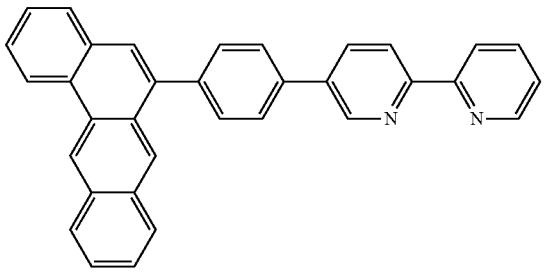

-continued
(229)
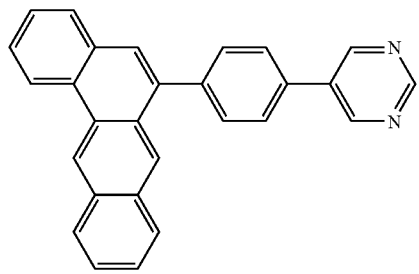
(230)
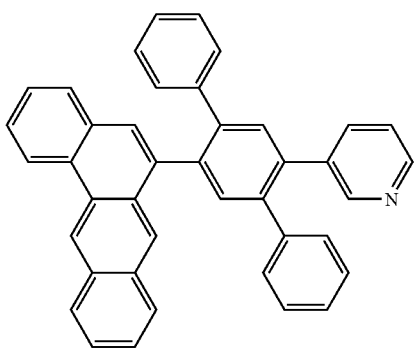
(231)
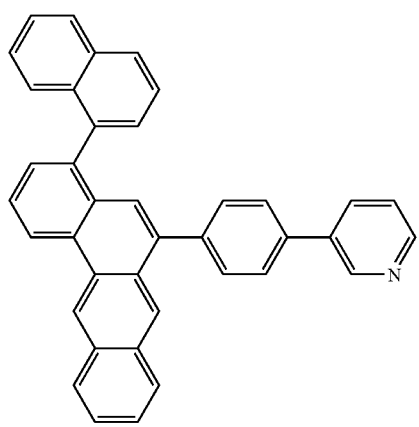
(232)
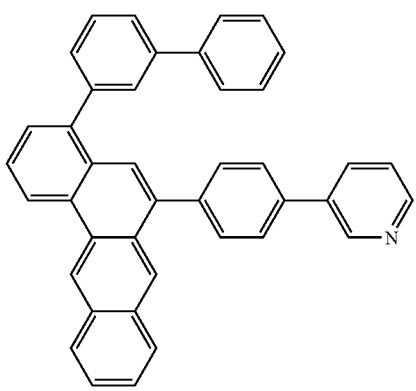
(233)
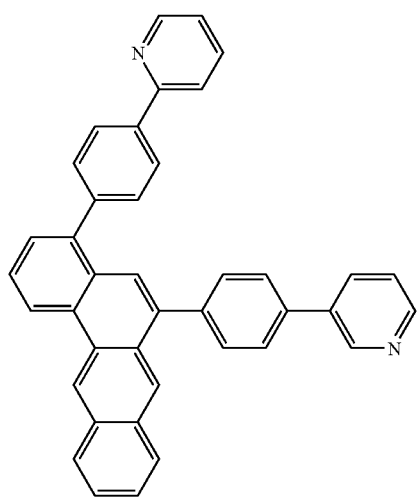
(234)
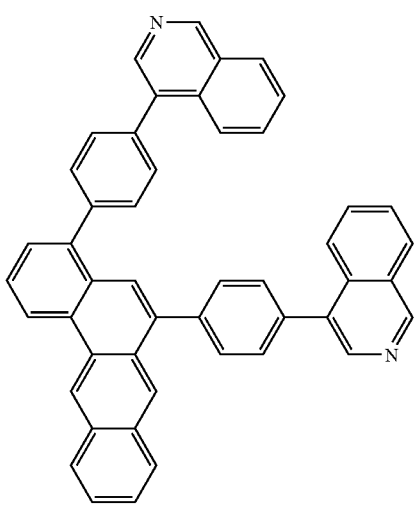

-continued
(235)
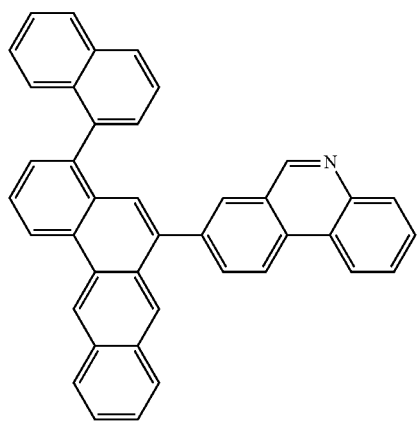
(236)
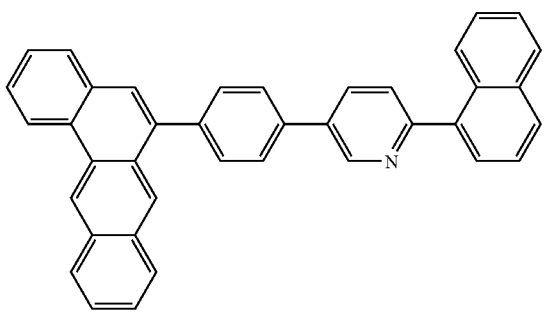
(237)
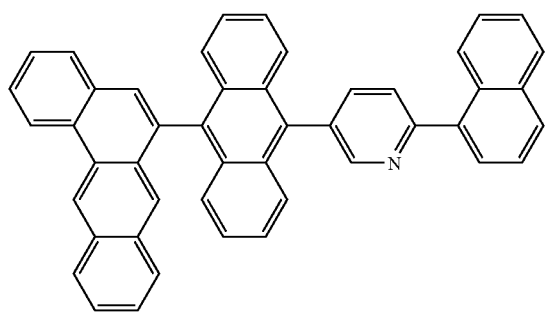
(238)
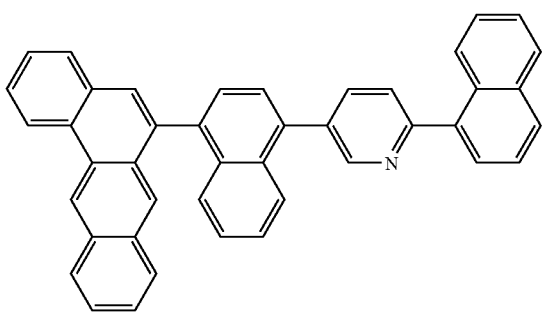
(239)
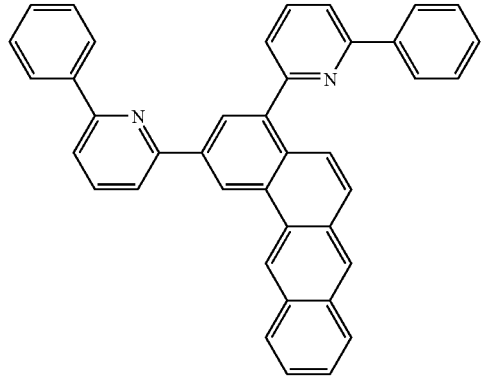
(240)
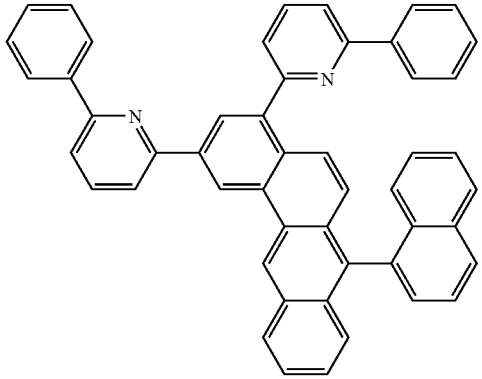
(241)
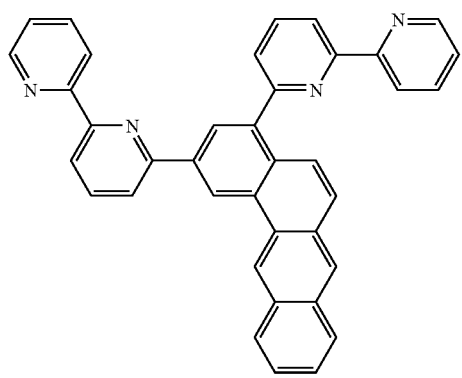
(242)
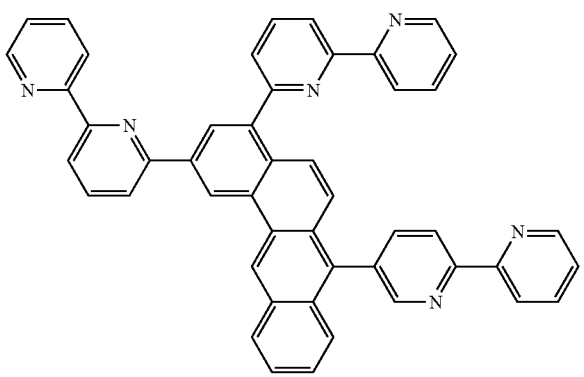

-continued
(243)
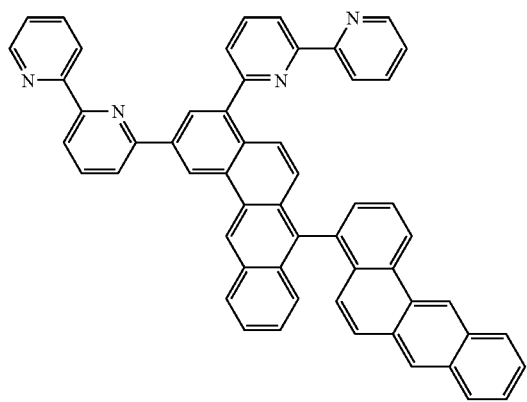
(244)
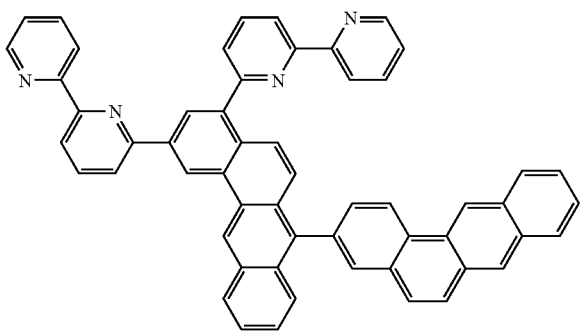
(245)
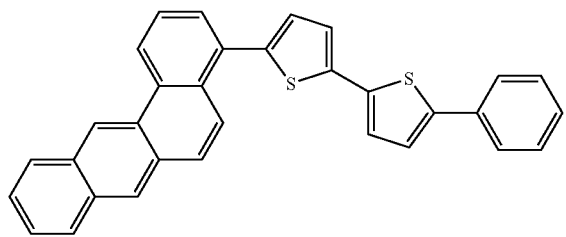
(246)
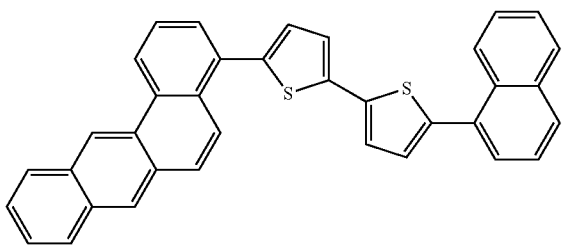
(247)
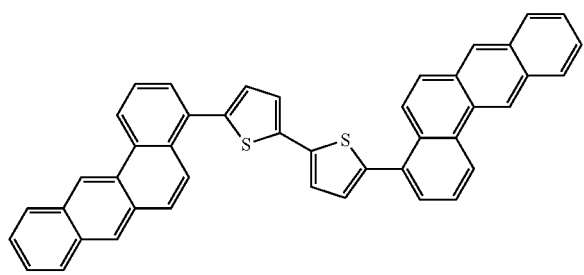
(248)
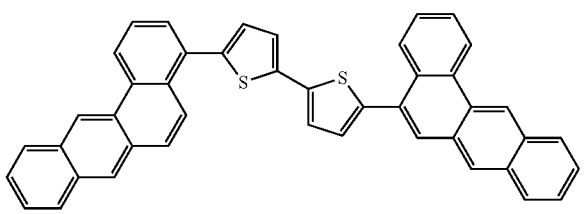
(249)
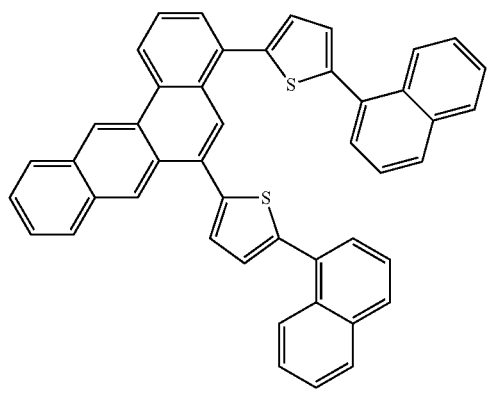
(250)
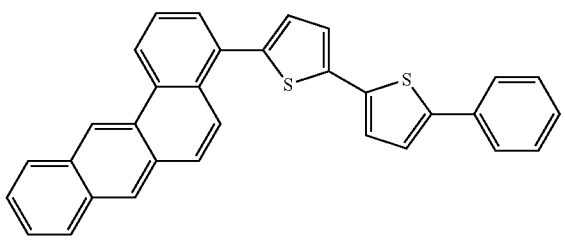

-continued
(251) 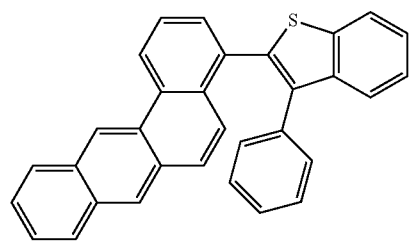
(252) 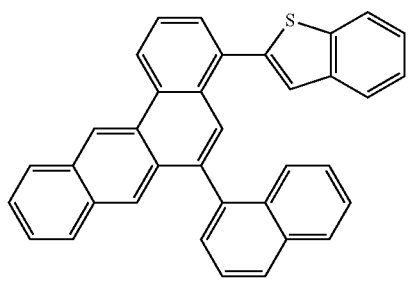
(253) 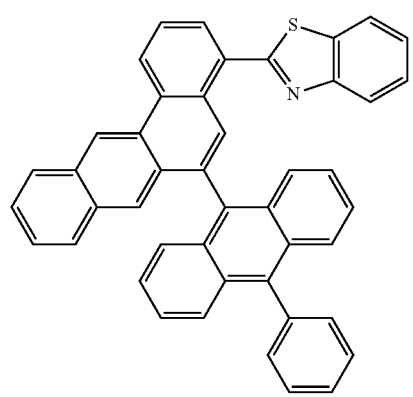
(254) 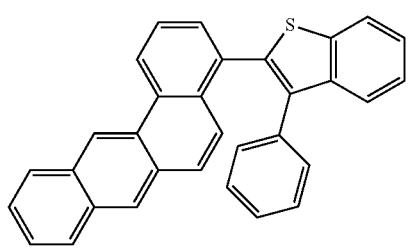
(255) 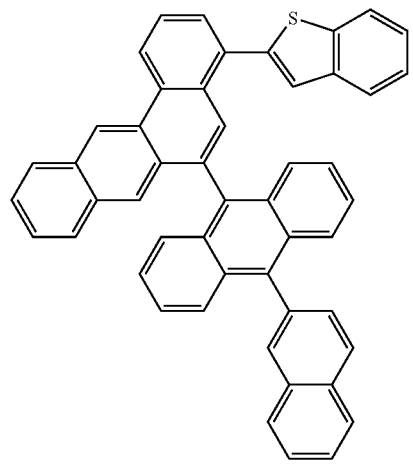
(256) 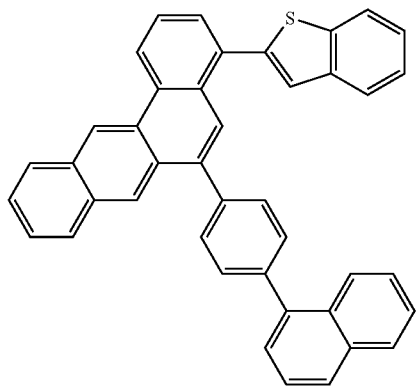
(257) 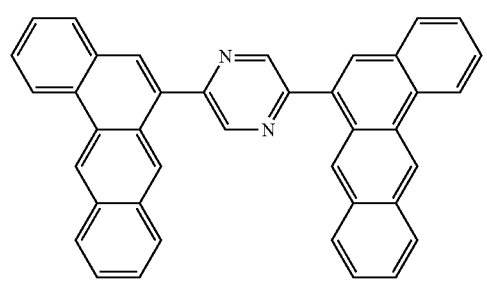
(258) 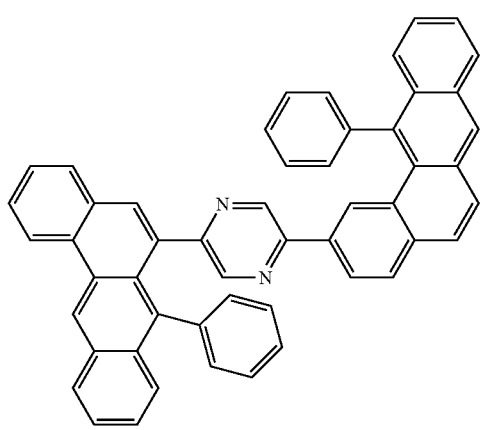

-continued
(259)
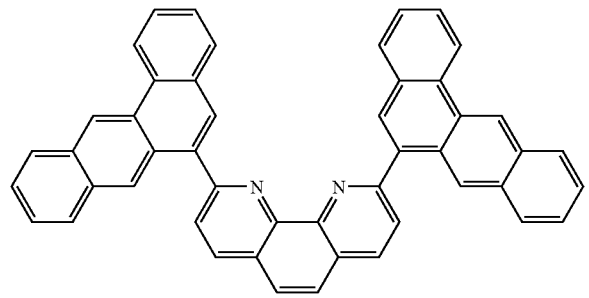
(260)
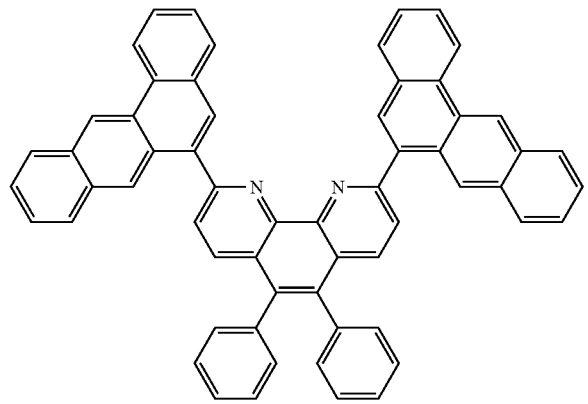
(261)
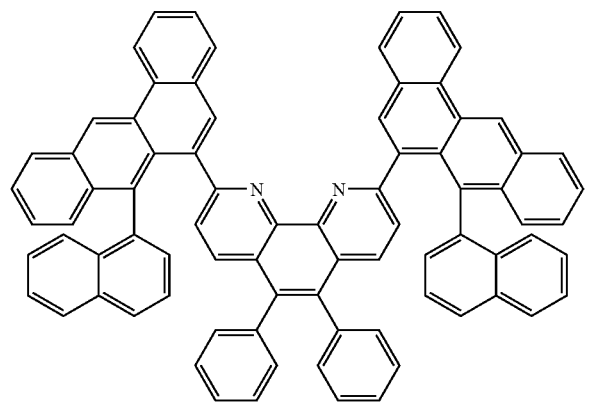
(262)
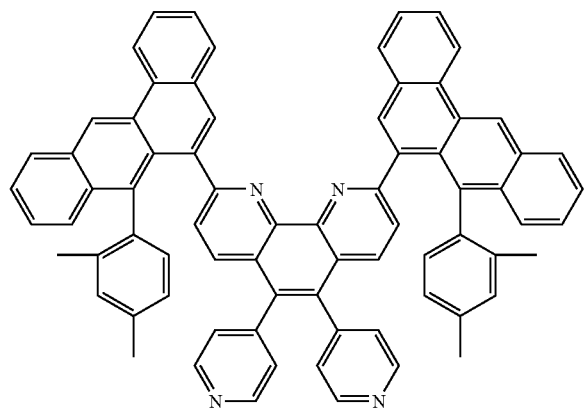
(263)
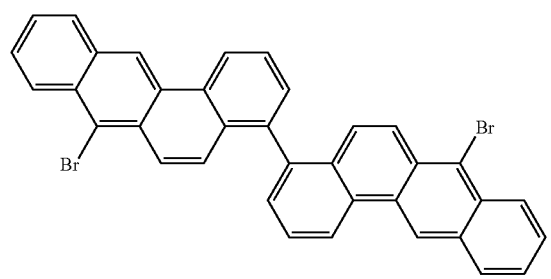
(264)
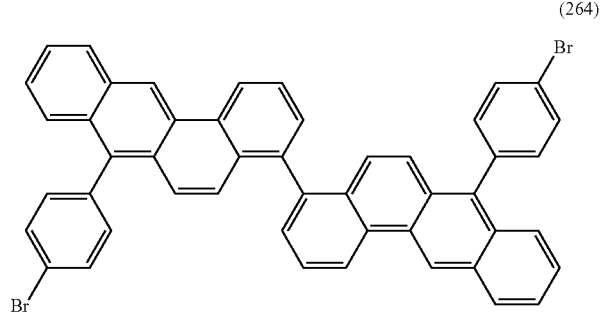
(265)
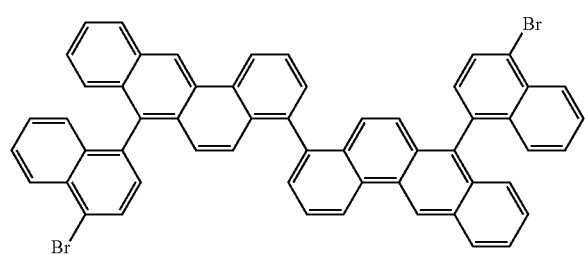
(266)
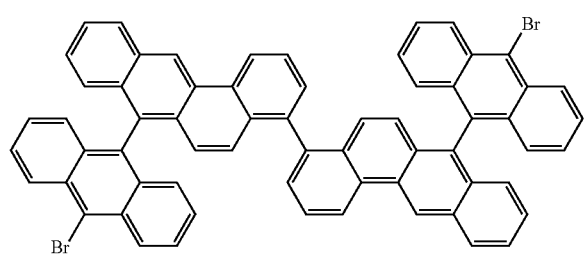

-continued
(267)
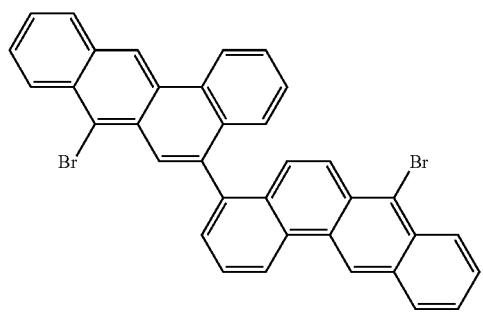
(268)
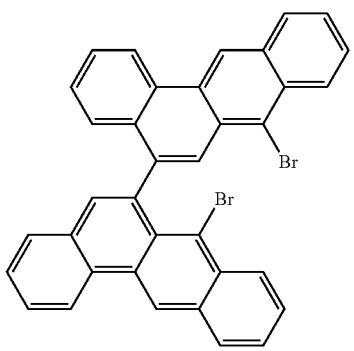
(269)
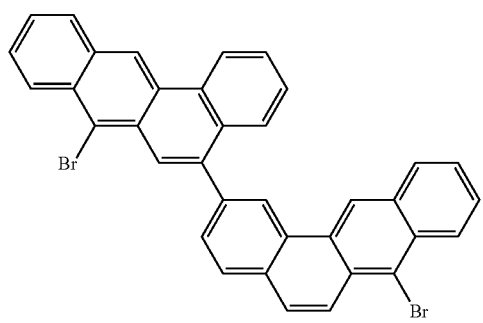
(270)
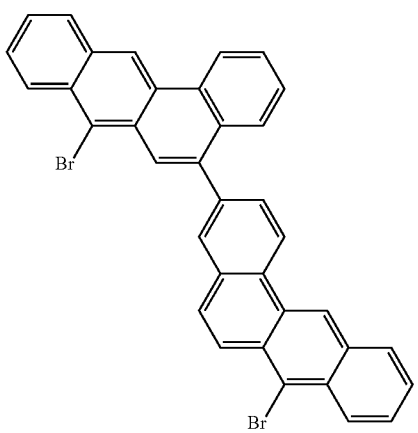
(271)
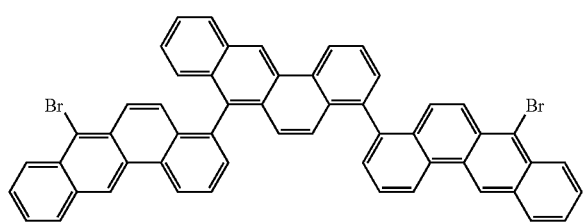
(272)
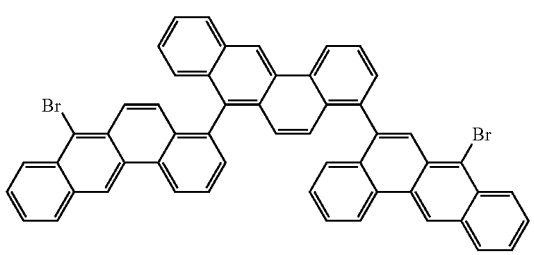
(273)
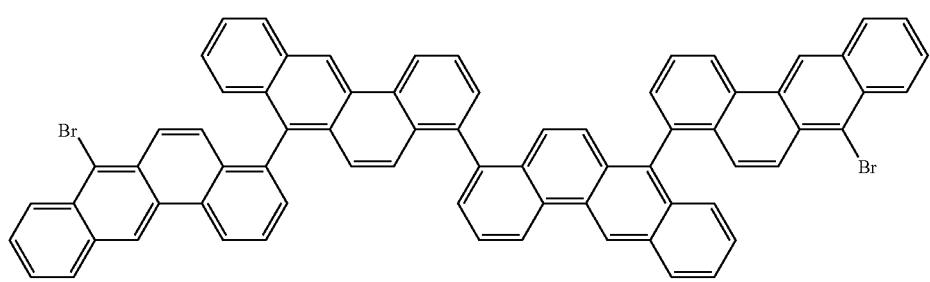
(274)
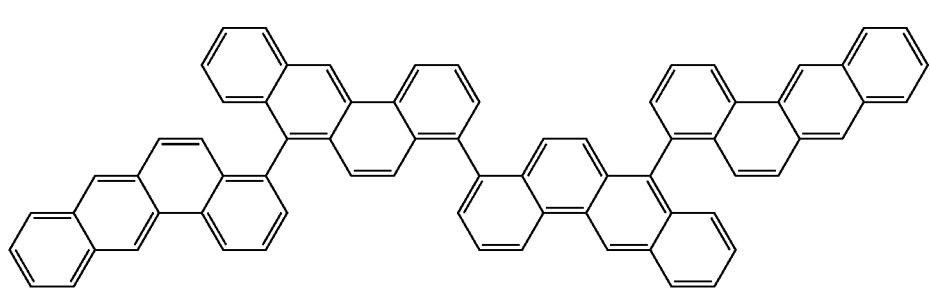

(275)

(276)

(277)

(278)

(279)
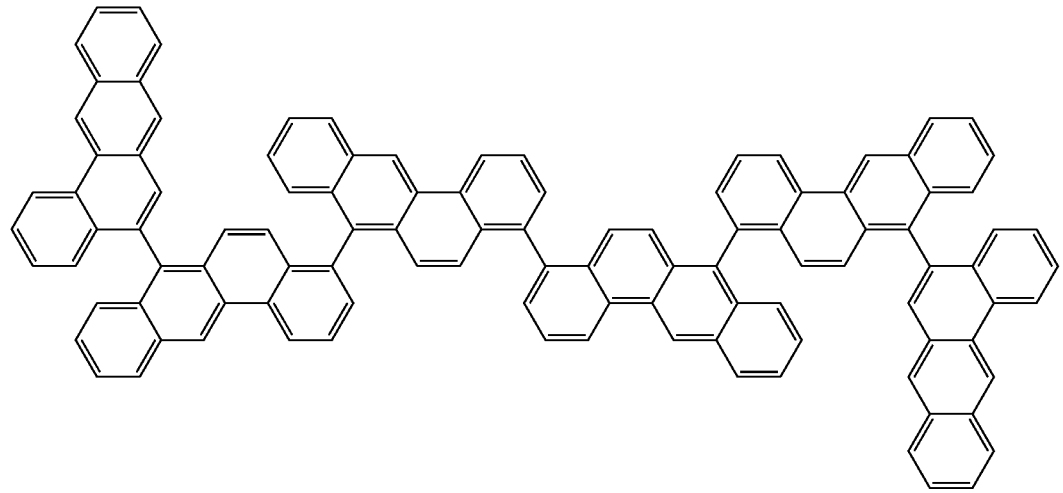
(280)
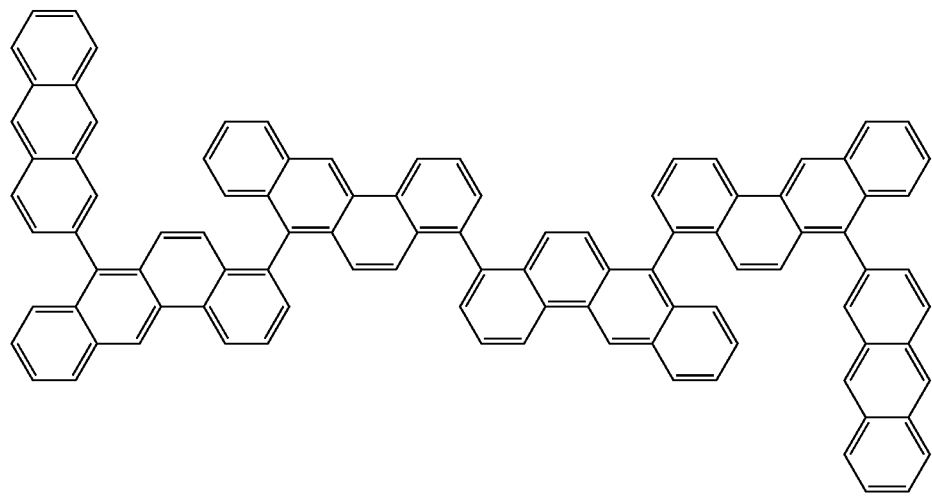
(281)
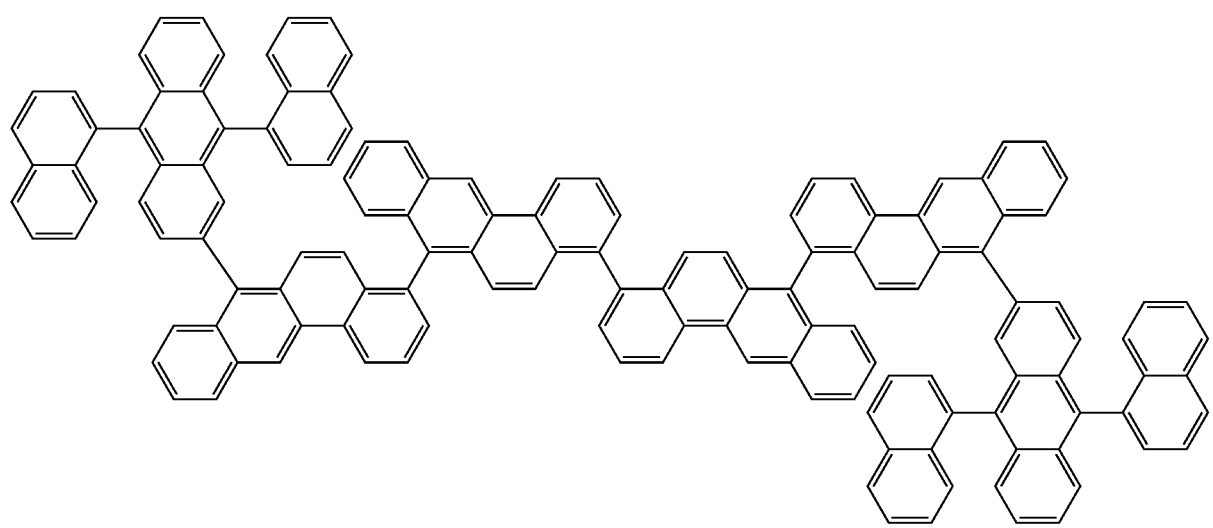

(282)
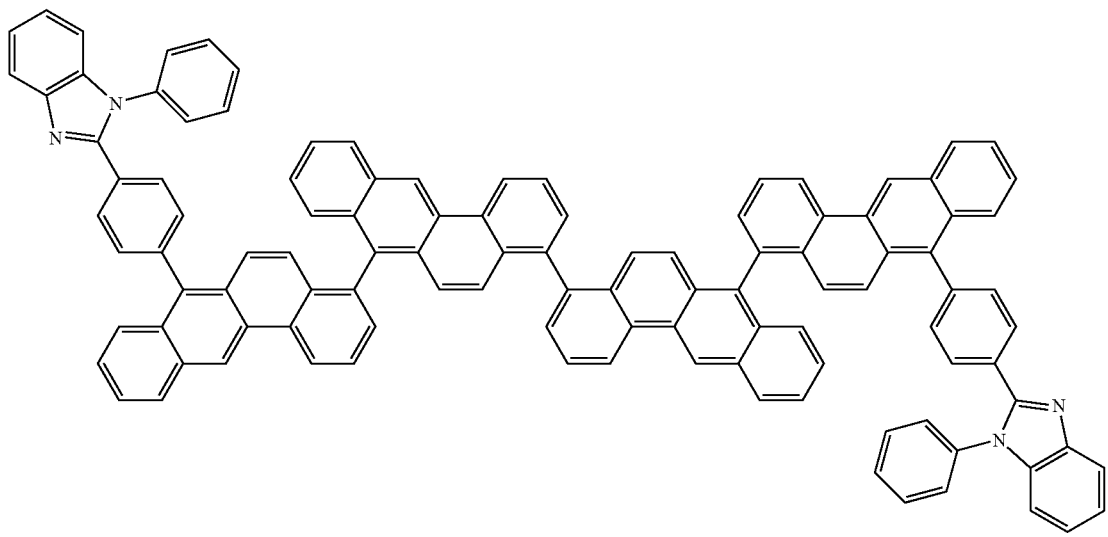
(283)
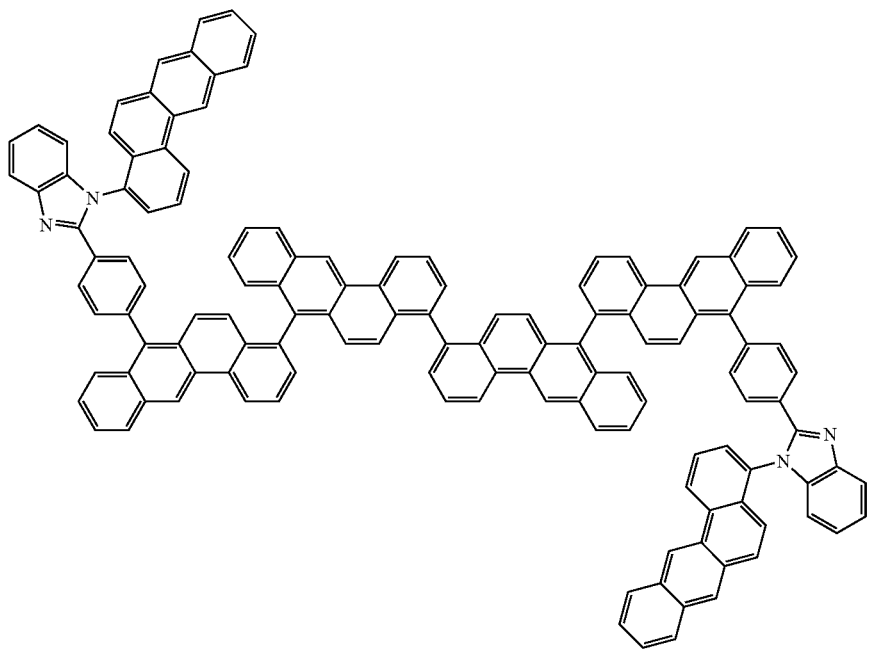
(284)
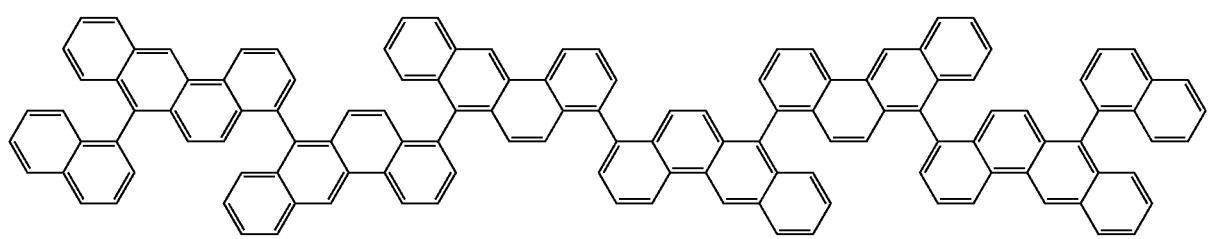

(285)
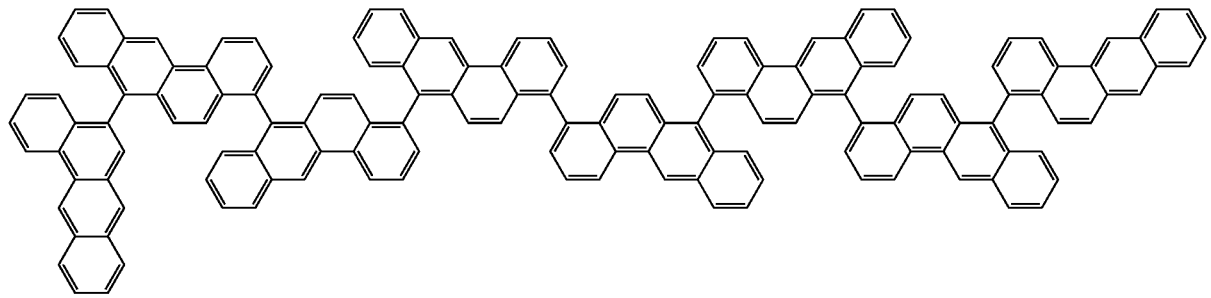
(286)
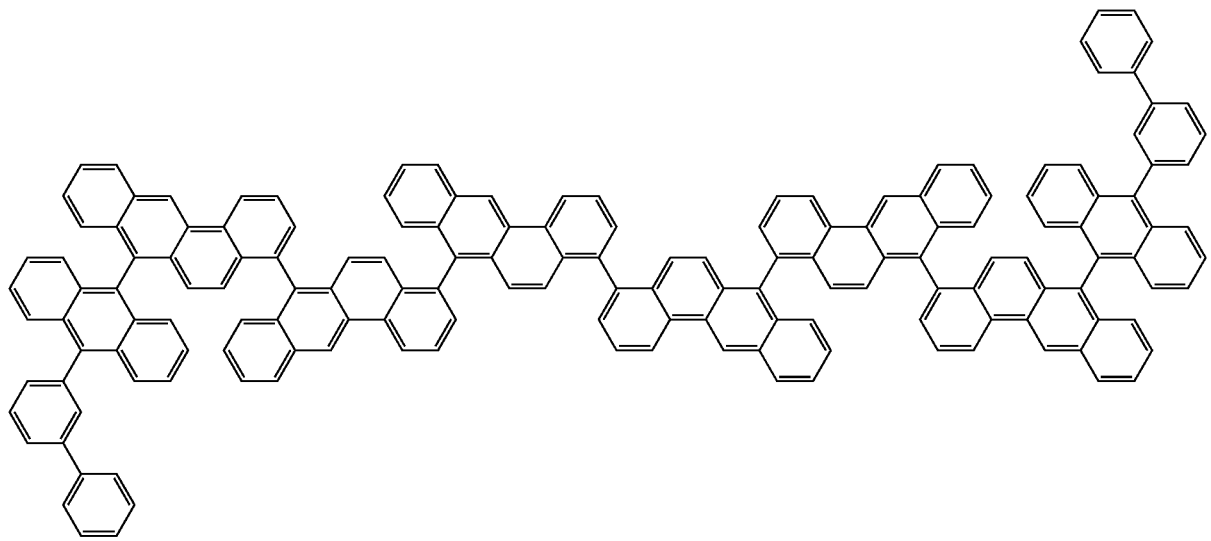
(287)
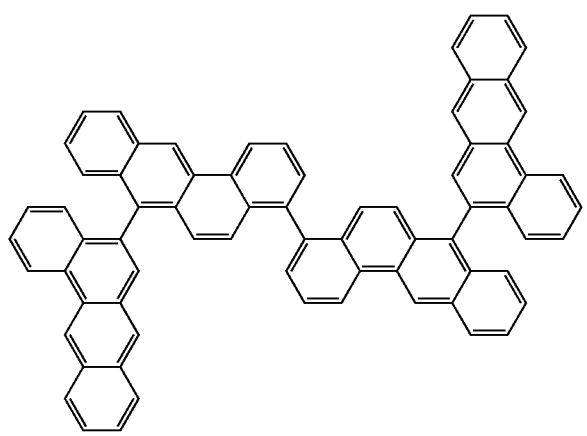
(288)
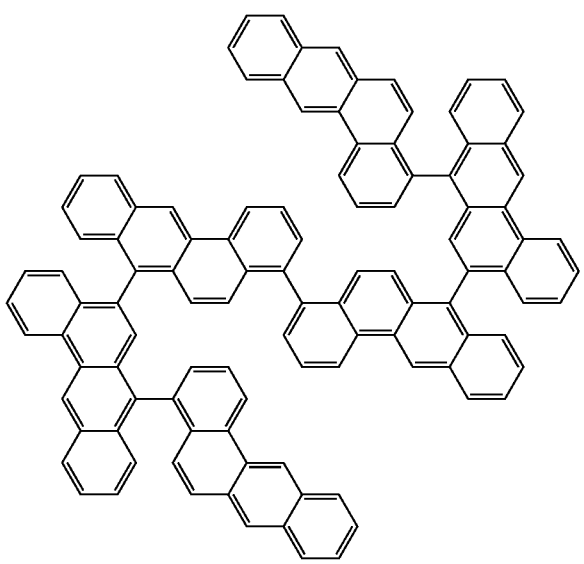

-continued
(289)
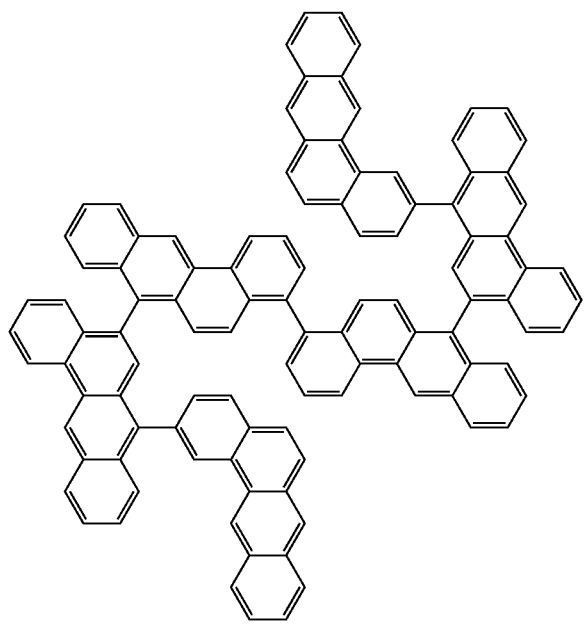
(290)
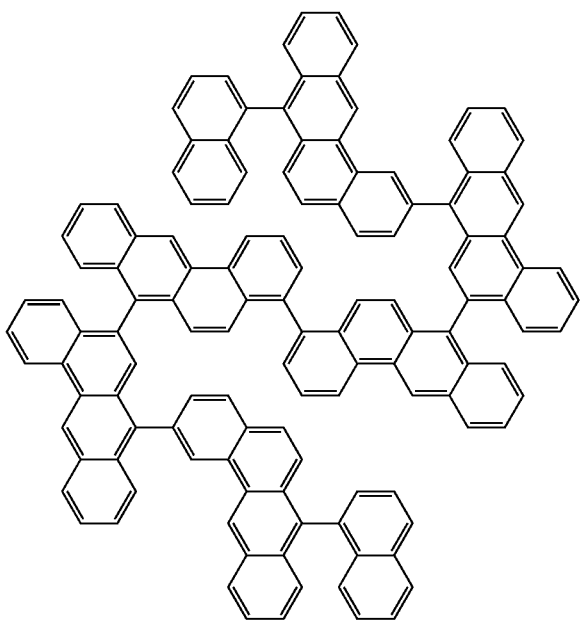
(291)
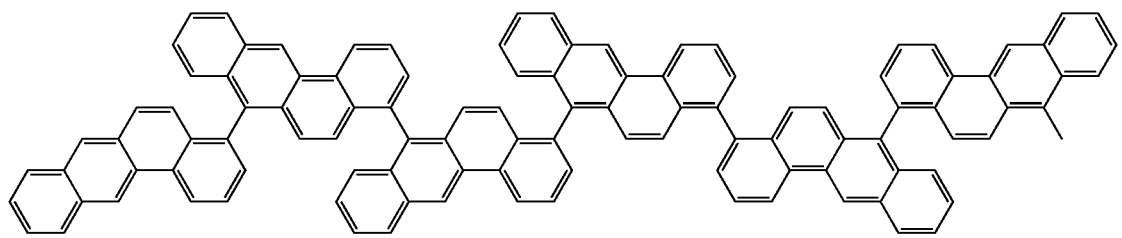
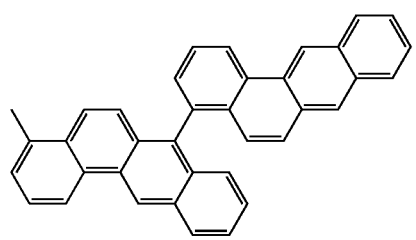
(292)
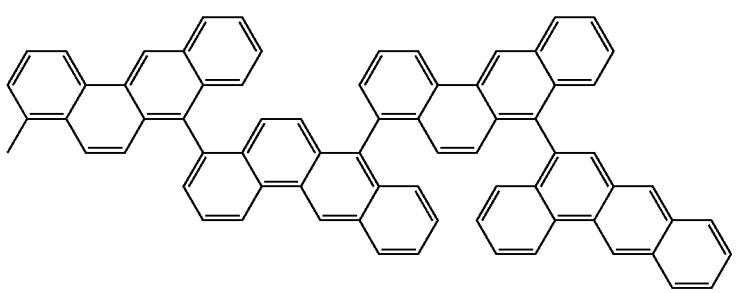

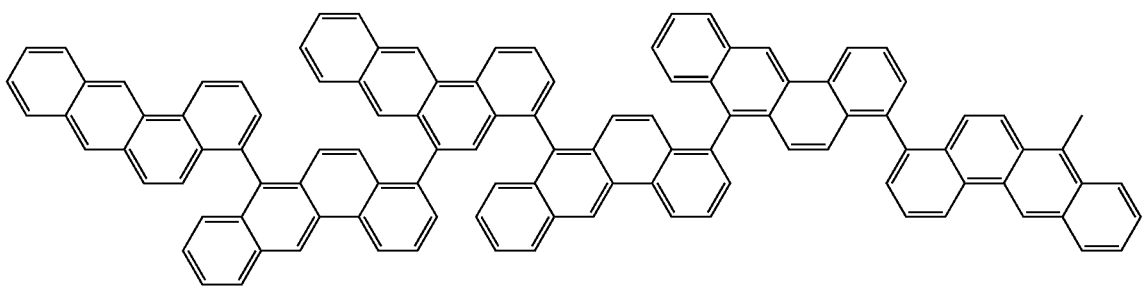
(293)
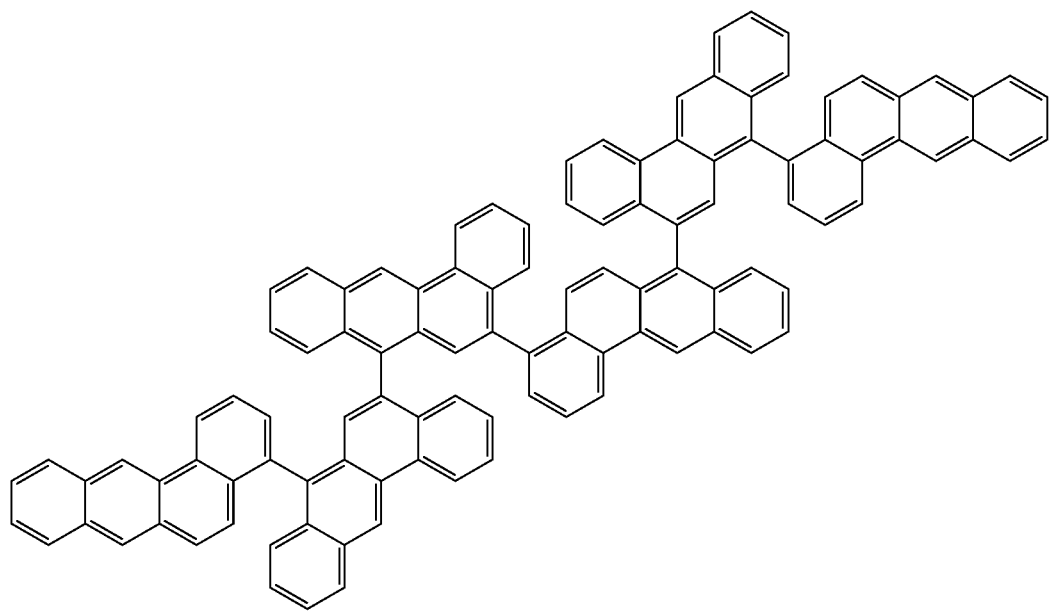
(294)
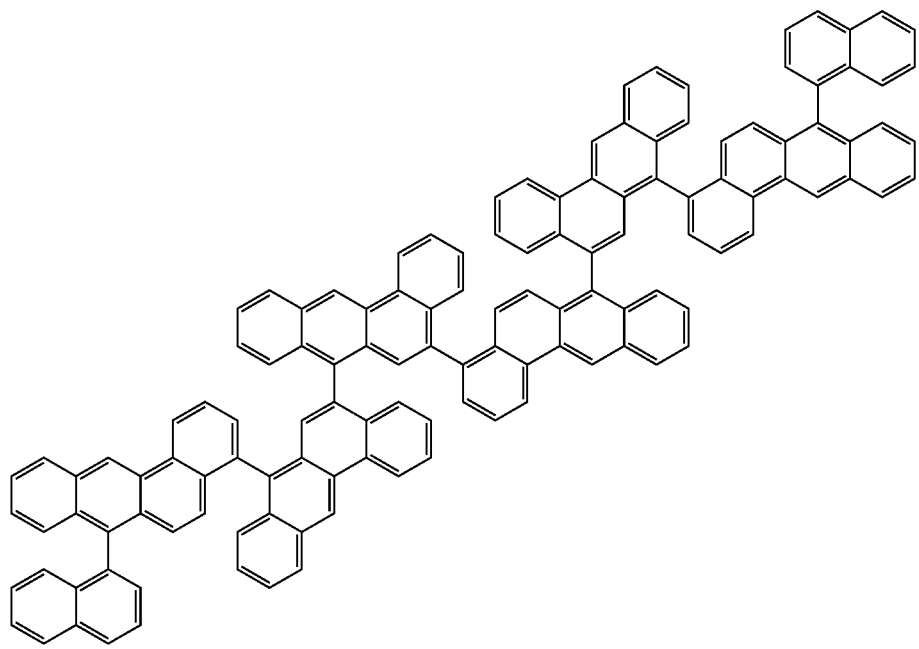

(295)
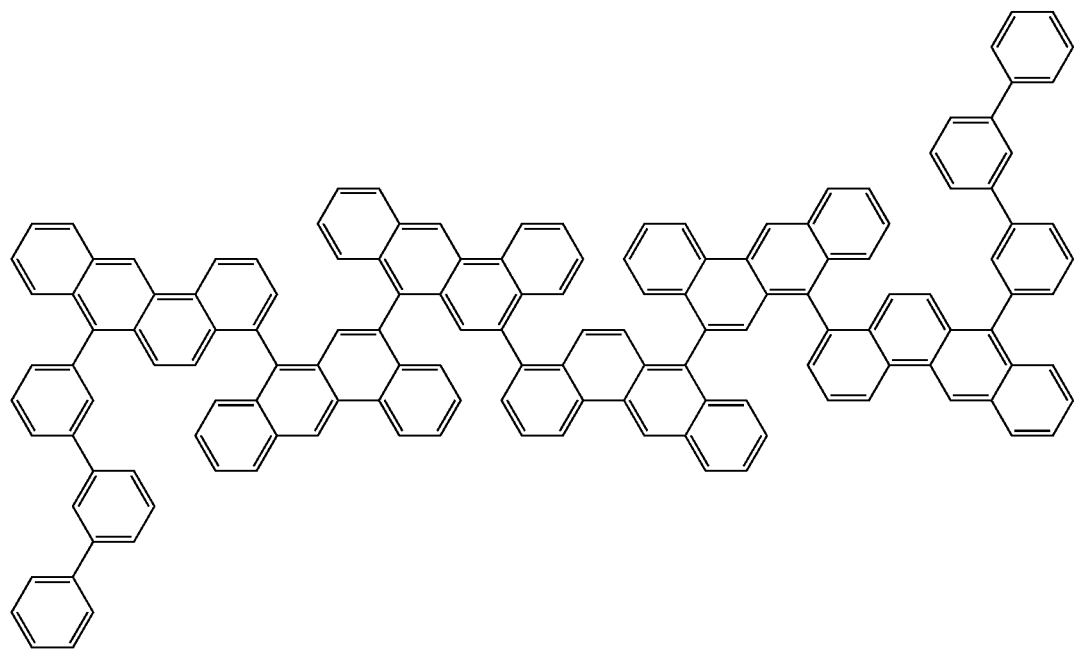
(296)
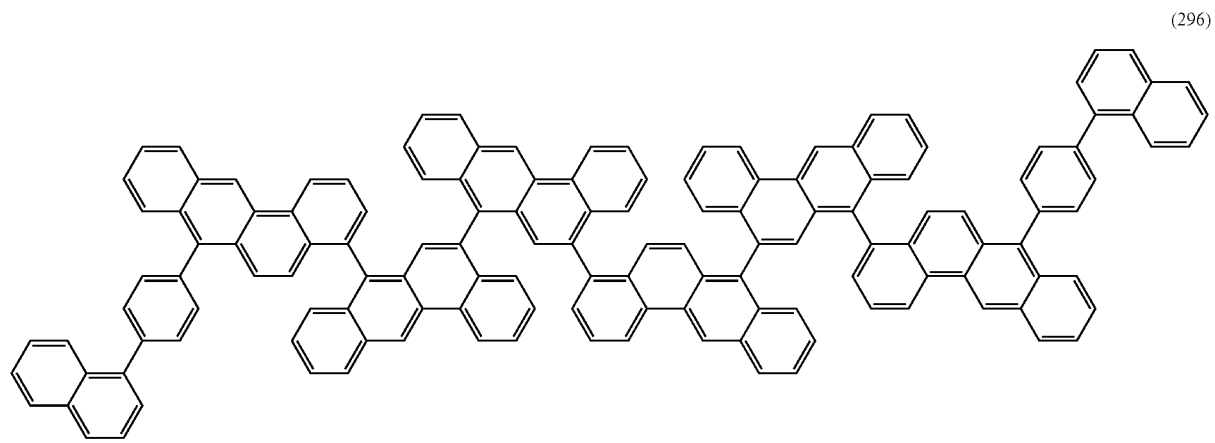
(297)
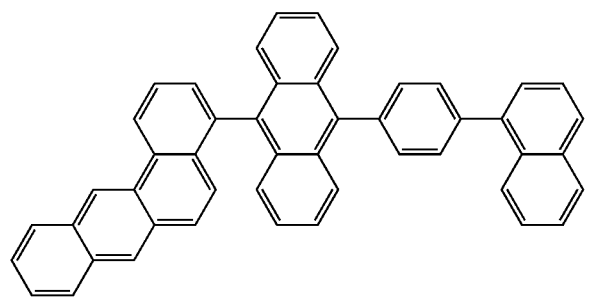
(298)
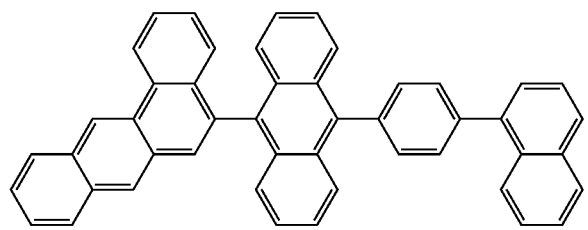
(299)
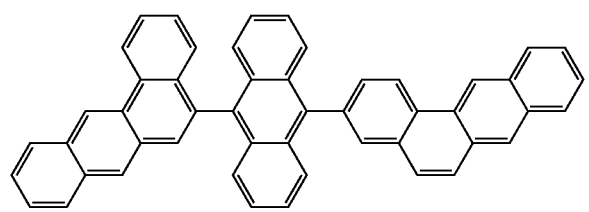
(300)
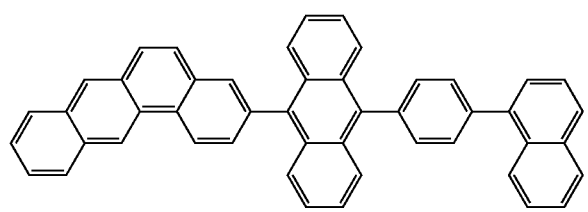

-continued
(301)
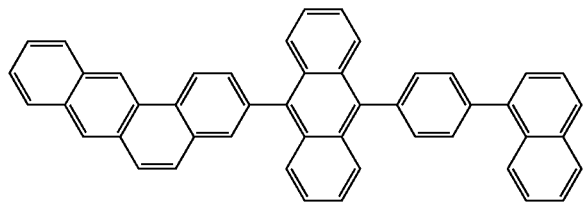
(302)
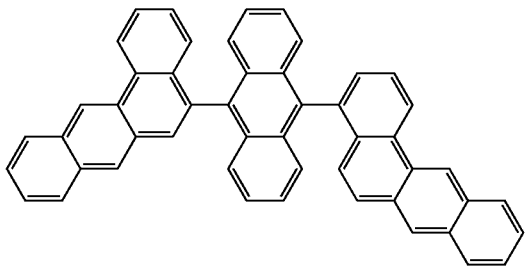
(303)
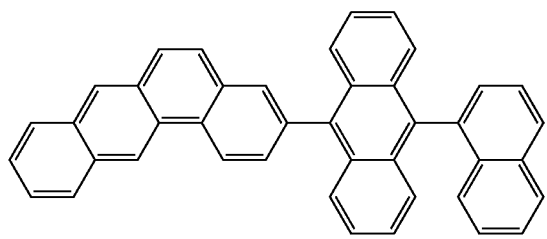
(304)
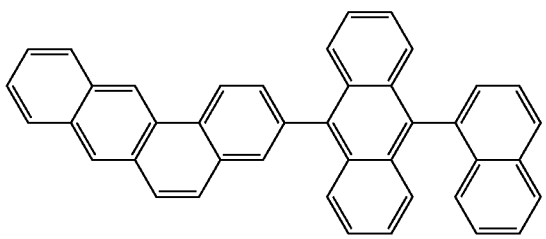
(305)
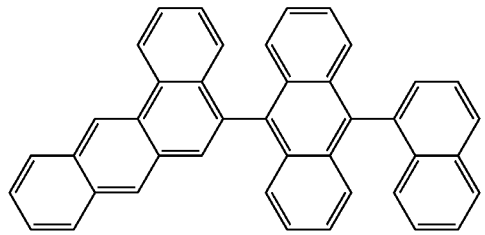
(306)
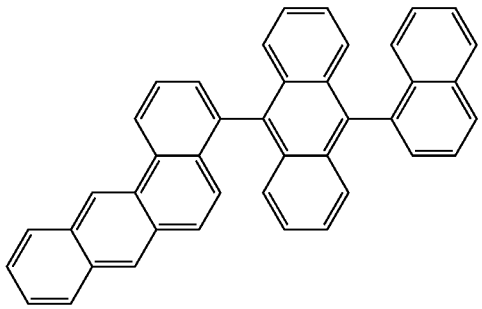
(307)
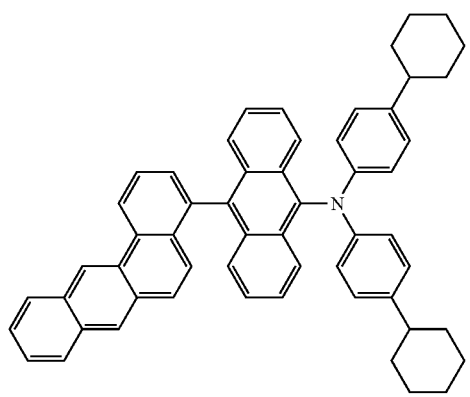
(308)
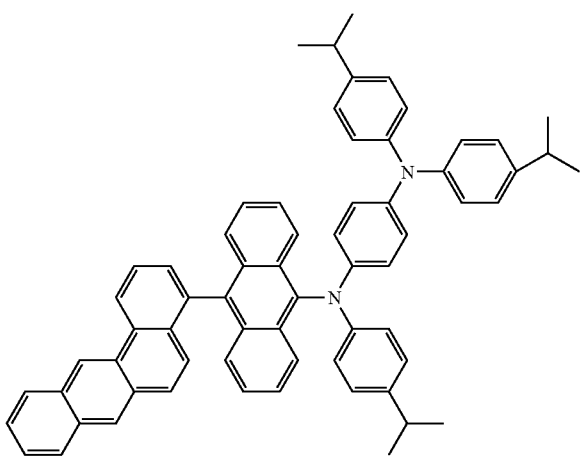

-continued
(309)
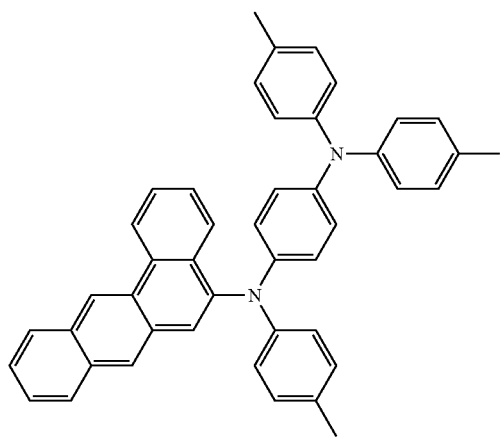
(310)
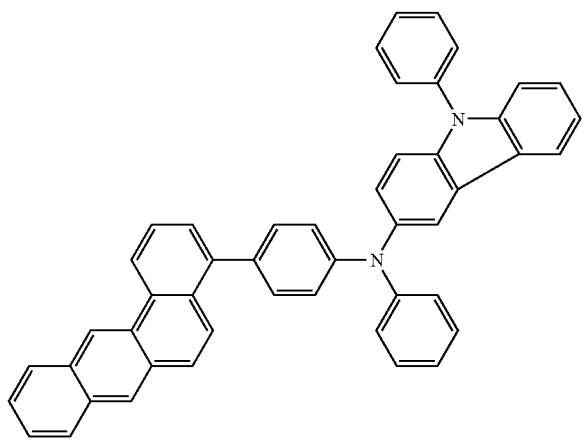
(311)
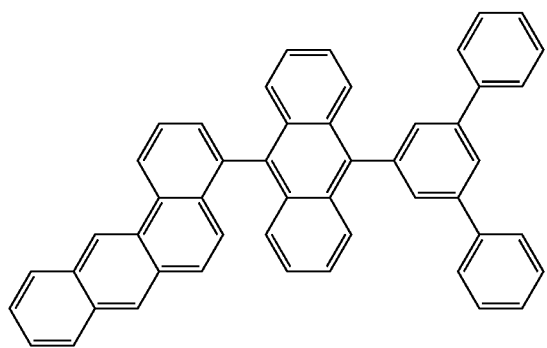
(312)
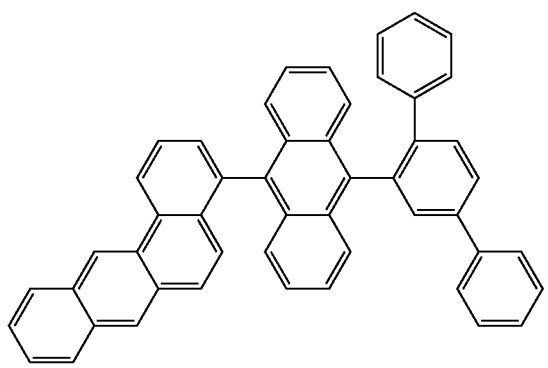
(313)
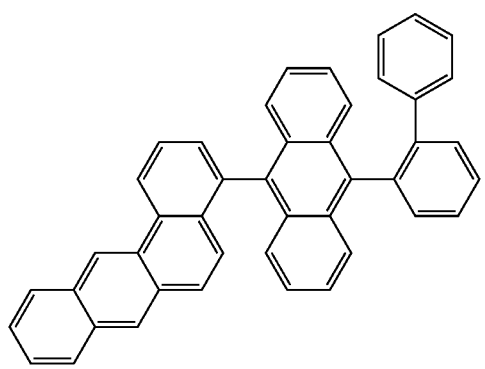
(314)
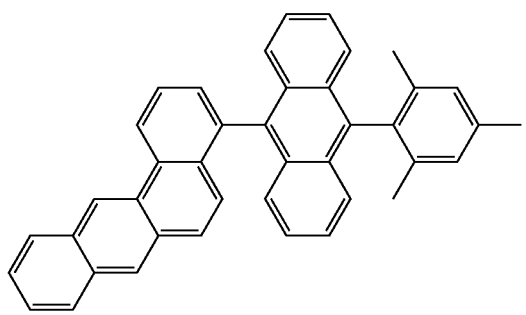
(315)
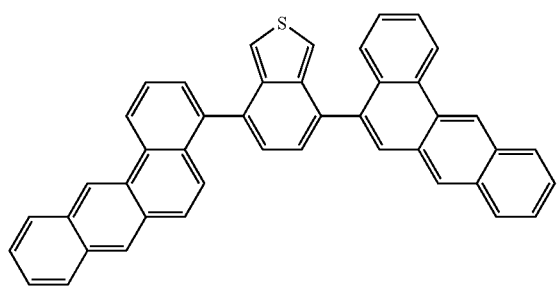
(316)
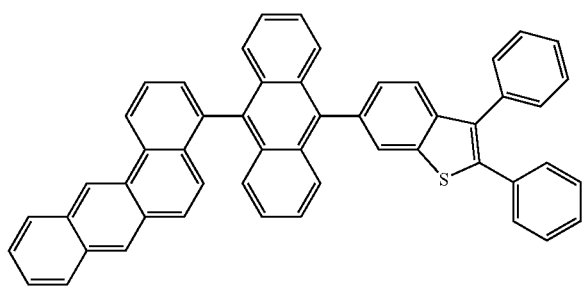

-continued
(317)
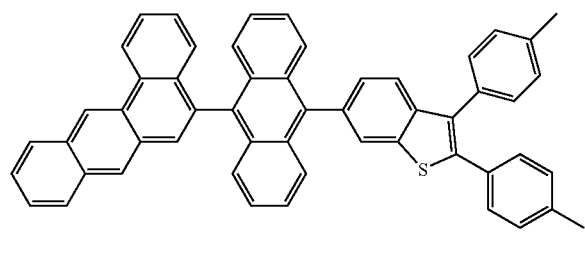
(318)
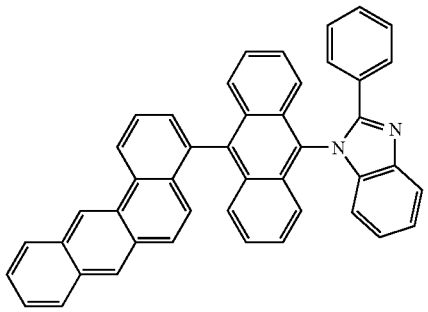
(319)
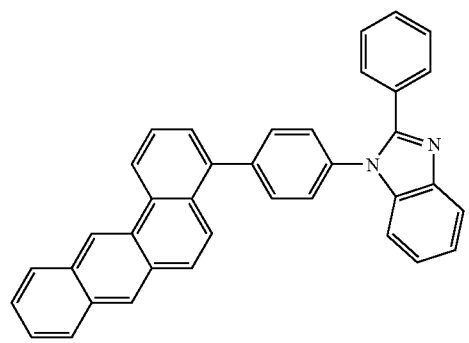
(320)
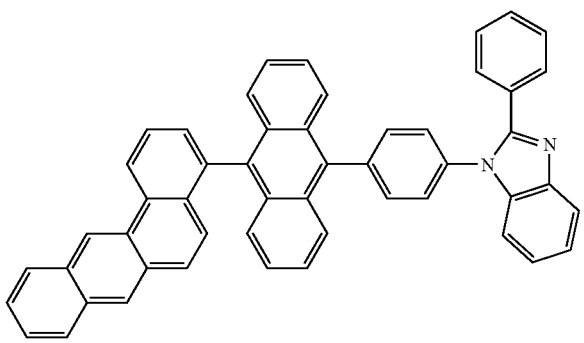
(321)
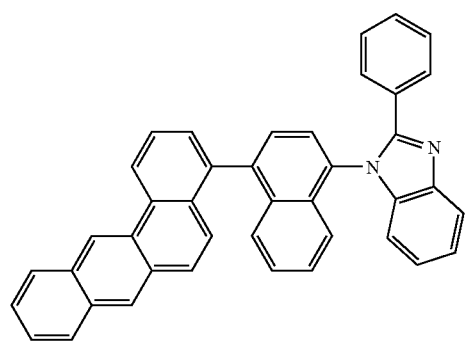
(322)
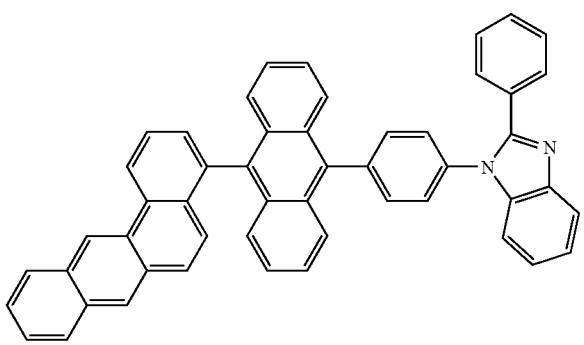
(323)
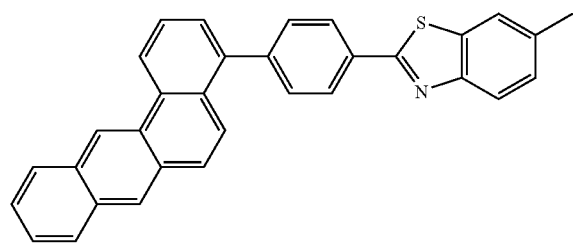
(324)
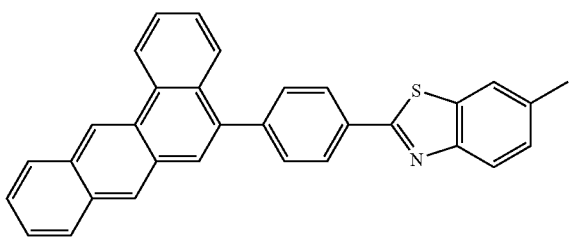

-continued
(325)
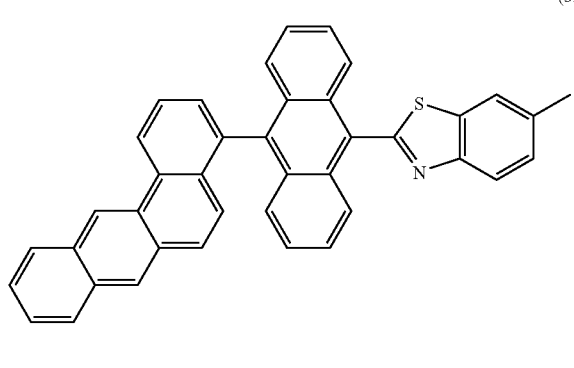
(326)
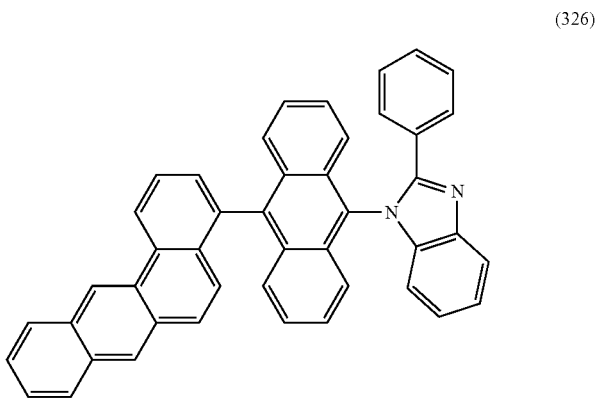
(327)
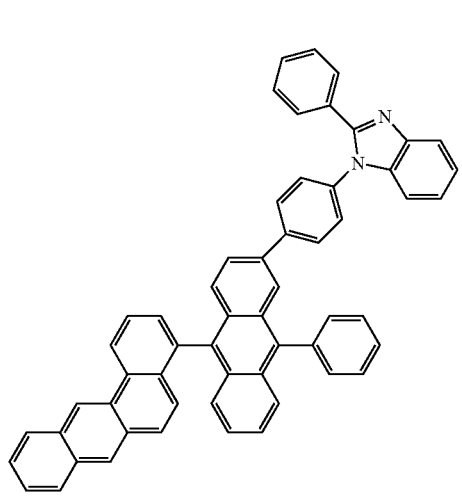
(328)
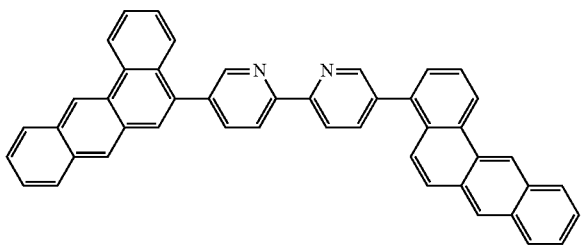
(329)
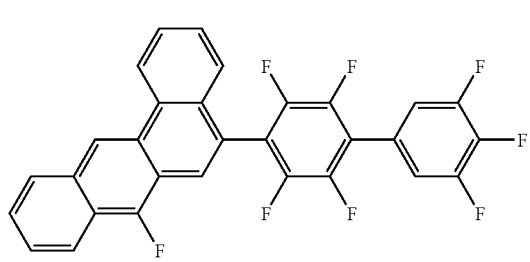
(330)
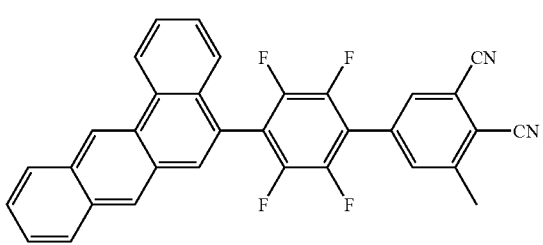
(331)
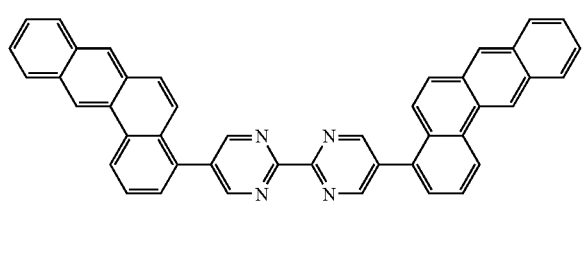
(332)
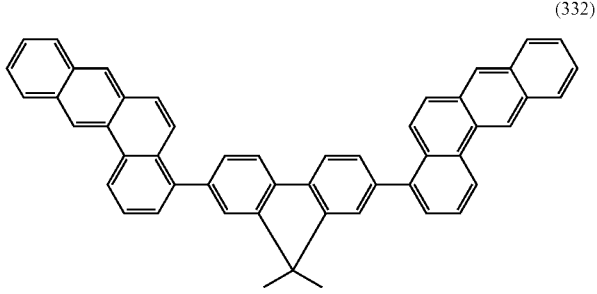

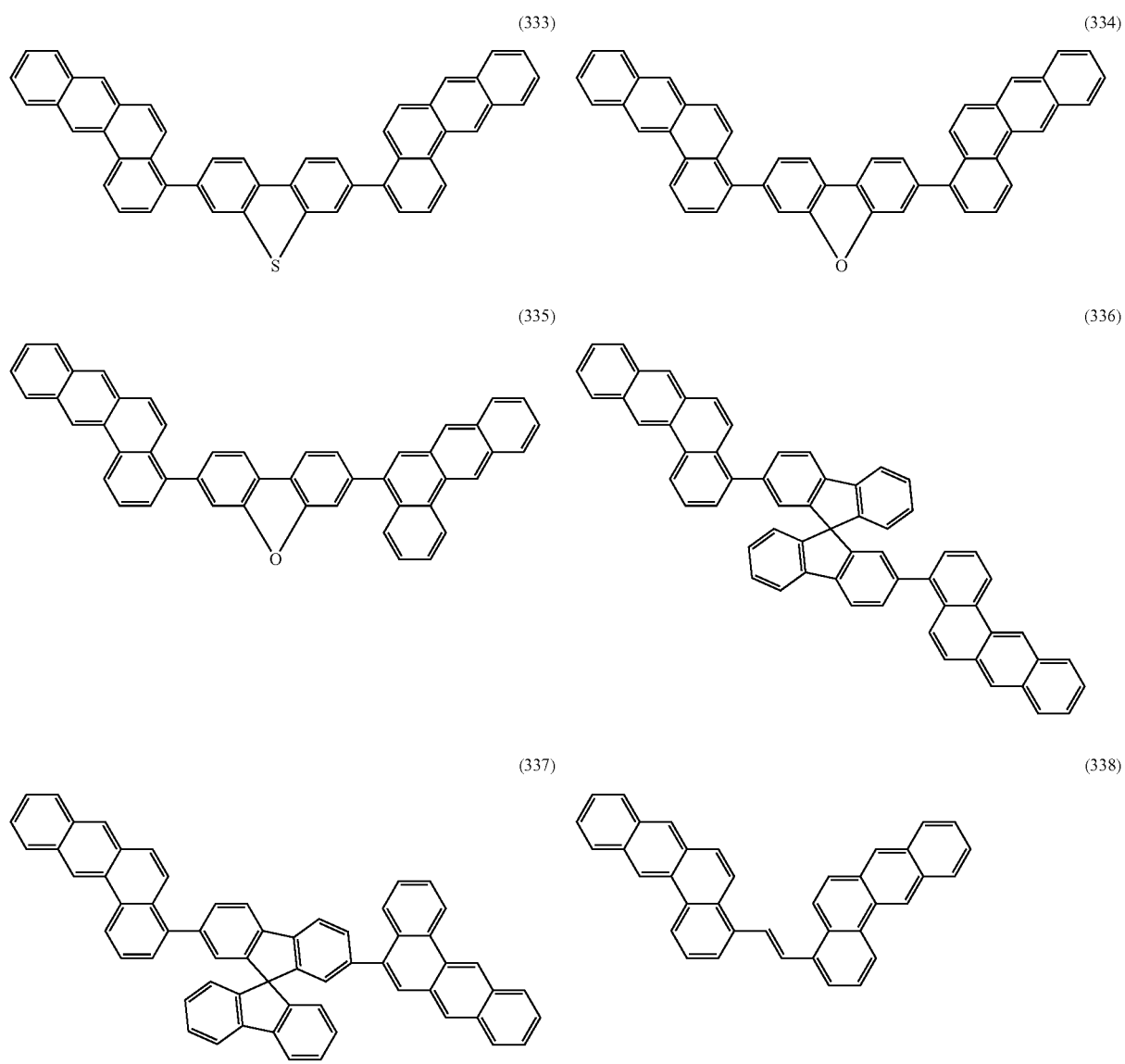

The compounds of the formula (1) according to the invention can be prepared by the synthetic steps known in general terms to the person skilled in the art. The starting compound can be, for example, the corresponding bromobenz[a]anthracenes, the synthesis of which is known (2- and 3-bromobenz[a]anthracene: Hallmark et a, *J. Lab. Comp. Radiopharm.* 1981, 18(3), 331; 4-bromobenz[a]anthracene: Badgar et al., *J. Chem. Soc.* 1949, 799; 5-bromobenz[a]anthracene: Newman et al., *J. Org. Chem.* 1982, 47(15), 2837). The benz[a]anthracenes which are substituted by corresponding leaving groups, such as chlorine, iodine, triflate or tosylate, can likewise serve as starting compounds. Substituted or unsubstituted 5-bromobenz[a]anthracene can alternatively also be obtained from 2-bromo-benzaldehyde and 1-chloromethyl-naphthalene in accordance with Scheme 1. R in Scheme 1 stands for one or more radicals as defined for formula (1). Instead of lithiation, reaction with another reactive metal, for example magnesium, can also take place in the first step. The Suzuki coupling in the first step is carried out under standard conditions, as known to the person skilled in the art of organic chemistry, for example using Pd(PPh$_3$)$_4$ in toluene/water with addition of a base at elevated temperature. The bromination in the second step can be carried out, for example, using elemental bromine or using NBS. The ring closure in the third step can be carried out, for example, by the action of polyphosphoric acid.

Scheme 1

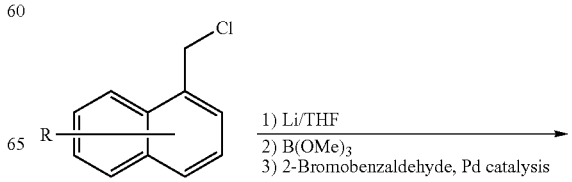

1) Li/THF
2) B(OMe)$_3$
3) 2-Bromobenzaldehyde, Pd catalysis

-continued

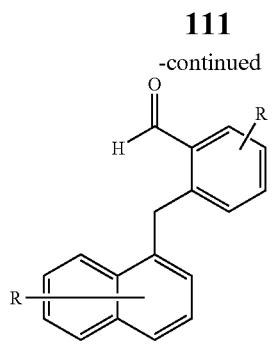

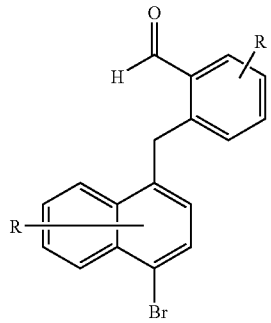

-continued

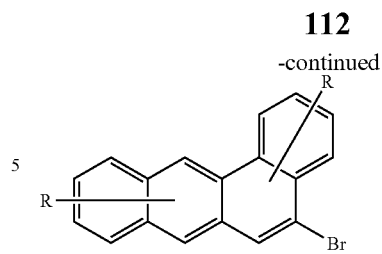

Further access to substituted benz[a]anthracene consists in the coupling of naphthalene-2-boronic acid to 2-bromophenylacetylene. The acetylene obtained in this way can either be reacted directly in a ring-closure reaction or can be cyclised after halogenation or can be reacted with an aromatic compound in a Sonogashira coupling and subsequently cyclised. The ring closure of the acetylene is in each case carried out using an electrophile. The compounds in Scheme 2 may also be substituted by one or more radicals R, where R has the same meaning as described above under formula (1). Ar denotes an aromatic or heteroaromatic ring system. The Suzuki couplings and the Sonogashira coupling are carried out under standard conditions, as known to the person skilled in the art of organic synthesis. Preferred electrophiles for the ring-closure reaction are strong acids, such as $CF_3COOH$, indium halides, such as $InCl_3$ or $InBr_3$, platinum halides, such as $PtCl_2$, or interhalogen compounds, such as I—Cl.

Scheme 2

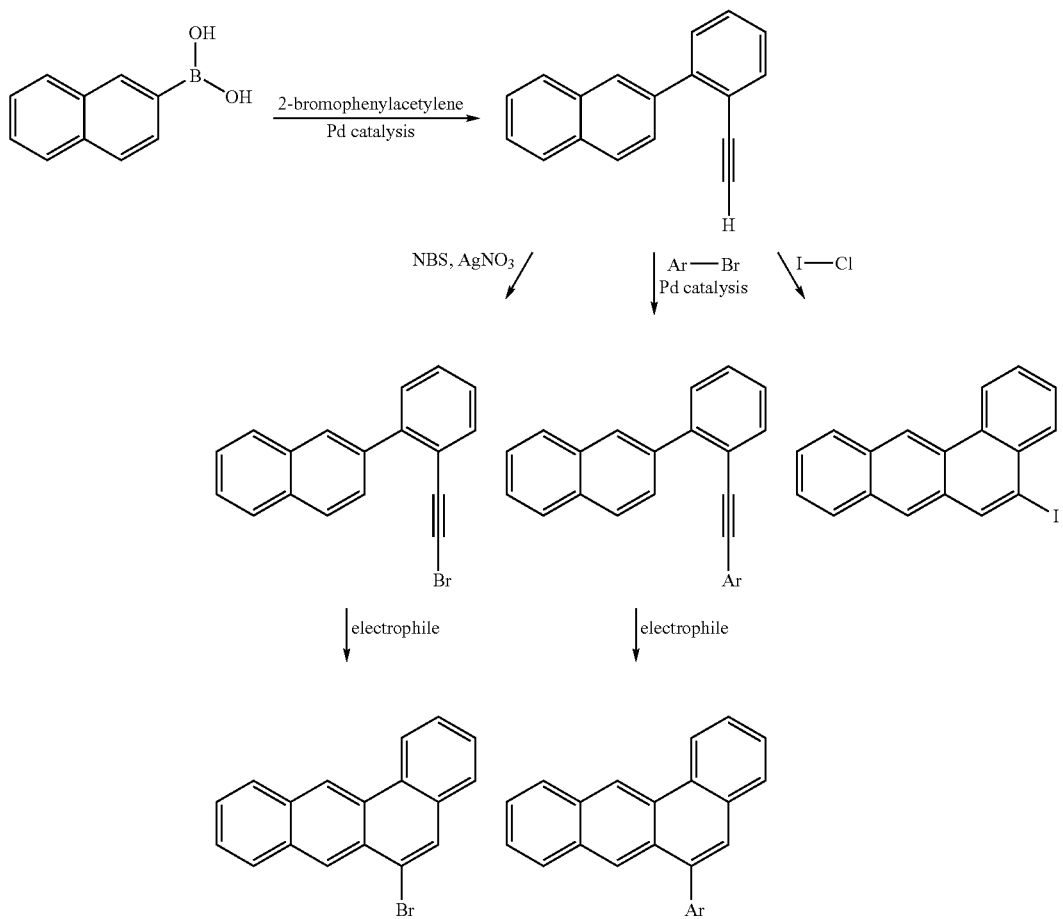

The present invention furthermore relates to a process for the preparation of optionally substituted 6-arylbenz[a]anthracene by reaction of an optionally substituted 2-(2'-arylacetylene)phenylnaphthalene with an electrophile. Any substituents present are defined analogously to the radical R defined above.

The boronic acids or boronic acid derivatives derived from these compounds can be obtained by transmetallation, for example using n-butyl-lithium in THF at −78° C., followed by reaction of the lithiobenz[a]anthracene formed as an intermediate with trimethyl borate, as shown by way of example in Scheme 3 with reference to the example of 4-bromobenz[a]-anthracene, optionally followed by esterification. The lithiated compounds can furthermore be converted into ketones by reaction with electrophiles, such as benzonitrile, followed by acidic hydrolysis or into phosphine oxides using chlorodiarylphosphines followed by oxidation. Reaction of the lithiated compound with other electrophiles is also possible.

Scheme 3

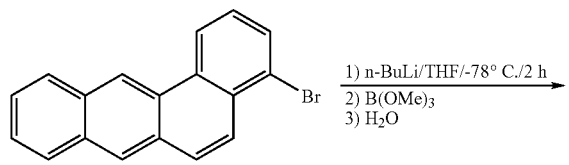

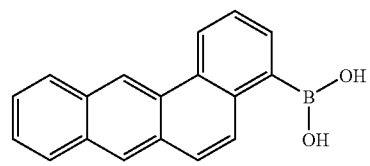

The compounds in Scheme 3 may also be substituted by one or more radicals R, where R has the same meaning as described above under formula (1). The Suzuki coupling of the boronic acids or boronic acid derivatives to aryl bromides results in a large class of different aromatic and heteroaromatic compounds. This is shown by way of example in Schemes 4 a) to e), starting from benz[a]anthracene-4-boronic acid, but also applies in the same way to the other substitution patterns. Furthermore, all structures may also be substituted by one or more radicals R, where R has the same meaning as described above under formula (1).

Scheme 4 a)

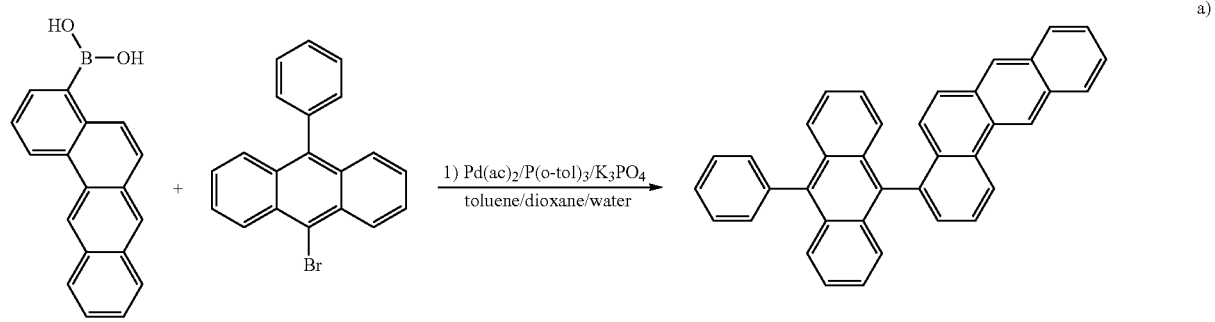

b)

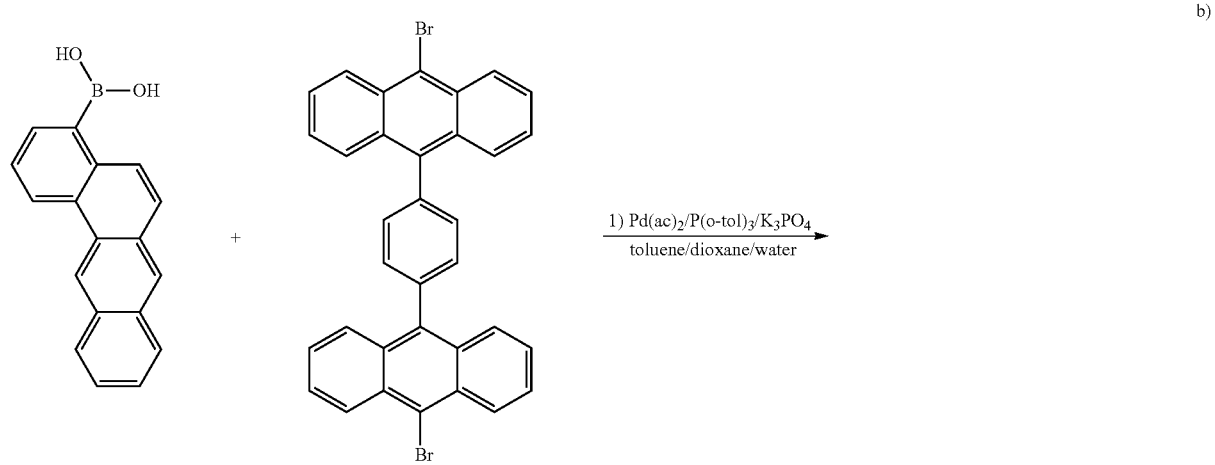

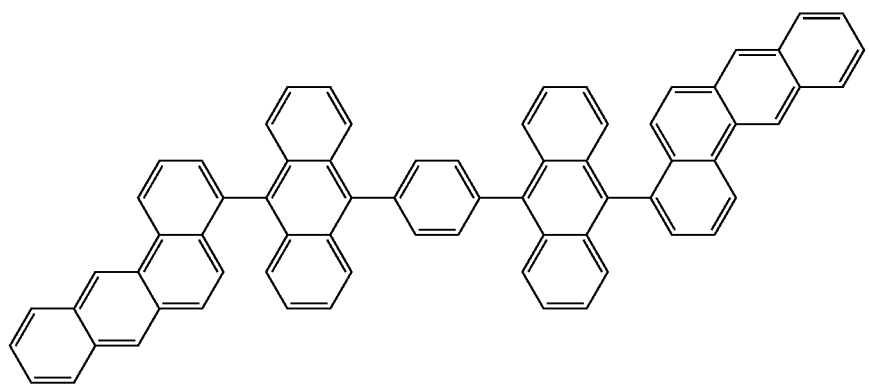
c)
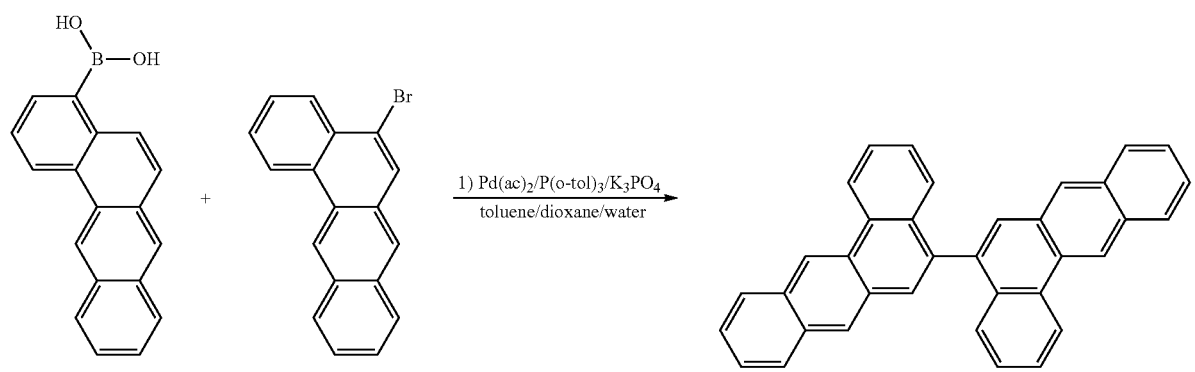
d)
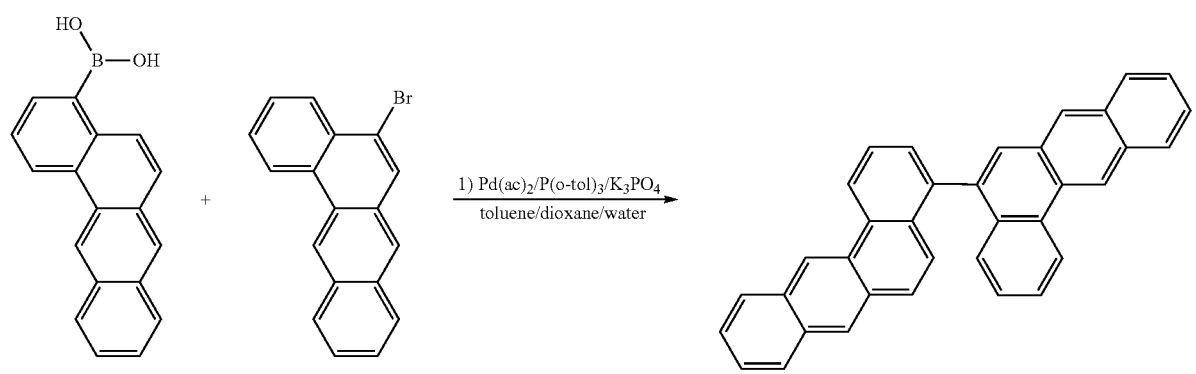
e)
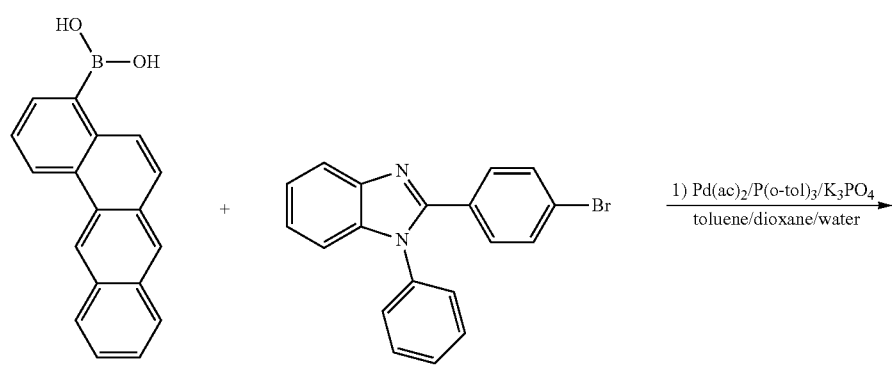

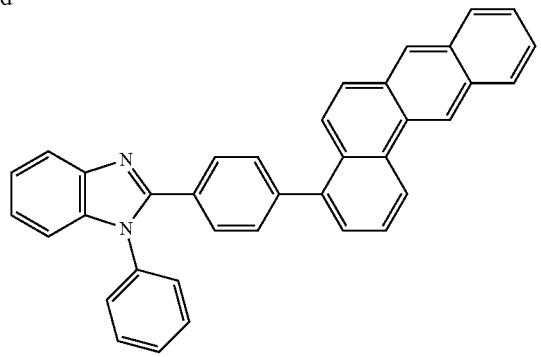

Alternatively, the bromobenz[a]anthraquinones (synthesis in accordance with Newman et al., *J. Org. Chem.* 1983, 48, 2926-8; Cho et al., *J. Org. Chem.* 1987, 52, 2668-78; Becker et al., *J. Phys. Chem.* 1993, 97, 344-9) can firstly be coupled and then reduced to the corresponding hydrocarbons, as shown by way of example for 5-bromobenz[a]anthraquinone in Scheme 5. Instead of simple aromatisation, the corresponding 7,12-substituted benz[a]anthracene derivatives can also be synthesised here by the addition reaction of an organometallic reagent, for example an organolithium compound or a Grignard compound, followed by aromatisation.

The compounds in Scheme 5 may also be substituted by one or more radicals R, where R has the same meaning as described above under formula (1).

The palladium-promoted amination of the bromides by the Hartwig-Buchwald method gives the corresponding aminated benz[a]anthracenes (Scheme 6). Amination in the other positions of the benz[a]anthracene is possible correspondingly. A corresponding reaction with other leaving groups, such as chlorine, iodine, triflate, tosylate, etc., is possible.

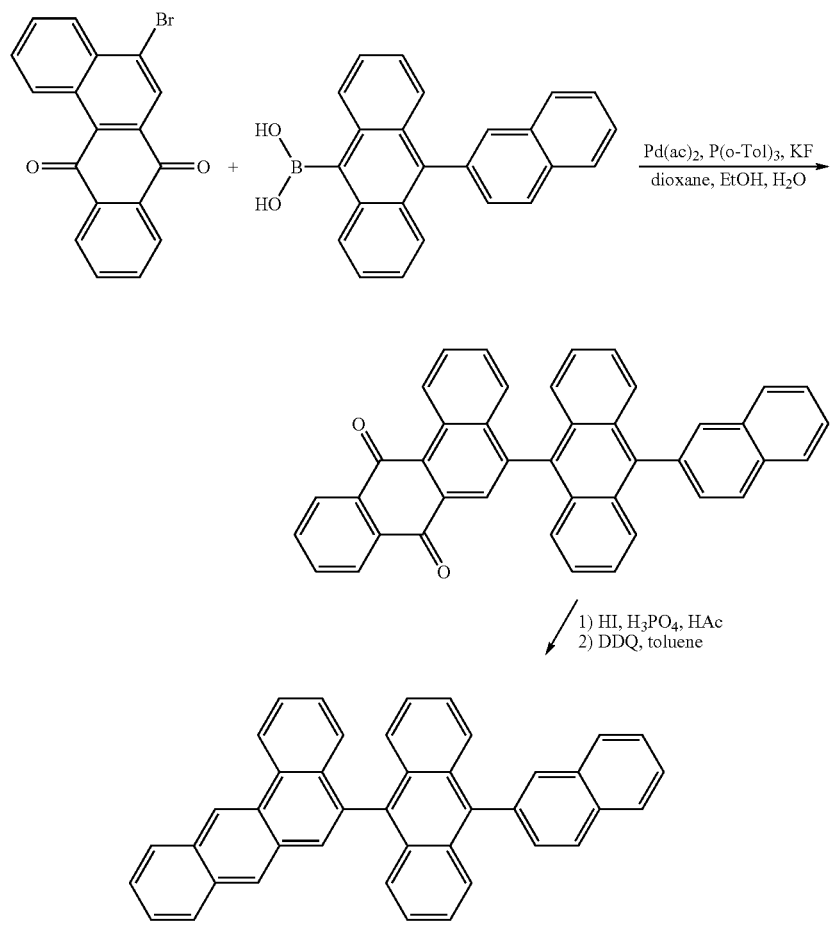

Scheme 5

Scheme 6

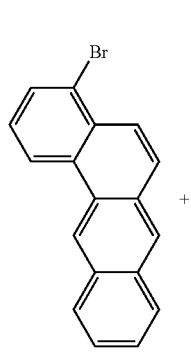

+

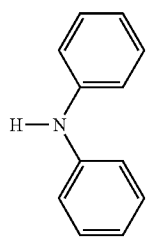

Pd(ac)2/ClP(tert-Bu)₂/NaO-tert-Bu
────────────────────────────────→
toluene

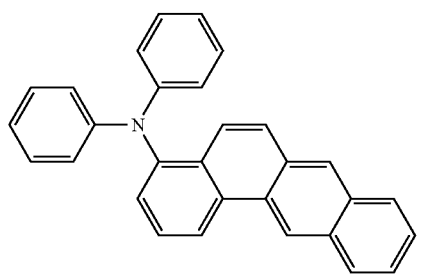

The compounds in Scheme 6 may also be substituted by one or more radicals R, where R has the same meaning as described above under formula (1).

The invention still furthermore relates to a process for the preparation of compounds of the formula (1) by coupling a benz[a]anthracene which is substituted by a reactive leaving group, in particular chlorine, bromine, iodine, triflate, tosylate, boronic acid or boronic acid ester, to a functionalised aromatic compound or to a mono- or disubstituted amine. The reactive leaving group is preferably bromine. Suitable coupling reactions between the skeleton of the formula (1) and the aryl substituent are, in particular, transition-metal-catalysed coupling reactions, in particular Suzuki coupling with palladium catalysis, so that coupling of a boronic acid derivative to a halogen derivative is particularly suitable here. A suitable coupling reaction to a mono- or disubstituted amine is, in particular, palladium-catalysed coupling by the Hartwig-Buchwald method. The reaction conditions for such reactions are known in general terms to the person skilled in the art of organic synthesis.

The boronic acids can furthermore be converted into boronic acid esters by reaction with diols, oligools and polyols or into anhydrides by boiling in toluene on a water separator (Scheme 7), where the reaction for positions 2, 3, 5 and 6 on the benz[a]anthracene proceeds correspondingly.

Scheme 7

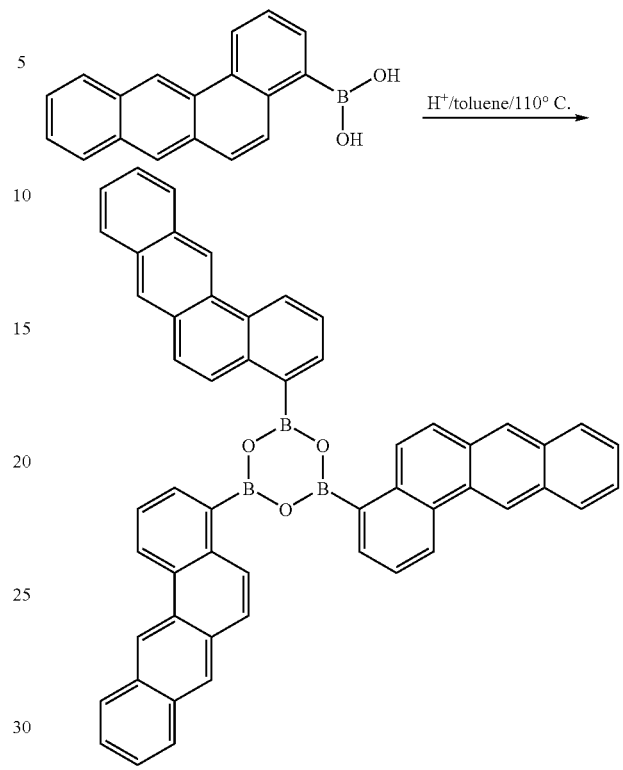

The compounds in Scheme 7 may also be substituted by one or more radicals R, where R has the same meaning as described above under formula (1).

The invention furthermore relates to compounds of the following formula (34), which represent an important intermediate in the synthesis of compounds of the formula (1)

Formula (34)

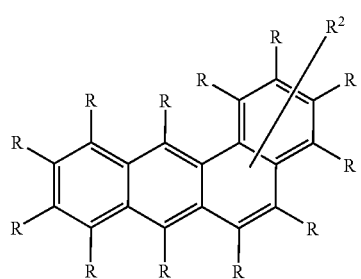

where R, $R^1$ and $Ar^1$ have the same meaning as described above for compounds of the formula (1), and $R^2$ is bonded in position 2, 3, 4, 5 or 6 of the benz[a]anthracene and correspondingly no group R is bonded at this position, and furthermore:

$R^2$ stands for $B(OR^1)_2$ or $B(OAr^1)_2$.

It is furthermore also possible to employ the boronic acid derivatives of the formula (20) directly as active compound in organic electronic devices, as described in general terms in WO 06/117052.

The compounds according to the invention described above, in particular compounds which are substituted by reactive leaving groups, such as bromine, iodine, boronic acid or boronic acid ester, can be used as monomers for the preparation of corresponding oligomers, dendrimers or polymers. The oligomerisation or polymerisation here preferably takes place via the halogen functionality or the boronic acid functionality.

The invention therefore furthermore relates to oligomers, polymers or dendrimers containing one or more compounds of the formula (1), where one or more radicals R or Ar or Y represent bonds from the compound of the formula (1) to the polymer, oligomer or dendrimer. Depending on the linking of the compound of the formula (1), the benz[a]anthracene unit therefore forms a side chain of the oligomer or polymer or is linked in the main chain. For the purposes of this invention, an oligomer is taken to mean a compound which contains at least three benz[a]anthracene units. The polymers, oligomers or dendrimers may be conjugated, partially conjugated or non-conjugated. The oligomers or polymers may be linear, branched or dendritic. In the structures linked in a linear manner, the units of the formula (1) may be linked directly to one another or linked to one another via a divalent group, for example via a substituted or unsubstituted alkylene group, via a heteroatom or via a divalent aromatic or heteroaromatic group. In branched and dendritic structures, three or more units of the formula (1) may, for example, be linked via a trivalent or polyvalent group, for example via a trivalent or polyvalent aromatic or heteroaromatic group, to give a branched or dendritic oligomer or polymer. The units of the formula (1) are preferably linked into the oligomer, dendrimer or polymer via positions 7 and 12 of the benz[a] anthracene. Linking via two positions to the group R or to the group Y is furthermore preferred.

For the recurring units of the formula (1) in oligomers, dendrimers and polymers, the same preferences apply as described above.

For the preparation of the oligomers or polymers, the monomers according to the invention are homopolymerised or copolymerised with further monomers. Suitable and preferred comonomers are selected from fluorenes (for example in accordance with EP 842208 or WO 00/22026), spirobifluorenes (for example in accordance with EP 707020, EP 894107 or WO 06/061181), para-phenylenes (for example in accordance with WO 92/18552), carbazoles (for example in accordance with WO 04/070772 or WO 04/113468), thiophenes (for example in accordance with EP 1028136), dihydrophenanthrenes (for example in accordance with WO 05/014689 or WO 07/006,383), cis- and trans-indenofluorenes (for example in accordance with WO 04/041901 or WO 04/113412), ketones (for example in accordance with WO 05/040302), phenanthrenes (for example in accordance with WO 05/104264 or WO 07/017,066) or also a plurality of these units. The polymers, oligomers and dendrimers usually also contain further units, for example emitting (fluorescent or phosphorescent) units, such as, for example, vinyltriarylamines (for example in accordance with WO 07/068,325) or phosphorescent metal complexes (for example in accordance with WO 06/003000), and/or charge-transport units, in particular those based on triarylamines.

The compounds of the formula (1) and corresponding oligomers, dendrimers and polymers are suitable for use in electronic devices, in particular in organic electroluminescent devices (OLEDs, PLEDs). Depending on the substitution, the compounds are employed in different functions and layers.

The invention therefore furthermore relates to the use of compounds of the formula (1) and corresponding oligomers, dendrimers or polymers in electronic devices, in particular in organic electroluminescent devices. The preferred compounds of the formulae (2) to (24) mentioned above are particularly suitable for this purpose.

The invention furthermore relates to organic electronic devices comprising at least one compound of the formula (1) or at least one corresponding oligomer, dendrimer or polymer, in particular organic electroluminescent devices comprising anode, cathode and at least one emitting layer, characterised in that at least one organic layer, which may be an emitting layer or another layer, comprises at least one compound of the formula (1) or at least one corresponding oligomer, dendrimer or polymer. The preferred compounds of the formulae (2) to (24) mentioned above are particularly suitable for this purpose.

Apart from the cathode, anode and the emitting layer, the organic electroluminescent device may also contain further layers. These are selected, for example, from in each case one or more hole-injection layers, hole-transport layers, electron-transport layers, electron-injection layers and/or charge-generation layers (IDMC 2003, Taiwan; Session 21 OLEO (5), T. Matsumoto, T. Nakada, J. Endo, K. Mori, N. Kawamura, A. Yokoi, J. Kido, *Multiphoton Organic EL Device Having Charge Generation Layer*). However, it should be pointed out that each of these layers does not necessarily have to be present.

The person skilled in the art of organic electroluminescence knows which materials he can employ for these further layers. In general, all materials as used in accordance with the prior art are suitable for the further layers, and the person skilled in the art will be able to combine these materials with the materials according to the invention in an organic electroluminescent device without carrying out an inventive step. Examples of preferred hole-transport materials which can be used in a hole-transport or hole-injection layer in the electroluminescent device according to the invention are indenofluorenamines and related derivatives (for example in accordance with WO 06/122630 or WO 06/100896), the amine derivatives disclosed in EP 1661888, hexaazatriphenylene derivatives (for example in accordance with WO 01/049806), amine derivatives with condensed aromatic rings (for example in accordance with U.S. Pat. No. 5,061,569), the amine derivatives disclosed in WO 95/09147, monobenzoindenofluorenamines (for example in accordance with WO 08/006,449) or dibenzoindenofluorenamines (for example in accordance with WO 07/140,847).

In a further preferred embodiment of the invention, the organic electroluminescent device contains a plurality of emitting layers, where at least one organic layer comprises at least one compound of the formula (1). These emission layers particularly preferably have in total a plurality of emission maxima between 380 nm and 750 nm, resulting overall in white emission, i.e. various emitting compounds which are able to fluoresce or phosphoresce and emit blue and yellow, orange or red light are used in the emitting layers. The compound of the formula (1) is preferably used here in a blue-emitting layer. Particular preference is given to three-layer systems, i.e. systems having three emitting layers, where at least one of these layers comprises at least one compound of the formula (1) and where the three layers exhibit blue, green and orange or red emission (for the basic structure see, for example, WO 05/011013). Emitters which have broadband emission and thus exhibit white emission are likewise suitable for white emission.

In an embodiment of the invention, the compounds of the formulae (1) to (24) are employed as host material for fluorescent dopants, in particular for blue-fluorescent dopants. In this case, one or more groups Ar and/or Y in formulae (1) and (3) to (7) are preferably selected from simple or condensed aryl or heteroaryl groups, in particular phenylanthryl or 1- or 2-naphthylanthryl. One or more groups Ar and/or Y in formulae (1) and (8) to (24) are furthermore preferably selected from condensed arylene groups, in particular 9,10-anthracene.

A host material in a system comprising host and dopant is taken to mean the component which is present in the higher proportion in the system. In a system comprising one host and a plurality of dopants, the host is taken to mean the component which has the highest proportion in the mixture.

The proportion of the host material of the formula (1) in the emitting layer is between 50.0 and 99.9% by weight, preferably between 80.0 and 99.5% by weight, particularly preferably between 90.0 and 99.0% by weight. Correspondingly, the proportion of the dopant is between 0.01 and 50.0% by weight, preferably between 0.1 and 20.0% by weight, particularly preferably between 0.5 and 15% by weight, very particularly preferably between 1.0 and 10.0% by weight.

Preferred dopants are selected from the class of the monostyrylamines, the distyrylamines, the tristyrylamines, the tetrastyrylamines, the styrylphosphines, the styryl ethers and the arylamines. A monostyrylamine is taken to mean a compound which contains one substituted or unsubstituted styryl group and at least one, preferably aromatic amine. A distyrylamine is taken to mean a compound which contains two substituted or unsubstituted styryl groups and at least one, preferably aromatic amine. A tristyrylamine is taken to mean a compound which contains three substituted or unsubstituted styryl groups and at least one, preferably aromatic amine. A tetrastyrylamine is taken to mean a compound which contains four substituted or unsubstituted styryl groups and at least one, preferably aromatic amine. The styryl groups are particularly preferably stilbenes, which may also be further substituted. Corresponding phosphines and ethers are defined analogously to the amines. For the purposes of this invention, an arylamine or an aromatic amine is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position. Further preferred dopants are selected from indenofluorenamines or indenofluorenediamines, for example in accordance with WO 06/122630, benzoeindenofluorenamines or benzoeindenofluorenediamines, for example in accordance with WO 08/006,449, and dibenzoindenofluorenamines or dibenzoindenofluorenediamines, for example in accordance with WO 07/140,847. Examples of dopants from the class of the styrylamines are substituted or unsubstituted tristilbenamines or the dopants described in WO 06/000388, WO 06/058737, WO 06/000389, WO 07/065,549 and WO 07/115,610. Preference is again furthermore given to the dopants according to the invention described below.

In a further embodiment of the invention, the compounds of the formula (1) are employed as emitting materials. The compounds are particularly suitable as emitting compounds If at least one Ar and/or Y group in compounds of the formulae (1) and (3) to (7) contains at least one arylamino unit. Preferred arylamino units are the groups of the formulae (32) and (33) depicted above. The compounds are furthermore suitable as emitting compounds If the group Y in compounds of the formulae (1) and (8) to (24) stands for N or $NAr^1$.

The proportion of the compound of the formula (1) in the mixture of the emitting layer is between 0.1 and 50.0% by weight, preferably between 0.5 and 20.0% by weight, particularly preferably between 1.0 and 10.0% by weight. Correspondingly, the proportion of the host material is between 50.0 and 99.9% by weight, preferably between 80.0 and 99.5% by weight, particularly preferably between 90.0 and 99.0% by weight.

Suitable host materials for this purpose are materials from various classes of substance. Preferred host materials are selected from the classes of the oligoarylenes (for example 2,2',7,7'-tetraphenylspirobifluorene as described in EP 676461 or dinaphthylanthracene), in particular the oligoarylenes containing condensed aromatic groups, the oligoarylenevinylenes (for example DPVBi or spiro-DPVBi as described in EP 676461), the polypodal metal complexes (for example as described in WO 04/081017), the hole-conducting compounds (for example as described in WO 04/058911), the electron-conducting compounds, in particular ketones, phosphine oxides, sulfoxides, etc. (for example as described in WO 05/084081 and WO 05/084082), the atropisomers (for example as described in WO 06/048268) or the boronic acid derivatives (for example as described in WO 06/117052). Suitable host materials are furthermore also the benz[a]anthracene compounds according to the invention described above. Apart from the compounds according to the invention, particularly preferred host materials are selected from the classes of the oligoarylenes containing naphthalene, anthracene and/or pyrene, or atropisomers of these compounds, the oligoarylenevinylenes, the ketones, the phosphine oxides and the sulfoxides. Apart from the benz[a]anthracene compounds according to the invention, very particularly preferred host materials are selected from the classes of the oligoarylenes containing anthracene and/or pyrene, or atropisomers of these compounds, the phosphine oxides and the sulfoxides. For the purposes of this invention, an oligoarylene is intended to be taken to mean a compound in which at least three aryl or arylene groups are bonded to one another.

In still a further embodiment of the invention, the compounds of the formula (1) are employed as hole-transport material or hole-injection material. The compounds are then preferably substituted by at least one $N(Ar^1)_2$ group; at least one radical R particularly preferably represents an $N(Ar^1)_2$ group. The $N(Ar^1)_2$ groups are preferably selected from the formulae (32) and (33) described above. The compounds are furthermore preferred if the group Y in compounds of the formulae (1) and (8) to (24) stands for N or $NAr^1$. The compound is preferably employed in a hole-transport or hole-injection layer. For the purposes of this invention, a hole-injection layer is a layer which is directly adjacent to the anode. For the purposes of this invention, a hole-transport layer is a layer which is located between a hole-injection layer and an emission layer. If the compounds of the formula (1) are used as hole-transport material or hole-injection material, it may be preferred for them to be doped with electron-acceptor compounds, for example with $F_4$-TCNQ or with compounds as described in EP 1476881 or EP 1596445.

In still a further embodiment of the invention, the compounds of the formula (1) are employed as electron-transport material. It is preferred here for one or more substituents R and/or R¹ to contain at least one C=O, P(=O) and/or SO₂ unit, which is preferably bonded directly to the benz[a]-anthracene. It is likewise preferred here for one or more substituents R and/or R¹ to contain an electron-poor heterocycle, such as, for example, imidazole, pyrazole, thiazole, benzimidazole, benzothiazole, triazole, oxadiazole, benzothiadiazole, phenanthroline, etc. It is likewise preferred for one or more Ar¹ groups in compounds of the formulae (1) and (8) to (24) to stand for an electron-poor heterocycle, such as, for example, imidazole, pyrazole, thiazole, benzimidazole, benzothiazole, triazole, oxadiazole, benzothiadiazole, phenanthroline, etc., and/or for the group Y to stand for an electron-poor heterocycle of this type or for C=O, POAr¹, SO or SO₂. It may furthermore be preferred for the compound to be doped with electron-donor compounds.

Recurring units of the formula (1) can also be employed in polymers either as polymer backbone, as emitting unit, as hole-transporting unit and/or as electron-transporting unit. The preferred substitution patterns here correspond to those described above.

Preference is furthermore given to an organic electroluminescent device, characterised in that one or more layers are applied by means of a sublimation process, in which the materials are vapour-deposited in vacuum sublimation units at a pressure below $10^{-5}$ mbar, preferably below $10^{-6}$ mbar, particularly preferably below $10^{-7}$ mbar.

Preference is likewise given to an organic electroluminescent device, characterised in that one or more layers are applied by means of the OVPD (organic vapour phase deposition) process or with the aid of carrier-gas sublimation, where the materials are applied at a pressure between $10^{-5}$ mbar and 1 bar.

Preference is furthermore given to an organic electroluminescent device, characterised in that one or more layers are produced from solution, such as, for example, by spin coating, or by means of any desired printing process, such as, for example, screen printing, flexographic printing or offset printing, but particularly preferably LITI (light induced thermal imaging, thermal transfer printing) or ink-jet printing. Soluble compounds are necessary for this purpose. High solubility can be achieved through suitable substitution of the compounds.

The compounds according to the invention have increased efficiency and a significantly longer lifetime on use in organic electroluminescent devices, making the organic electroluminescent devices according to the invention more suitable for use in high-quality and long-lived displays than those which comprise materials in accordance with the prior art. Furthermore, the compounds according to the invention have high thermal stability and a high glass-transition temperature and can be sublimed without decomposition.

The present application text is directed to the use of the compounds according to the invention in relation to OLEDs and PLEDs and the corresponding displays. In spite of this restriction of the description, it is possible for the person skilled in the art, without further inventive step, also to employ the compounds according to the invention in other electronic devices, for example in organic field-effect transistors (O-FETs), organic thin-film transistors (O-TFTs), organic light-emitting transistors (O-LETs), organic integrated circuits (O-ICs), organic solar cells (O-SCs), organic field-quench devices (O-FQDs), light-emitting electrochemical cells (LECs), organic laser diodes (O-lasers) or organic photo receptors.

The present invention likewise relates to the use of the compounds according to the invention in the corresponding devices and to these devices themselves.

EXAMPLES

The following syntheses are carried out under a protective-gas atmosphere, unless indicated otherwise. The starting materials can be purchased from ALDRICH or ABCR or prepared by literature methods. 2- and 3-bromobenz[a]anthracene: Hallmark et al., *J. Lab. Comp. Radiopharm.* 1981, 18(3), 331; 4-bromobenz[a]anthracene: Badgar et al., *J. Chem. Soc.* 1949, 799; 5-bromobenz[a]anthracene: Newman et al., *J. Org. Chem.* 1982, 47(15), 2837. It was not possible to determine the glass-transition temperature of all compounds by means of DSC measurement.

Example 1

Synthesis of 5-bromobenz[a]anthracene a) 2-(1-Formylphenyl)-1-naphthylmethane

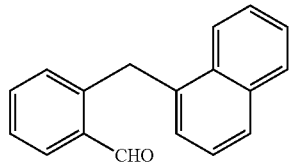 [SMILES: O=Cc1ccccc1Cc1cccc2ccccc12]

The corresponding Grignard compound is prepared from 88.3 g (500 mmol) of 1-chloromethylnaphthalene and 12.2 g (500 mmol) of magnesium in 500 ml of ether. After the Grignard solution has been cooled to −78° C., 59 ml (530 mmol) of trimethyl borate are added, the mixture is then allowed to warm to room temperature, the solvent is removed in vacuo, 500 ml of toluene, 92.5 g (500 mmol) of 2-bromobenzaldehyde, 2.9 g (2.5 mmol) of tetrakis(triphenylphosphino)palladium(0) and 300 ml of 2 M sodium carbonate solution are added to the residue, and the reaction mixture is heated under reflux for 16 h. After cooling, the organic phase is separated off, washed twice with 500 ml of water each time, filtered through silica gel and then evaporated to dryness, and the residue is recrystallised from toluene/acetonitrile. Yield: 93.1 g (378 mmol), 75.6%, purity about 97% (NMR).

b) 2-(1-Formylphenyl)-1-(4-bromonaphthyl)methane

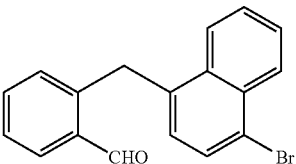 [SMILES: O=Cc1ccccc1Cc1ccc(Br)c2ccccc12]

A mixture of 19.5 ml (380 mmol) of bromine and 300 ml of dichloromethane is added dropwise with exclusion of light to a solution, cooled to 0° C., of 86.2 g (350 mmol) of 2-(1-formylphenyl)-1-naphthylmethane in 1500 ml of dichloromethane. After stirring for a further 3 h, 1000 ml of 5% sodium sulfite solution are added, the mixture is stirred briefly, the organic phase is separated off, washed three times with 500 ml of water and evaporated in vacuo, and the residue is taken up in a little acetone. After standing for 24 h, the crystals are filtered off with suction, washed with acetone:n-hexane (1:1) and dried in vacuo. Yield: 90.7 g (279 mmol), 79.7%, purity about 98% (NMR).

c) 5-Bromobenz[a]anthracene

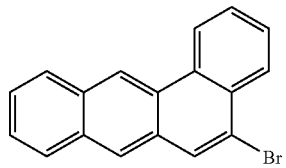 [SMILES: Brc1cc2cc3ccccc3cc2c2ccccc12]

32.5 g (100 mmol) of 2-(1-formylphenyl)-1-(4-bromonaphthyl)methane are incorporated into 1000 g of polyphosphoric acid at 50° C. The mass is heated at 100° C. for 2 h, cooled and taken up in 5l of ice-water. The solid is filtered off with suction, washed with copious water, dried and then filtered through an aluminium oxide column in toluene. Yield: 25.5 g (83 mmol), 83.0%, purity about 98% (NMR).

Example 2

Synthesis of benz[a]anthracene-5-boronic acid

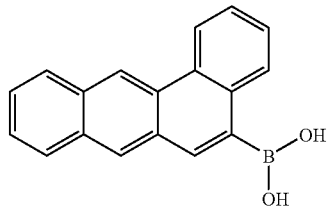 [SMILES: OB(O)c1cc2cc3ccccc3cc2c2ccccc12]

52 ml (130 mmol) of n-butyllithium (2.5 M in n-hexane) are added dropwise with vigorous stirring at −78° C. to a suspension of 30.7 g (100 mmol) of 5-bromobenz[a]anthracene in 1000 ml of THF, and the mixture is stirred for a further 2 h. 16.7 ml (150 mmol) of trimethyl borate are added to the red solution in one portion with vigorous stirring, the mixture is stirred at −78° C. for a further 30 min., then warmed to room temperature over the course of 3 h, 300 ml of water are added, and the mixture is stirred for 30 min. The organic phase is separated off and evaporated to dryness in vacuo. The solid is taken up in 100 ml of n-hexane, filtered off with suction, washed once with 100 ml of hexane and dried in vacuo. Yield: 24.8 g (91 mmol), 91%, purity about 90% (NMR) of boronic acid, with varying amounts of boronic anhydride and borinic acid. The boronic acid can be used in this form without further purification.

The corresponding boronic acids are obtained analogously to Example 2 from the corresponding bromides (Examples 3 to 6).

| Ex. | Bromide | Boronic acid | Yield |
|---|---|---|---|
| 3 | 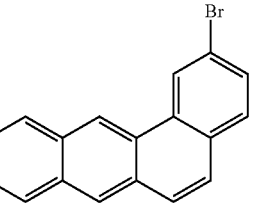 | 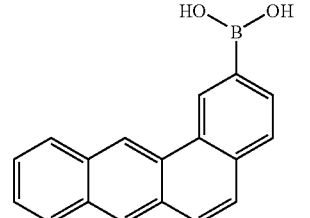 | 74.6% |
| 4 | 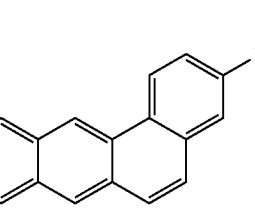 | 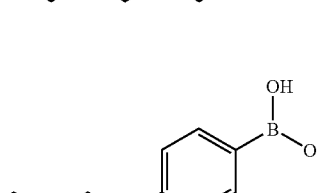 | 78.3% |
| 5 | 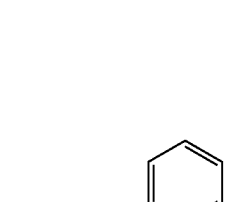 | 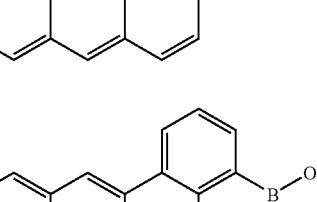 | 87.0% |

| Ex. | Bromide | Boronic acid | Yield |
|---|---|---|---|
| 6 | 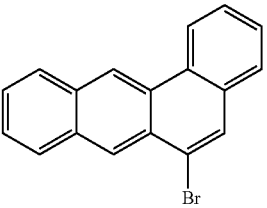 | 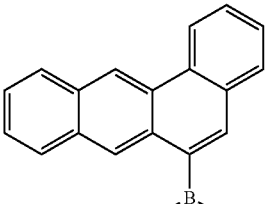 [SMILES: Brc1cc2ccccc2c2cc3ccccc3cc12] | 88.5% |

Example 7

Synthesis of 9-(naphth-2-yl)-10-(benz[a]anthracen-4-yl)-anthracene

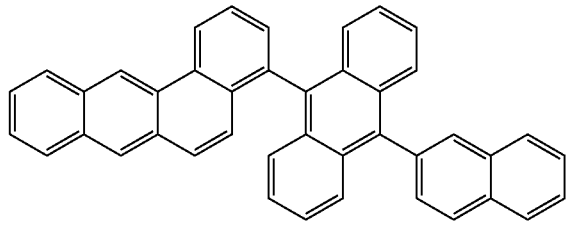 [SMILES: c1ccc2cc(-c3c4ccccc4c(-c4cccc5c4ccc4cc6ccccc6cc45)c4ccccc34)ccc2c1]

913 mg (3 mmol) of tri-o-tolylphosphine and then 112 mg (0.5 mmol) of palladium(II) acetate are added to a well-stirred suspension of 19.2 g (50 mmol) of 9-bromo-10-(2-naphthyl)anthracene, 15.0 g (55 mmol) of benz[a]anthracene-4-boronic acid, 25.5 g (120 mmol) of tripotassium phosphate in a mixture of 300 ml of toluene, 100 ml of dioxane and 400 ml of water, and the mixture is subsequently heated under reflux for 16 h. After cooling, the precipitated solid is filtered off with suction, washed three times with 50 ml of toluene, three times with 50 ml of ethanol:water (1:1, v:v) and three times with 100 ml of ethanol, recrystallised three times from DMF (about 10 ml/g) and subsequently sublimed twice (p=$5\times10^{-5}$ mbar, T=330° C.). Yield: 15.6 g (29 mmol), 58.8%, purity 99.9% (HPLC), $T_g$=168.9° C.

The following compounds according to the invention are obtained analogously to Example 7 from the corresponding bromides and boronic acids (Ex. 8 to 13).

| Ex. | Boronic acid | Bromide | Product | Yield |
|---|---|---|---|---|
| 8 | 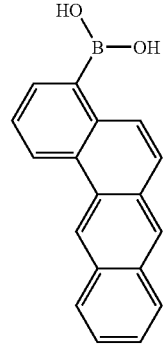 [SMILES: OB(O)c1cccc2c1ccc1cc3ccccc3cc12] | 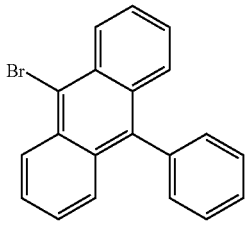 [SMILES: Brc1c2ccccc2c(-c2ccccc2)c2ccccc12] | 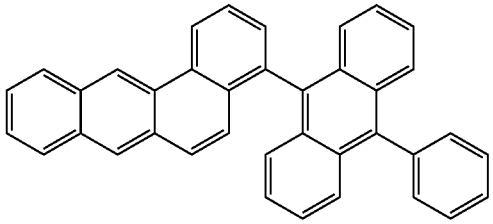 [SMILES: c1ccc(-c2c3ccccc3c(-c3cccc4c3ccc3cc5ccccc5cc34)c3ccccc23)cc1] | 61.3%<br>$T_g$ =<br>147.9° C. |
| 9 | 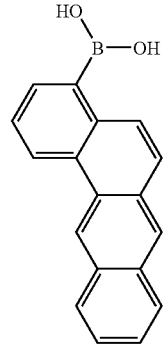 [SMILES: OB(O)c1cccc2c1ccc1cc3ccccc3cc12] | 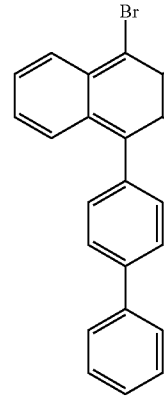 | 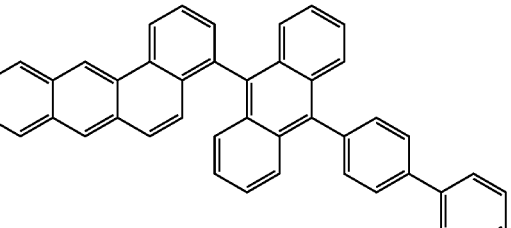 | 64.9%<br>$T_g$ =<br>161.4° C. |

-continued
| Ex. | Boronic acid | Bromide | Product | Yield |
|---|---|---|---|---|
| 10 | 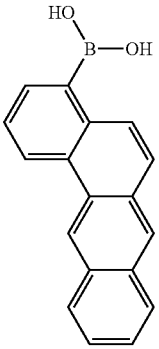 [SMILES: OB(O)c1cccc2c1ccc1cc3ccccc3cc12] | 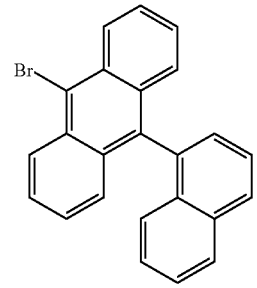 [SMILES: Brc1c2ccccc2c(-c2cccc3ccccc23)c2ccccc12] | 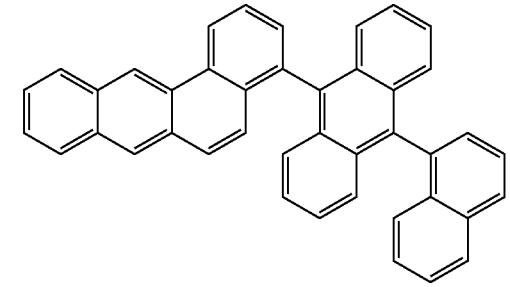 [SMILES: c1ccc2cc3c(ccc4c(-c5c6ccccc6c(-c6cccc7ccccc67)c6ccccc56)cccc43)cc2c1] | 55.7% |
| 11 | 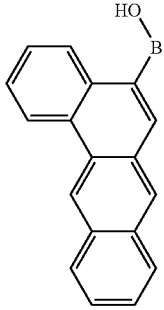 | 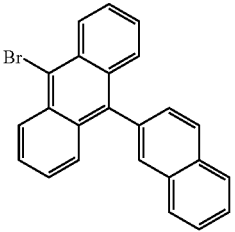 [SMILES: Brc1c2ccccc2c(-c2ccc3ccccc3c2)c2ccccc12] | 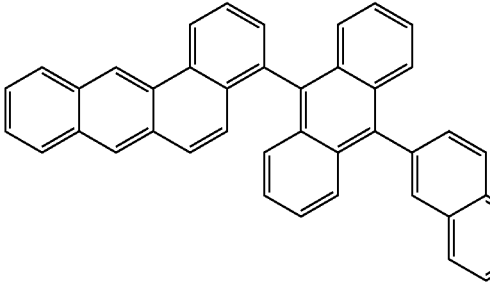 | 70.0%<br>$T_g =$<br>175.2° C. |
| 12 | 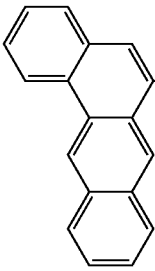 | 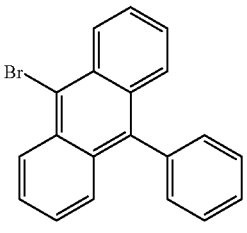 [SMILES: Brc1c2ccccc2c(-c2ccccc2)c2ccccc12] | 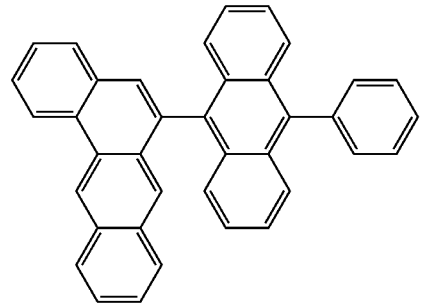 [SMILES: c1ccc(-c2c3ccccc3c(-c3cc4ccccc4c4cc5ccccc5cc34)c3ccccc23)cc1] | 48.3% |
| 13 | 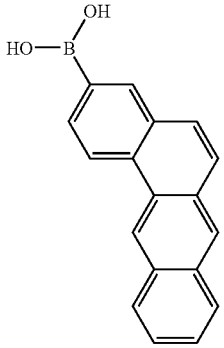 [SMILES: OB(O)c1ccc2c(ccc3cc4ccccc4cc32)c1] | 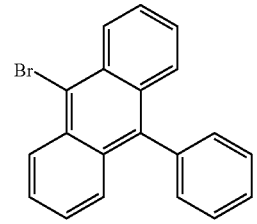 | 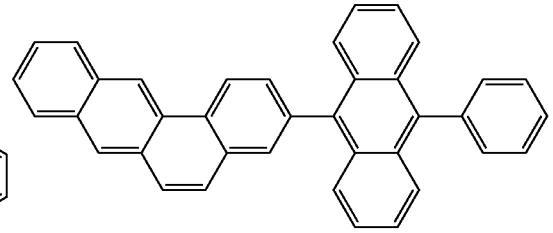 | 59.6% |

Example 14

Synthesis of 1,4-bis(10-(benz[a]anthracen-4-yl)anthracen-10-yl)benzene

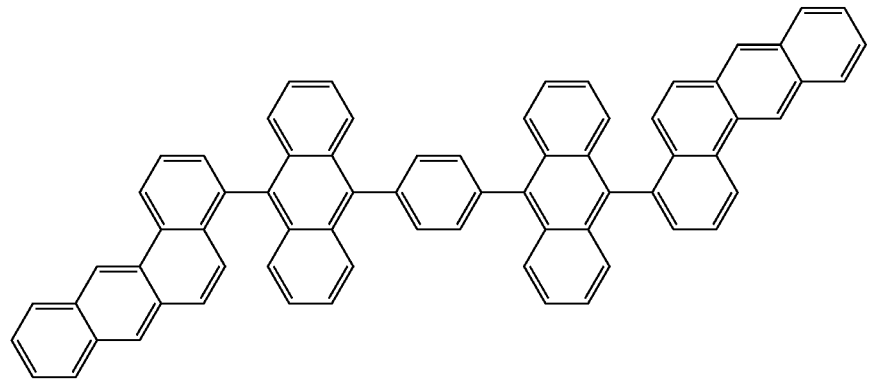 [SMILES: c1ccc2cc3c(ccc4c(-c5c6ccccc6c(-c6ccc(-c7c8ccccc8c(-c8cccc9c8ccc8cc%10ccccc%10cc89)c8ccccc78)cc6)c6ccccc56)cccc43)cc2c1]

Preparation analogous to Example 7. The 19.2 g (50 mmol) of 9-bromo-10-(2-naphthyl)anthracene are replaced by 14.7 g (25 mmol) of 1,4-bis(9-bromoanthracen-10-yl)benzene. Recrystallisation three times from NMP (about 10 ml/g); sublimation (p=5×10$^{-5}$ mbar, T=360° C.). Yield: 14.2 g (16 mmol), 64.3%, purity 99.9% (HPLC).

Example 15

Synthesis of 1,3,5-tris(benz[a]anthracen-4-yl)benzene

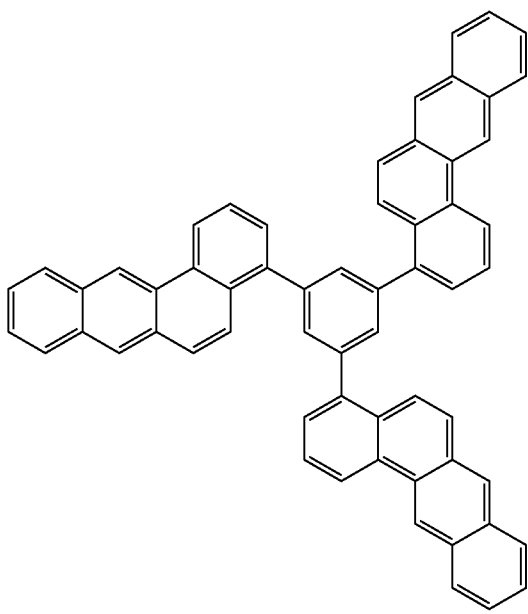 [SMILES: c1ccc2cc3c(ccc4c(-c5cc(-c6cccc7c6ccc6cc8ccccc8cc67)cc(-c6cccc7c6ccc6cc8ccccc8cc67)c5)cccc43)cc2c1]

Preparation analogous to Example 7. The 19.2 g (50 mmol) of 9-bromo-10-(2-naphthyl)anthracene are replaced by 5.0 g (16 mmol) of 1,3,5-tribromobenzene. Recrystallisation four times from o-dichlorobenzene (about 25 ml/g); sublimation (p=5×10$^{-5}$ mbar, T=350° C.). Yield: 8.4 g (11 mmol), 69.3%, purity 99.9% (HPLC).

Example 16

Synthesis of 5-(benz[a]anthracen-5-yl)benz[a]anthracene

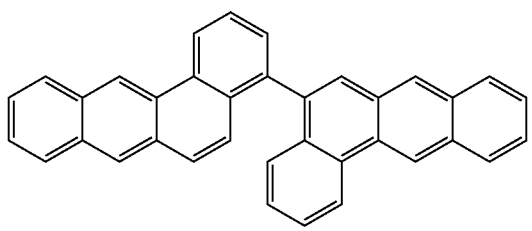 [SMILES: c1ccc2cc3c(ccc4c(-c5cc6cc7ccccc7cc6c6ccccc56)cccc43)cc2c1]

Preparation analogous to Example 7. The 19.2 g (50 mmol) of 9-bromo-10-(2-naphthyl)anthracene are replaced by 15.4 g (50 mmol) of 5-bromobenz[a]anthracene, and the benz[a]anthracene-4-boronic acid is replaced by benz[a]anthracene-5-boronic acid. Recrystallisation four times from o-dichlorobenzene (about 15 ml/g); sublimation (p=5×10$^{-5}$ mbar, T=320° C.). Yield: 15.0 g (33 mmol), 66.0%, purity 99.9% (HPLC), $T_g$=141.2° C.

Example 17

Synthesis of 4-(benz[a]anthracen-5-yl)benz[a]anthracene

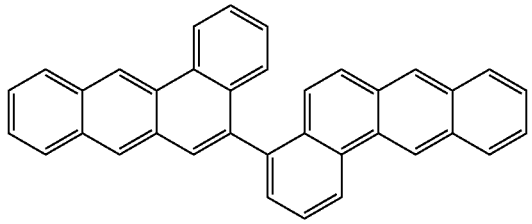 [SMILES: c1ccc2cc3c(ccc4c(-c5cc6cc7ccccc7cc6c6ccccc56)cccc43)cc2c1]

Preparation analogous to Example 7. The 19.2 g (50 mmol) of 9-bromo-10-(2-naphthyl)anthracene are replaced by 15.4 g (50 mmol) of 5-bromobenz[a]anthracene. Recrystallisation four times from o-dichlorobenzene (about 15 ml/g); sublimation (p=5×10⁻⁵ mbar, T=310° C.). Yield: 16.4 g (36 mmol), 72.1%, purity 99.9% (HPLC).

Example 18

Synthesis of 1-phenyl-2-(4-benz[a]anthracen-4-yl-phenyl)benzimidazole

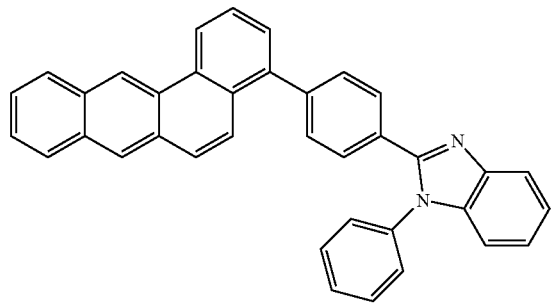 [SMILES: c1ccc(-n2c(-c3ccc(-c4cccc5c4ccc4cc6ccccc6cc45)cc3)nc3ccccc32)cc1]

Preparation analogous to Example 7. The 19.2 g (50 mmol) of 9-bromo-10-(2-naphthyl)anthracene are replaced by 17.5 g (50 mmol) of 1-phenyl-2-(4-bromophenyl)benzimidazole. After the reaction mixture has been cooled, the organic phase is separated off, washed three times with 300 ml of water, filtered through silica gel and evaporated to dryness. The glass-like residue is dissolved in 50 ml of boiling chloroform, and 100 ml of ethanol are added to the solution. After standing for 12 h, the colourless crystals are filtered off with suction and subsequently chromatographed on silica gel with pure dichloromethane (Rf=0.3). Finally, the product is recrystallised again from chloroform/ethanol. Sublimation (p=5×10⁻⁵ mbar, T=310° C.). Yield: 15.5 g (31 mmol), 62.4%, purity 99.9% (HPLC), $T_g$=110.9° C.

Example 19

Synthesis of 4-(bis(3-methylphenyl)amino)benz[a]-anthracene

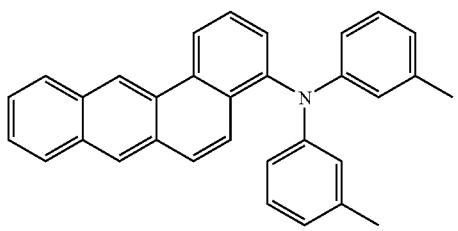 [SMILES: Cc1cccc(N(c2cccc(C)c2)c2cccc3c2ccc2cc4ccccc4cc23)c1]

190 µl (1 mmol) of chloro-di-tert-butylphosphine and then 112 mg (0.5 mmol) of palladium(II) acetate are added to a suspension of 15.4 g (50 mmol) of 4-bromobenz[a]anthracene, 11.8 g (60 mmol) of bis(3-methylphenyl)amine and 7.7 g (80 mmol) of sodium tert-butoxide in 500 ml of toluene, and the mixture is subsequently heated under reflux for 5 h. After the mixture has been cooled to 60° C., 500 ml of water are added, the organic phase is separated off, filtered through silica gel, evaporated virtually to dryness at 80° C. in vacuo, and 300 ml of ethanol are then added. After cooling, the solid is filtered off with suction. Recrystallisation five times from dioxane (about 8 ml/g); sublimation (p=5×10⁻⁵ mbar, T=280° C.). Yield: 11.9 g (28 mmol), 56.1%, purity 99.9% (HPLC).

Example 20

Synthesis of 9-(phenyl)-10-(benz[a]anthracen-5-yl)-anthracene

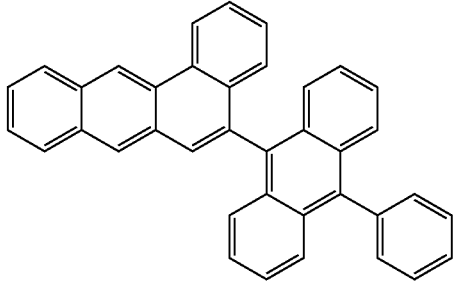 [SMILES: c1ccc(-c2c3ccccc3c(-c3cc4cc5ccccc5cc4c4ccccc34)c3ccccc23)cc1]

913 mg (3 mmol) of tri-o-tolylphosphine and then 112 mg (0.5 mmol) of palladium(II) acetate are added to a well-stirred suspension of 16.7 g (50 mmol) of 9-bromo-10-(phenyl)anthracene, 15.0 g (55 mmol) of benz-[a]anthracene-5-boronic acid, 25.5 g (120 mmol) of tripotassium phosphate in a mixture of 300 ml of toluene, 100 ml of dioxane and 400 ml of water, and the mixture is subsequently heated under reflux for 16 h. After the mixture has been cooled, the precipitated solid is filtered off with suction, washed three times with 50 ml of toluene, three times with 50 ml of ethanol:water (1:1, v:v) and three times with 100 ml of ethanol, recrystallised three times from DMF (about 7 ml/g) and subsequently sublimed twice (p=5×10⁻⁵ mbar, T=320° C.). Yield: 16.3 g (34 mmol), 67.8%, purity 99.9% (HPLC), $T_g$=150.0° C.

The following compounds according to the invention are obtained analogously to Example 20 from the corresponding bromides and boronic acids (Ex. 21 to 26).

| Ex. | Boronic acid | Bromide | Product | Yield |
|---|---|---|---|---|
| 21 | | | | 51.0% |
| 22 | | | | 66.0% |
| 23 | | | | 59.5% |
| 24 | | | | 38.5% |

-continued

| Ex. | Boronic acid | Bromide | Product | Yield |
|---|---|---|---|---|
| 25 | | | | 63.2% |
| 26 | | | | 70.7% |

Example 27

Synthesis of 4-(benz[a]anthracen-4-yl)benz[a]anthracene

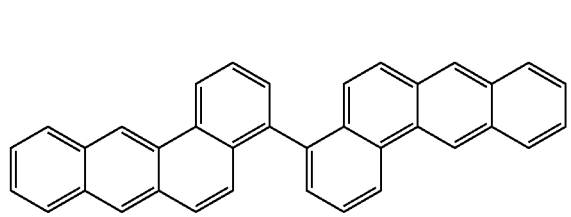 [SMILES: c1ccc2cc3c(ccc4c(-c5cccc6c5ccc5cc7ccccc7cc56)cccc43)cc2c1]

Preparation analogous to Example 7. 9-Bromo-10-(2-naphthyl)anthracene is replaced by 15.4 g (50 mmol) of 4-bromobenz[a]anthracene. Recrystallisation four times from o-dichlorobenzene (about 15 ml/g); sublimation (p=5× $10^{-5}$ mbar, T=320° C.). Yield: 16.8 g (37 mmol), 74.0%, purity 99.9% (HPLC), $T_g$=130.3° C.

Example 28

Synthesis of 1,4-bis(benz[a]anthracen-4-yl)benzene

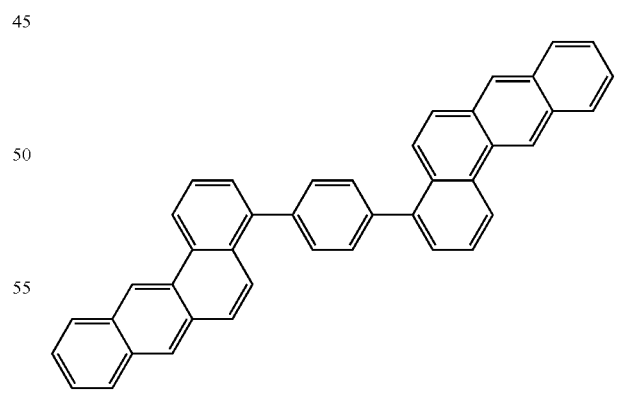

Preparation analogous to Example 7. 9-Bromo-10-(2-naphthyl)anthracene is replaced by 4.1 g (25 mmol) of benzene-1,4-diboronic acid. Recrystallisation five times from o-dichlorobenzene (about 20 ml/g); sublimation (p=5×$10^{-5}$ mbar, T=400° C.). Yield: 11.1 g (21 mmol), 84.0%, purity 99.9% (HPLC).

Example 29

Synthesis of 4-(7-phenylbenz[a]anthracen-4-yl)-7-phenylbenz[a]anthracene

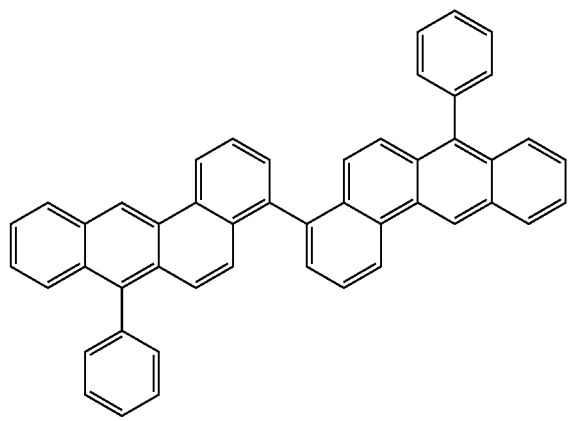 [SMILES: c1ccc(-c2c3ccccc3cc3c2ccc2c(-c4cccc5c4ccc4c(-c6ccccc6)c6ccccc6cc45)cccc23)cc1]

19.6 g (110 mmol) of N-bromosuccinimide are added in one portion at 100° C. with vigorous stirring to a suspension of 22.7 g (50 mmol) of 4-(benz[a]anthracen-4-yl)benz[a]anthracene in 1000 ml of DMF. The suspension is kept at 100° C. for a further 30 min. and cooled, and 1000 ml of ethanol are then added. The precipitated solid is filtered off with suction, washed three times with 100 ml of ethanol each time and dried in vacuo. The resultant solid is reacted analogously to Example 7 with 15.9 g (130 mmol) of benzeneboronic acid, Recrystallisation five times from DMF (about 6 ml/g); sublimation (p=5×10$^{-5}$ mbar, T=360° C.). Yield: 21.8 g (36 mmol), 72.0%, purity 99.9% (HPLC), Tg=181.4° C.

The following compounds according to the invention are obtained analogously to Example 29 from the corresponding boronic acids (Ex. 30 to 34),

| Ex. | Boronic acid | Product | Yield |
|---|---|---|---|
| 30 | | | 39.0% |
| 31 | | | 61.1% |

| Ex. | Boronic acid | Product | Yield |
|---|---|---|---|
| 32 | 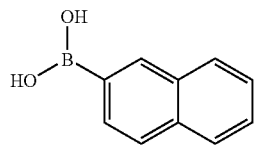 [SMILES: OB(O)c1ccc2ccccc2c1] | 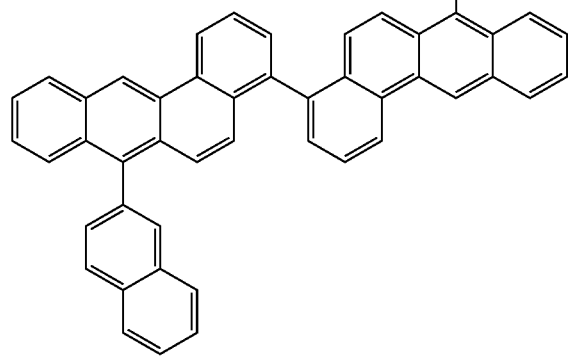 | 55.6% |
| 33 | 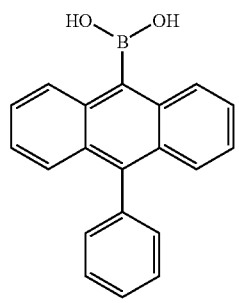 [SMILES: OB(O)c1c2ccccc2c(-c2ccccc2)c2ccccc12] | 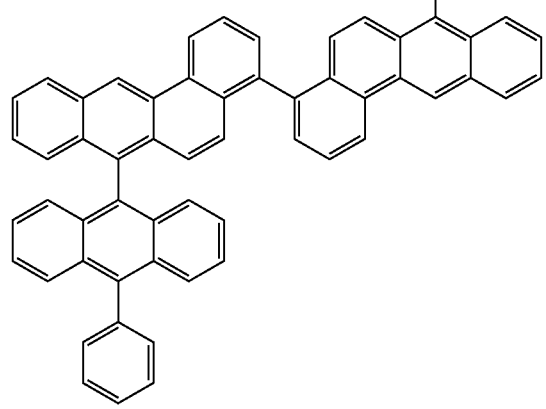 | 21.3% |

| Ex. | Boronic acid | Product | Yield |
|---|---|---|---|
| 34 | 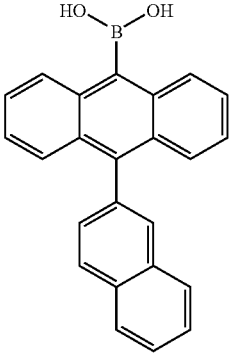 [SMILES: OB(O)c1c2ccccc2c(-c2ccc3ccccc3c2)c2ccccc12] | 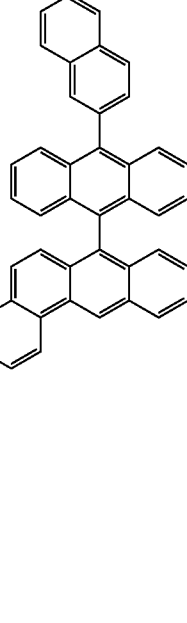 | 19.8% |

Example 35

Synthesis of 4,7-bis(naphth-1-yl)benz[a]anthracene

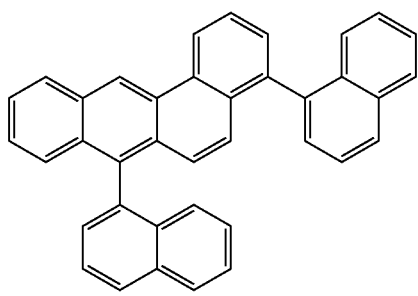 [SMILES: c1ccc2c(-c3cccc4c3ccc3c(-c5cccc6ccccc56)c5ccccc5cc34)cccc2c1]

19.6 g (110 mmol) of N-bromosuccinimide are added in one portion at 100° C. with vigorous stirring to a suspension of 15.4 g (50 mmol) of 4-bromobenz[a]anthracene in 300 ml of DMF. The suspension is kept at 100° C. for a further 30 min. and cooled, and 1000 ml of ethanol are added. The precipitated solid is filtered off with suction, washed three times with 100 ml of ethanol each time and dried in vacuo.

The resultant solid is reacted analogously to Example 7 with 22.4 g (130 mmol) of 1-naphthaleneboronic acid. Recrystallisation five times from DMF (about 4 ml/g); sublimation (p=5×10$^{-5}$ mbar, T=355° C.). Yield: 12.5 g (26 mmol), 52.0%, purity 99.9% (HPLC), Tg=137.1° C.

The following compounds according to the invention are obtained analogously to Example 35 from the corresponding boronic acids (Ex. 36 to 40).

| Ex. | Boronic acid | Product | Yield |
|---|---|---|---|
| 36 | 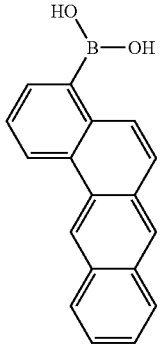 [SMILES: OB(O)c1cccc2c1ccc1cc3ccccc3cc12] | 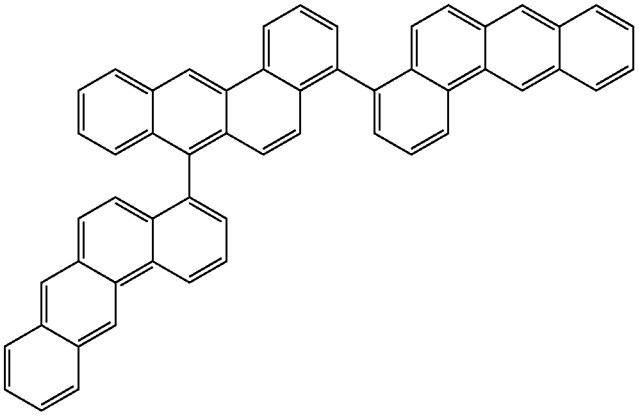 [SMILES: c1ccc2cc3c(ccc4c(-c5cccc6c5ccc5c(-c7cccc8c7ccc7cc9ccccc9cc78)c7ccccc7cc56)cccc43)cc2c1] | 44.4% |

-continued

| Ex. | Boronic acid | Product | Yield |
| --- | --- | --- | --- |
| 37 | (phenanthren-9-yl)boronic acid | product structure | 71.6% |
| 38 | (naphthalen-2-yl)boronic acid | product structure | 53.6% |
| 39 | (10-phenylanthracen-9-yl)boronic acid | product structure | 50.2% |
| 40 | (10-(naphthalen-2-yl)anthracen-9-yl)boronic acid | product structure | 57.5% |

Example 41

Synthesis of 9-(phenyl)-10-(7-phenylbenz[a]anthracen-4-yl)anthracene

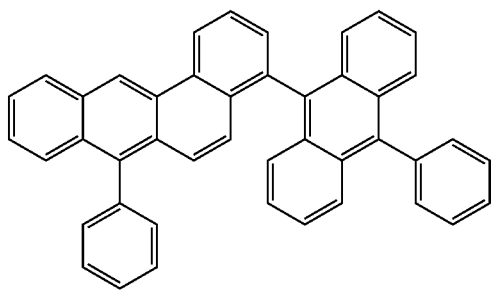 [SMILES: c1ccc(-c2c3ccccc3c(-c3cccc4c3ccc3c(-c5ccccc5)c5ccccc5cc34)c3ccccc23)cc1]

913 mg (3 mmol) of tri-o-tolylphosphine and then 112 mg (0.5 mmol) of palladium(II) acetate are added to a well-stirred suspension of 12.9 g (50 mmol) of 9-bromoanthracene, 15.0 g (55 mmol) of benz[a]anthracene-4-boronic acid, 25.5 g (120 mmol) of tripotassium phosphate in a mixture of 300 ml of toluene, 100 ml of dioxane and 400 ml of water, and the mixture is subsequently heated under reflux for 16 h. After cooling, the precipitated solid is filtered off with suction, washed three times with 50 ml of toluene, three times with 50 ml of ethanol:water (1:1, v:v), three times with 100 ml of ethanol and finally dried.

16.9 g (95 mmol) of N-bromosuccinimide are added in one portion at 100° C. to a suspension of 18.2 g (45 mmol) of the resultant 9-benz[a]-anthracen-4-ylanthracene in 500 ml of DMF. After 3 h, 500 ml of ethanol are added at room temperature, and the solid is filtered off with suction, washed with ethanol and dried.

913 mg (3 mmol) of tri-o-tolylphosphine and then 112 mg (0.5 mmol) of palladium(II) acetate are added to a well-stirred suspension of 22.5 g (40 mmol) of the resultant 9-bromo-10-(7-bromobenz[a]anthracen-4-yl)-anthracene, 12.2 g (100 mmol) of benzoic acid, 25.5 g (120 mmol) of tripotassium phosphate in a mixture of 300 ml of toluene, 100 ml of dioxane and 400 ml of water, and the mixture is subsequently heated under reflux for 16 h. After cooling, the precipitated solid is filtered off with suction, washed three times with 50 ml of toluene, three times with 50 ml of ethanol:water (1:1, v:v), three times with 100 ml of ethanol and finally dried. Recrystallisation five times from DMF (about 3 ml/g); sublimation (p=5×10$^{-5}$ mbar, T=350° C.). Yield: 12.6 g (23 mmol), 46.0%, purity 99.9% (HPLC), Tg=171.8° C.

The following compounds according to the invention are obtained analogously to Example 41 from the corresponding boronic acids (Ex. 42 to 46).

| Ex. | Boronic acid | Product | Yield |
|---|---|---|---|
| 42 | 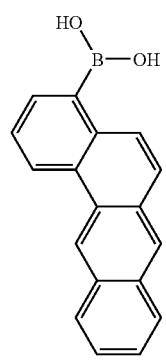 [SMILES: OB(O)c1cccc2c1ccc1cc3ccccc3cc12] | 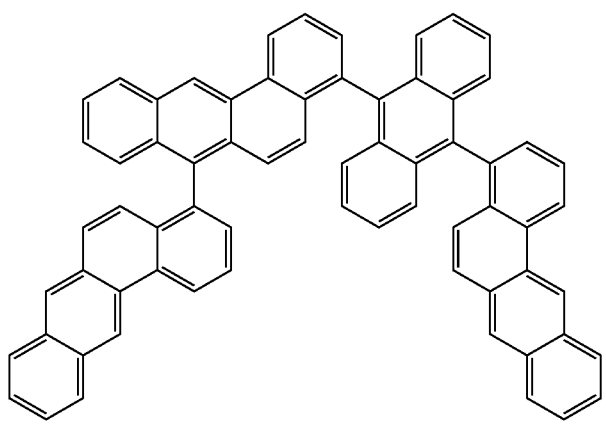 [SMILES: c1ccc2cc3c(ccc4c(-c5c6ccccc6c(-c6cccc7c6ccc6c(-c8cccc9c8ccc8cc%10ccccc%10cc89)c8ccccc8cc67)c6ccccc56)cccc43)cc2c1] | 68.5% |
| 43 | 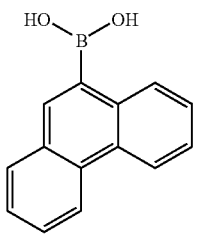 [SMILES: OB(O)c1cc2ccccc2c2ccccc12] | 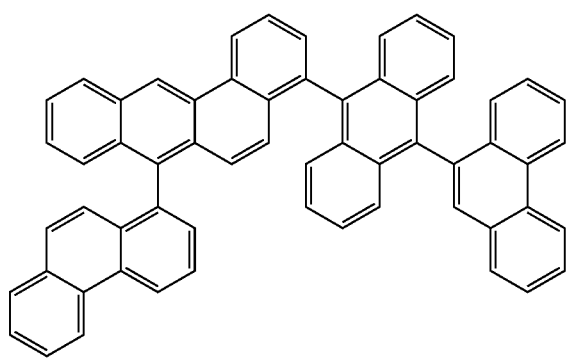 [SMILES: c1ccc2c(-c3cccc4c3ccc3ccccc34)c3ccc4c(-c5c6ccccc6c(-c6cc7ccccc7c7ccccc67)c6ccccc56)cccc4c3cc2c1] | 71.0% |

-continued
| Ex. | Boronic acid | Product | Yield |
|---|---|---|---|
| 44 | 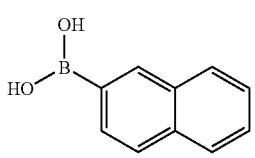 [SMILES: OB(O)c1ccc2ccccc2c1] | 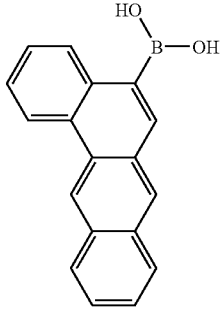 [SMILES: OB(O)c1cc2cc3ccccc3cc2c2ccccc12] | 56.4% |
| 45 | 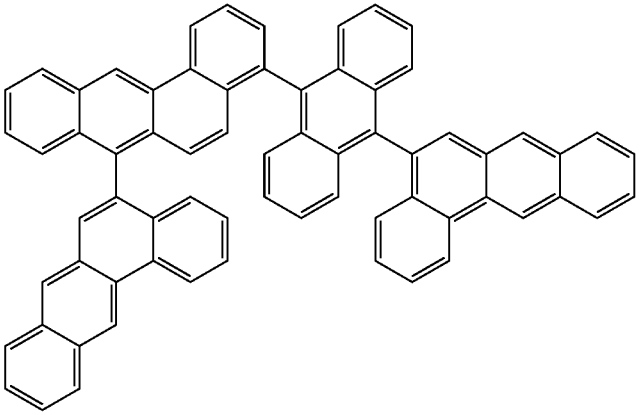 [SMILES: c1ccc2cc3c(cc(-c4c5ccccc5c(-c5cccc6c5ccc5c(-c7cc8cc9ccccc9cc8c8ccccc78)c7ccccc7cc56)c5ccccc45)c4ccccc43)cc2c1] | 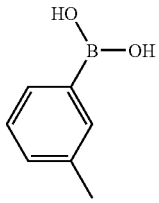 | 35.2% |
| 46 | 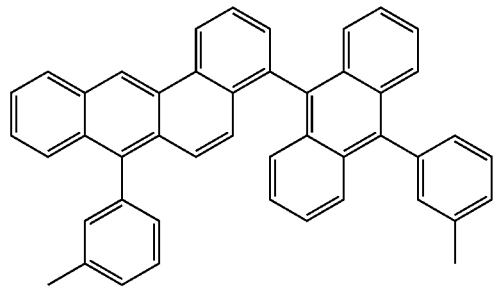 [SMILES: Cc1cccc(-c2c3ccccc3c(-c3cccc4c3ccc3c(-c5cccc(C)c5)c5ccccc5cc34)c3ccccc23)c1] | | 47.1% |

Example 48

Synthesis of 1,4-bis(7-phenyl(benz[a]anthracen-4-yl))-benzene

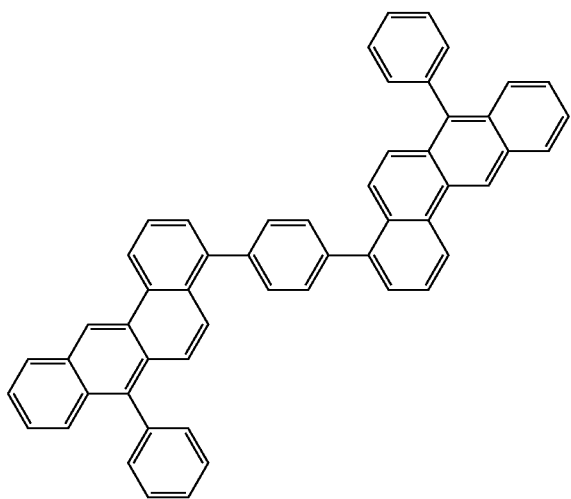 [SMILES: c1ccc(-c2c3ccccc3cc3c2ccc2c(-c4ccc(-c5cccc6c5ccc5c(-c7ccccc7)c7ccccc7cc56)cc4)cccc23)cc1]

A suspension of 26.5 g (50 mmol) of 1,4-bis(benz[a]anthracen-4-yl)benzene and 19.6 g (110 mmol) of N-bromosuccinimide in 500 ml of o-dichlorobenzene is slowly heated to the boil with vigorous stirring. The mixture is subsequently boiled under reflux for 2 h and allowed to cool, and the precipitate is filtered off with suction, washed three times with 100 ml of ethanol each time and dried in vacuo.

913 mg (3 mmol) of tri-o-tolylphosphine and then 112 mg (0.5 mmol) of palladium(II) acetate are added to a well-stirred suspension of 21.2 g (40 mmol) of the resultant 1,4-bis(7-bromo(benz[a]anthracen-4-yl))benzene, 12.2 g (100 mmol) of benzeneboronic acid, 25.5 g (120 mmol) of tripotassium phosphate in a mixture of 300 ml of toluene, 100 ml of dioxane and 400 ml of water, and the mixture is subsequently heated under reflux for 16 h. After cooling, the precipitated solid is filtered off with suction, washed three times with 50 ml of toluene, three times with 50 ml of ethanol:water (1:1, v:v), three times with 100 ml of ethanol and finally dried. Recrystallisation five times from o-dichlorobenzene (about 7 ml/g); sublimation (p=5×10$^{-5}$ mbar, T=400° C.). Yield: 16.4 g (24 mmol), 48.0%, purity 99.9% (HPLC), Tg=176.7° C.

The following compounds according to the invention are obtained analogously to Example 48 from the corresponding boronic acids (Ex. 49 to 53).

| Ex. | Boronic acid | Product | Yield |
|---|---|---|---|
| 49 | | | 46.9% |
| 50 | | | 46.4% |

| Ex. | Boronic acid | Product | Yield |
|---|---|---|---|
| 51 | | | 76.2% |
| 52 | | | 65.8% |
| 53 | | | 67.8% |

Example 54

Synthesis of 4-(diphenylamino)benz[a]anthracene

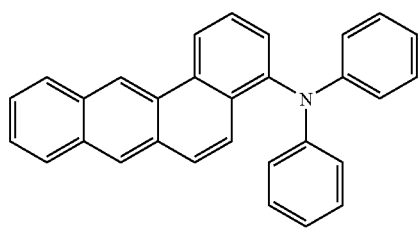 [SMILES: c1ccc(N(c2ccccc2)c2cccc3c2ccc2cc4ccccc4cc23)cc1]

190 μl (1 mmol) of chlorodi-tert-butylphosphine and then 112 mg (0.5 mmol) of palladium(II) acetate are added to a suspension of 15.4 g (50 mmol) of 4-bromobenz[a]anthracene, 10.2 g (60 mmol) of diphenylamine and 7.7 g (80 mmol) of sodium tert-butoxide in 500 ml of toluene, and the mixture is subsequently heated under reflux for 5 h. After the mixture has been cooled to 60° C., 500 ml of water are added, the organic phase is separated off, filtered through silica gel, evaporated virtually to dryness at 80° C. in vacuo, and 300 ml of ethanol are then added. After cooling, the solid is filtered off with suction. Recrystallisation five times from dioxane (about 8 ml/g); sublimation (p=5×10$^{-5}$ mbar, T=280° C.). Yield: 12.7 g (32 mmol), 64.1%, purity 99.9% (HPLC), Tg=74.7° C.

The following compounds according to the invention are obtained analogously to Example 54 from the corresponding amines (Ex. 55 to 59).

| Ex. | Amine | Product | Yield |
|---|---|---|---|
| 55 | 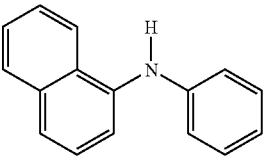 [SMILES: c1ccc(Nc2cccc3ccccc23)cc1] | 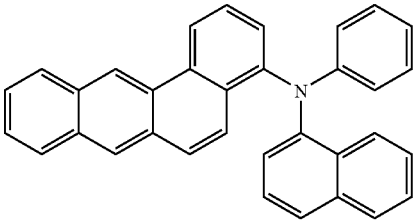 [SMILES: c1ccc(N(c2cccc3ccccc23)c2cccc3c2ccc2cc4ccccc4cc23)cc1] | 66.3% |
| 56 | 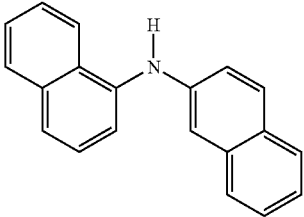 [SMILES: c1ccc2cc(Nc3cccc4ccccc34)ccc2c1] | 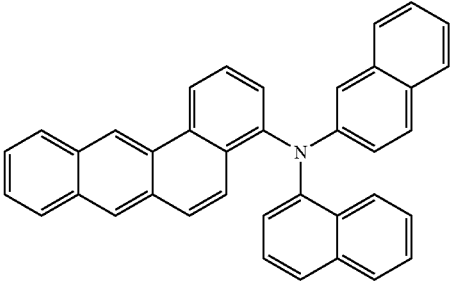 [SMILES: c1ccc2cc(N(c3cccc4ccccc34)c3cccc4c3ccc3cc5ccccc5cc34)ccc2c1] | 44.0% |
| 57 | 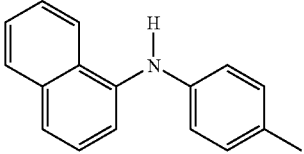 [SMILES: Cc1ccc(Nc2cccc3ccccc23)cc1] | 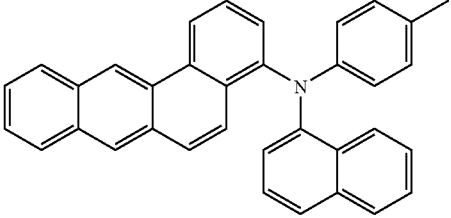 [SMILES: Cc1ccc(N(c2cccc3ccccc23)c2cccc3c2ccc2cc4ccccc4cc23)cc1] | 67.3% |
| 58 | 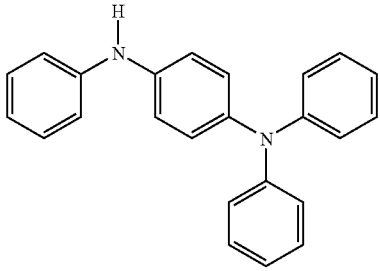 [SMILES: c1ccc(Nc2ccc(N(c3ccccc3)c3ccccc3)cc2)cc1] | 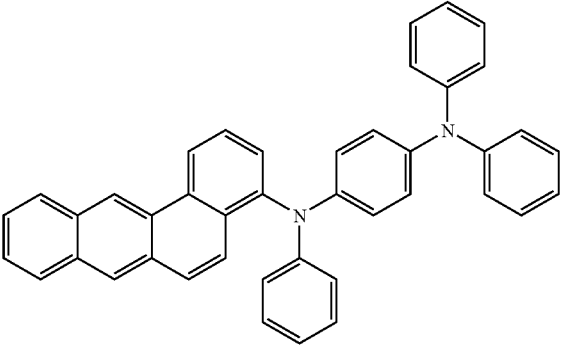 [SMILES: c1ccc(N(c2ccccc2)c2ccc(N(c3ccccc3)c3cccc4c3ccc3cc5ccccc5cc34)cc2)cc1] | 62.1% |
| 59 | 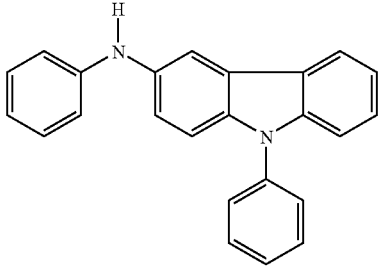 [SMILES: c1ccc(Nc2ccc3c(c2)c2ccccc2n3-c2ccccc2)cc1] | 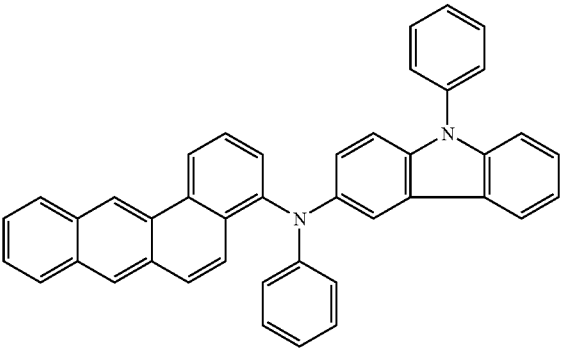 [SMILES: c1ccc(N(c2ccc3c(c2)c2ccccc2n3-c2ccccc2)c2cccc3c2ccc2cc4ccccc4cc23)cc1] | 71.0% |

Example 60

Synthesis of 4,7-bis(diphenylamino)benz[a]anthracene

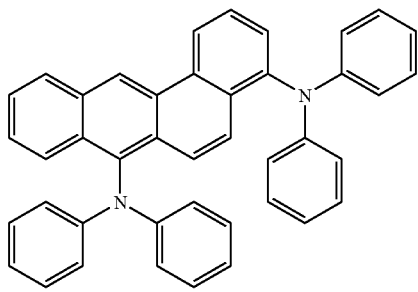 [SMILES: c1ccc(N(c2ccccc2)c2cccc3c2ccc2c(N(c4ccccc4)c4ccccc4)c4ccccc4cc23)cc1]

380 µl (2 mmol) of chlorodi-tert-butylphosphine and then 224 mg (1 mmol) of palladium(II) acetate are added to a suspension of 19.3 g (50 mmol) of 4,7-dibromobenz[a]anthracene (preparation as described in Ex. 35), 20.4 g (120 mmol) of diphenylamine and 15.4 g (160 mmol) of sodium tert-butoxide in 500 ml of toluene, and the mixture is subsequently heated under reflux for 5 h. After the mixture has been cooled to 60° C., 500 ml of water are added, the organic phase is separated off, filtered through silica gel, evaporated virtually to dryness at 80° C. in vacuo, and 300 ml of ethanol are then added. After cooling, the solid is filtered off with suction. Recrystallisation fives times from dioxane (about 8 ml/g); sublimation (p=5×10$^{-5}$ mbar, T=300° C.). Yield: 16.9 g (30 mmol), 60.2%, purity 99.9% (HPLC), Tg=134.9° C.

| Ex. | Amine | Product | Yield |
|---|---|---|---|
| 61 | 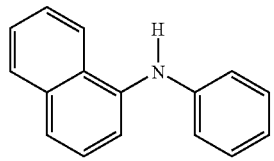 [SMILES: c1ccc(Nc2cccc3ccccc23)cc1] | 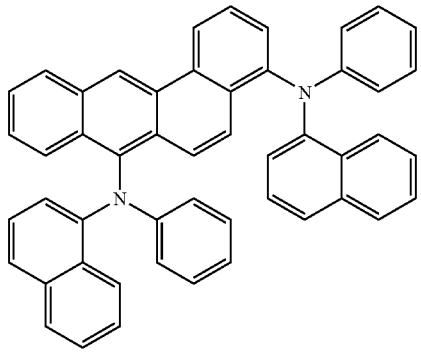 [SMILES: c1ccc(N(c2cccc3ccccc23)c2cccc3c2ccc2c(N(c4ccccc4)c4cccc5ccccc45)c4ccccc4cc23)cc1] | 37.8% |
| 62 | 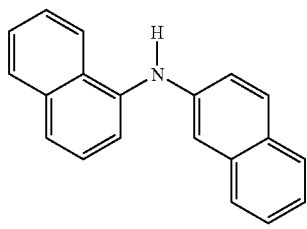 [SMILES: c1ccc2cc(Nc3cccc4ccccc34)ccc2c1] | 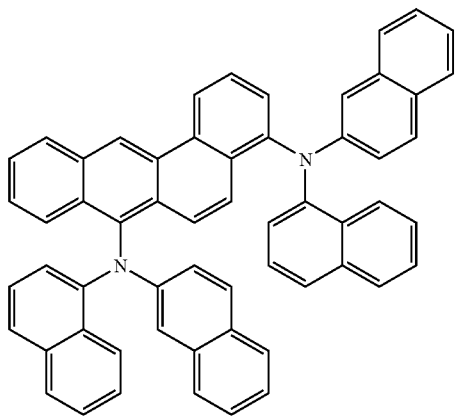 [SMILES: c1ccc2cc(N(c3cccc4ccccc34)c3cccc4c3ccc3c(N(c5ccc6ccccc6c5)c5cccc6ccccc56)c5ccccc5cc34)ccc2c1] | 42.0% |

-continued
| Ex. | Amine | Product | Yield |
|---|---|---|---|
| 63 | 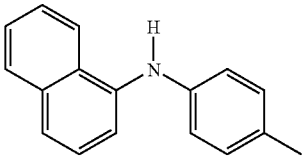 [SMILES: Cc1ccc(Nc2cccc3ccccc23)cc1] | 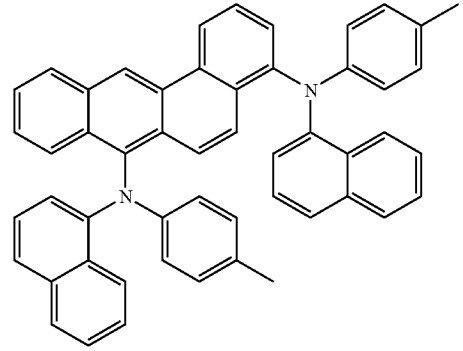 [SMILES: Cc1ccc(N(c2cccc3ccccc23)c2cccc3c2ccc2c(N(c4ccc(C)cc4)c4cccc5ccccc45)c4ccccc4cc23)cc1] | 33.9% |
| 64 | 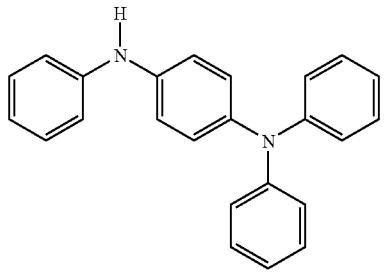 [SMILES: c1ccc(Nc2ccc(N(c3ccccc3)c3ccccc3)cc2)cc1] | 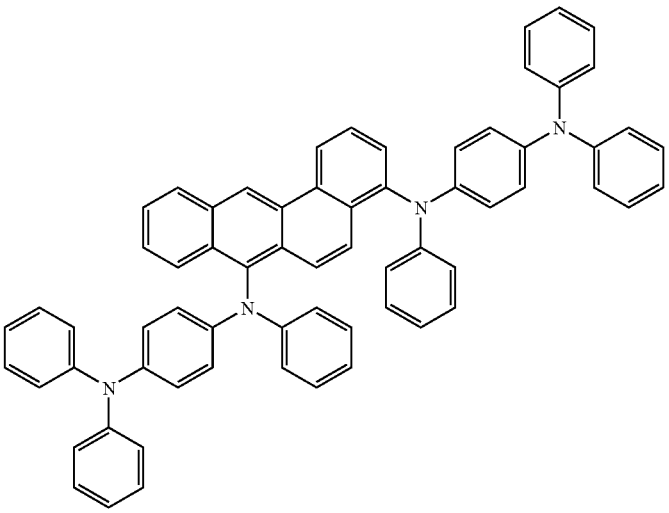 [SMILES: c1ccc(N(c2ccccc2)c2ccc(N(c3ccccc3)c3cccc4c3ccc3c(N(c5ccccc5)c5ccc(N(c6ccccc6)c6ccccc6)cc5)c5ccccc5cc34)cc2)cc1] | 72.8% |
| 65 | 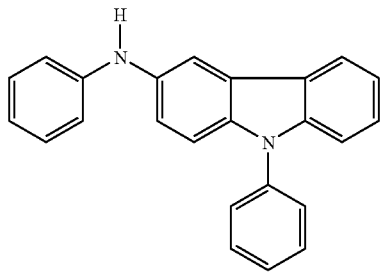 | 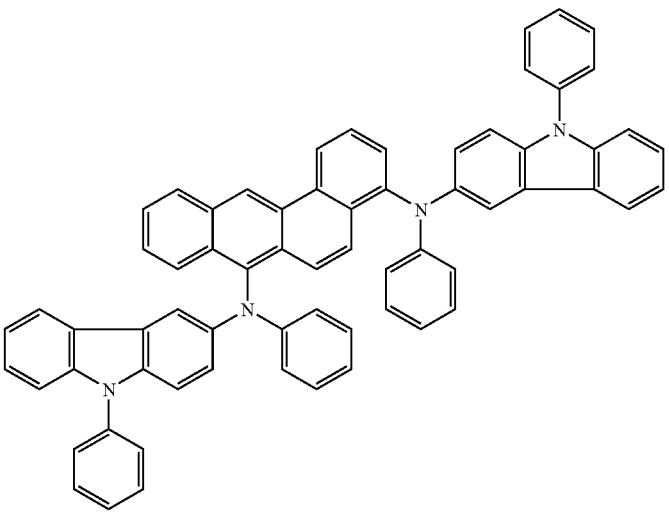 [SMILES: c1ccc(N(c2ccc3c(c2)c2ccccc2n3-c2ccccc2)c2cccc3c2ccc2c(N(c4ccccc4)c4ccc5c(c4)c4ccccc4n5-c4ccccc4)c4ccccc4cc23)cc1] | 61.3% |

Example 66

Synthesis of 2-, 3-, 4-, 5- and 6-bromo-7,12-dideuterobenz[a]anthracene

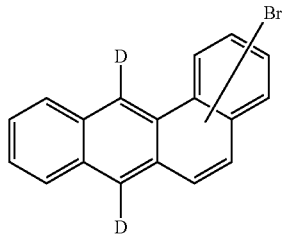

A suspension of 1.7 g (5 mmol) of the corresponding 2-, 3-, 4-, 5- or 6-bromobenz[a]anthracenequinone (2-bromo, 3-bromo: see *J. Org. Chem.* 1983, 48(17), 2926; 4-bromo: see *J. Org. Chem.* 1987, 52(26), 5668; 5-bromo: see *Bull. Chem. Soc. Jpn.* 1976, 49(12), 3713) in a mixture of 4 ml of 50% $D_3PO_2$ in $D_2O$, 8 ml of 57% DI in $D_2O$ and 18 ml of $CD_3COOD$ is heated under reflux for 15 h. After cooling, the solid is filtered off with suction, washed well with water, washed once with 50 ml of boiling EtOH and finally dried. The degree of deuteration, based on the degree of deuteration of the starting materials $D_3PO_2$, DI and $CD_3COOD$, is >99%.

| Ex. | Quinone | Product | Yield |
|-----|---------|---------|-------|
| 67  |         |         | 94.5% |
| 68  |         |         | 88.6% |
| 69  |         |         | 89.1% |
| 70  |         |         | 14.3% |
| 71  |         |         | 67.5% |

The resultant 2-, 3-, 4-, 5- and 6-bromo-7,12-dideuterobenz[a]anthracenes can be converted analogously to Examples 1 to 60 into the analogous 7- and/or 12-deuterated compounds 1 to 60 according to the invention.

Example 72

Synthesis of 4,7-bis(4-phenyl-1H-benzimidazolyl)-benz[a]anthracene

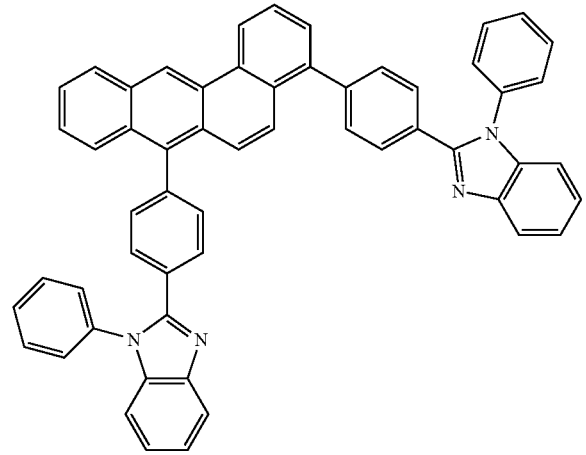 [SMILES: c1ccc(-n2c(-c3ccc(-c4cccc5c4ccc4c(-c6ccc(-c7nc8ccccc8n7-c7ccccc7)cc6)c6ccccc6cc45)cc3)nc3ccccc32)cc1]

913 mg (3 mmol) of tri-o-tolylphosphine and then 112 mg (0.5 mmol) of palladium(II) acetate are added to a well-stirred suspension of 11 g (31.5 mmol) of 1-phenyl-2-(4-bromophenyl)benzimidazole, 4.4 g (14 mmol) of benz[a]anthracene-4,7-diboronic acid and 13 g (65 mmol) of tripotassium phosphate in a mixture of 300 ml of toluene, 100 ml of dioxane and 400 ml of water, and the mixture is subsequently heated under reflux for 16 h. After cooling, the precipitated solid is filtered off with suction, washed three times with 50 ml of toluene, three times with 50 ml of ethanol/water (1:1, v:v) and three times with 100 ml of ethanol, recrystallised three times from DMF (about 10 ml/g) and subsequently sublimed twice (p=5×10⁻⁵ mbar, T=308° C.). Yield: 17.5 g (23 mmol), 41%, purity 99.9% (HPLC), 111.4° C.

Example 73

Synthesis of 4-phenyl-7-(4-phenyl-1H-benzimidazolyl)-benz[a]anthracene a) 4-Phenylbenz[a]anthracene

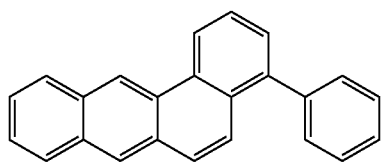 [SMILES: c1ccc(-c2cccc3c2ccc2cc4ccccc4cc23)cc1]

913 mg (3 mmol) of tri-o-tolylphosphine and then 112 mg (0.5 mmol) of palladium(II) acetate are added to a well-stirred suspension of 7.8 g (50 mmol) of bromobenzene, 15.0 g (55 mmol) of benz[a]anthracene-4-boronic acid and 25.5 g (120 mmol) of tripotassium phosphate in a mixture of 300 ml of toluene, 100 ml of dioxane and 400 ml of water, and the mixture is subsequently heated under reflux for 16 h. After cooling, the precipitated solid is filtered off with suction, washed three times with 50 ml of toluene, three times with 50 ml of ethanol:water (1:1, v:v), three times with 100 ml of ethanol and finally dried.

b) 7-Bromo-4-phenylbenz[a]anthracene

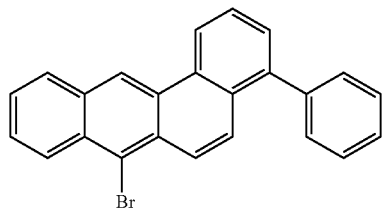 [SMILES: Brc1c2ccccc2cc2c1ccc1c(-c3ccccc3)cccc12]

16.9 g (95 mmol) of N-bromosuccinimide are added at 100° C. to a suspension of 18.2 g (45 mmol) of 4-phenylbenz[a]anthracene in 500 ml of DMF. After 3 h, 500 ml of ethanol are added at room temperature, and the solid is filtered off with suction, washed with ethanol and dried.

c) 4-(4-Phenylbenz[a]anthracen-7-yl)benzaldehyde

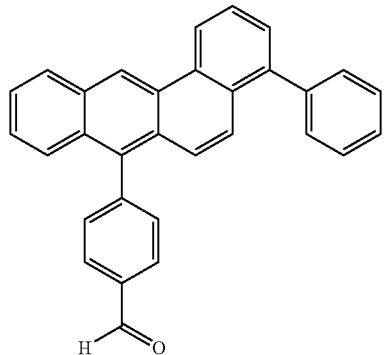 [SMILES: O=Cc1ccc(-c2c3ccccc3cc3c2ccc2c(-c4ccccc4)cccc23)cc1]

913 mg (3 mmol) of tri-o-tolylphosphine and then 112 mg (0.5 mmol) of palladium(II) acetate are added to a well-stirred suspension of 15.3 g (40 mmol) of 7-bromo-4-phenylbenz[a]anthracene, 7.5 g (50 mmol) of 4-formylphenylboronic acid and 25.5 g (120 mmol) of tripotassium phosphate in a mixture of 300 ml of toluene, 100 ml of dioxane and 400 ml of water, and the mixture is subsequently heated under reflux for 16 h. After cooling, the precipitated solid is filtered off with suction, washed three times with 50 ml of toluene, three times with 50 ml of ethanol:water (1:1, v:v), three times with 100 ml of ethanol and finally dried. Recrystallisation from DMF. Yield: 14.3 g (35 mmol), 88%.

d) 7-(4-Phenyl-1H-1-benzimidazolyl)-4-phenylbenz[a]anthracene

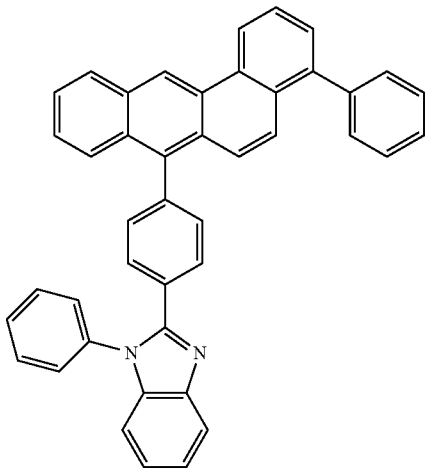 [SMILES: c1ccc(-c2cccc3c2ccc2c(-c4ccc(-c5nc6ccccc6n5-c5ccccc5)cc4)c4ccccc4cc23)cc1]

In a flask which has been thoroughly dried by heating, 18 g (45 mmol) of 4-(4-phenylbenz[a]anthracen-7-yl)benzaldehyde and 15.3 g (81 mmol) of N-phenyl-o-phenylenediamine are dissolved in 900 ml of DMF, 104 g (169 mmol) of potassium hydrogen monopersulfate are added dropwise, and the mixture is subsequently stirred for a further 1 h and then heated at 60° C. for 1 h. After cooling, the precipitated solid is filtered off with suction, washed three times with 50 ml of ethanol:water (1:1, v:v) and three times with 100 ml of ethanol and finally dried. Recrystallisation five times from DMF (about 4 ml/g); sublimation (p=5×10$^{-5}$ mbar, T=320° C.). Yield: 6 g (11 mmol), 26%, purity 99.9% (HPLC), Tg=130.4° C.

Example 74

Synthesis of 7-naphth-1-yl-4-(4-phenyl-4H-benzimidazole)benz[a]anthracene a) 4-Benz[a]anthracen-4-ylbenzaldehyde

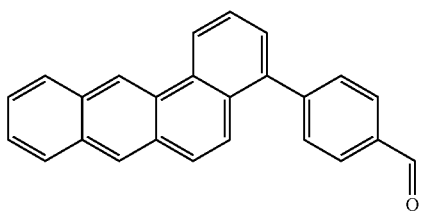 [SMILES: O=Cc1ccc(-c2cccc3c2ccc2cc4ccccc4cc23)cc1]

14 g (7.9 mmol) of tri-o-tolylphosphine and then 300 mg (1.3 mmol) of palladium(II) acetate are added to a well-stirred suspension of 50 g (333 mmol) of 4-formylphenylboronic acid, 81 g (266 mmol) of 4-bromobenz[a]anthracene and 118 g (558 mmol) of tripotassium phosphate in a mixture of 500 ml of toluene, 500 ml of dioxane and 400 ml of water, and the mixture is subsequently heated under reflux for 16 h. After cooling, the precipitated solid is filtered off with suction, washed three times with 50 ml of toluene, three times with 50 ml of ethanol:water (1:1, v:v), three times with 100 ml of ethanol and finally dried. Yield: 49.7 g (149 mmol), 56%.

b) 4-(7-Bromobenz[a]anthracen-4-yl)benzaldehyde

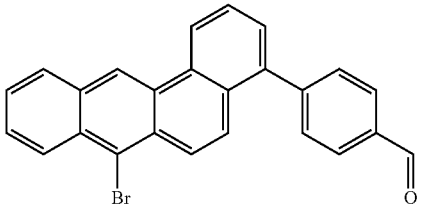 [SMILES: O=Cc1ccc(-c2cccc3c2ccc2c(Br)c4ccccc4cc23)cc1]

29.4 g (165 mmol) of N-bromosuccinimide are added at 100° C. to a suspension of 49 g (150 mmol) of 4-benz[a]anthracen-4-ylbenzaldehyde in 800 ml of DMF. After 3 h, 500 ml of ethanol are added at room temperature, and the solid is filtered off with suction, washed with ethanol and dried. Yield: 49.3 g (119 mmol), 79%.

c) 4-(7-Naphth-1-ylbenz[a]anthracen-4-yl)benzaldehyde

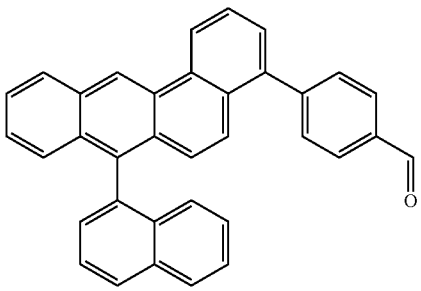 [SMILES: O=Cc1ccc(-c2cccc3c2ccc2c(-c4cccc5ccccc45)c4ccccc4cc23)cc1]

850 mg (2.8 mmol) of tri-o-tolylphosphine and then 108 mg (0.48 mmol) of palladium(II) acetate are added to a well-stirred suspension of 49 g (115 mmol) of naphthyl-1-boronic acid, 21 g (126 mmol) of 4-(7-bromobenz[a]anthracen-4-yl)benzaldehyde, 36.6 g (172 mmol) of tripotassium phosphate in a mixture of 500 ml of toluene, 500 ml of dioxane and 400 ml of water, and the mixture is subsequently heated under reflux for 16 h. After cooling, the precipitated solid is filtered off with suction, washed three times with 50 ml of toluene, three times with 50 ml of ethanol:water (1:1, v:v), three times with 100 ml of ethanol and finally dried. Yield: 76 g (161 mmol), 54%.

d) 7-Naphth-1-yl-4-(4-phenyl-1H-benzimidazole)benz[a]anthracene

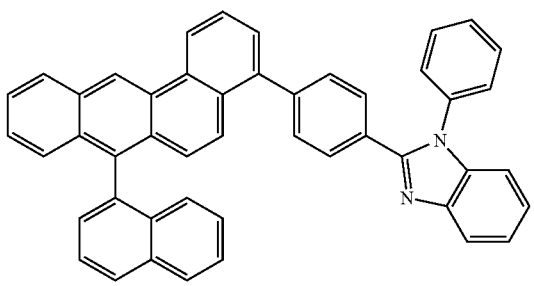 [SMILES: c1ccc(-n2c(-c3ccc(-c4cccc5c4ccc4c(-c6cccc7ccccc67)c6ccccc6cc45)cc3)nc3ccccc32)cc1]

In a flask which has been thoroughly dried by heating, 76 g (116 mmol) of 4-(7-naphth-1-ylbenz[a]anthracen-4-yl)benzaldehyde and 112 g (598 mmol) of N-phenyl-o-phenylenediamine are dissolved in 900 ml of DMF, 240 g (359 mmol) of potassium hydrogen monopersulfate are added dropwise, and the mixture is subsequently stirred for a further 1 h and then heated at 60° C. for 1 h. After cooling, the precipitated solid is filtered off with suction, washed three times with 50 ml of ethanol:water (1:1, v:v), three times with 100 ml of ethanol and finally dried. Recrystallisation five times from DMF (about 4 ml/g); sublimation (p=5×10$^{-5}$ mbar, T=320° C.). Yield: 60 g (96 mmol), 83%, purity 99.9% (HPLC), Tg=161.3° C.

Example 75

Synthesis of 7-(4-phenyl-1H-benzimidazole)-4-(9-phenylanthracen-10-yl)benz[a]anthracene a) 4-(9-Phenylanthracen-10-yl)benz[a]anthracene

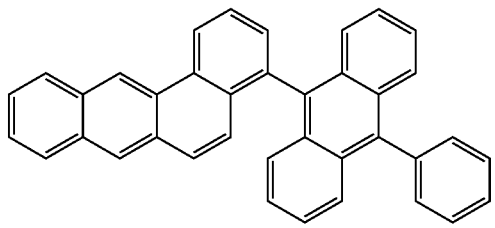

3 g (9.8 mmol) of tri-o-tolylphosphine and then 391 mg (1.7 mmol) of palladium(II) acetate are added to a well-stirred suspension of 20 g (60 mmol) of 9-bromo-10-phenylanthracene, 19.8 g (73 mmol) of 4-bromo-benz[a]-anthracene and 19 g (89 mmol) of tripotassium phosphate in a mixture of 250 ml of toluene, 50 ml of dioxane and 250 ml of water, and the mixture is subsequently heated under reflux for 16 h. After cooling, the precipitated solid is filtered off with suction, washed three times with 50 ml of toluene, three times with 50 ml of ethanol:water (1:1, v:v), three times with 100 ml of ethanol and finally dried. Yield: 34 g (71 mmol), 97%.

b) 7-Bromo-4-(9-phenylanthracen-10-yl)benz[a]anthracene

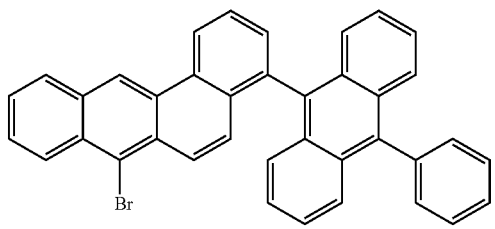

20 g (116 mmol) of N-bromosuccinimide are added at 100° C. to a suspension of 55 g (116 mmol) of 4-(9-phenylanthracen-10-yl)benz[a]anthracene in 500 ml of DMF. After 3 h, 500 ml of ethanol are added at room temperature, and the solid is filtered off with suction, washed with ethanol and dried. Yield: 63 g (113 mmol), 65%.

c) 7-(p-Benzaldehyde)-4-(9-phenylanthracen-10-yl)benz[a]anthracene

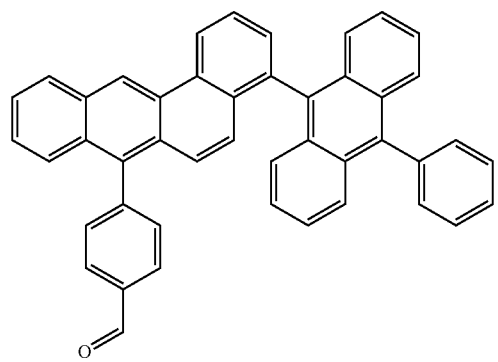 [SMILES: O=Cc1ccc(-c2c3ccccc3cc3c2ccc2c(-c4c5ccccc5c(-c5ccccc5)c5ccccc45)cccc23)cc1]

1.05 g (3.6 mmol) of tri-o-tolylphosphine and then 130 mg (0.58 mmol) of palladium(II) acetate are added to a well-stirred suspension of 21 g (145 mmol) of 4-formylphenylboronic acid, 66 g (119 mmol) of 7-bromo-4-(9-phenylanthracen-10-yl)benz[a]anthracene and 49 g (234 mmol) of tripotassium phosphate in a mixture of 500 ml of toluene, 500 ml of dioxane and 400 ml of water, and the mixture is subsequently heated under reflux for 16 h. After cooling, the precipitated solid is filtered off with suction, washed three times with 50 ml of toluene, three times with 50 ml of ethanol:water (1:1, v:v), three times with 100 ml of ethanol and finally dried. Yield: 44 g (76 mmol), 62%.

d) 7-(4-Phenyl-1H-benzimidazole)-4-(9-phenylanthracen-10-yl)benz[a]-anthracene

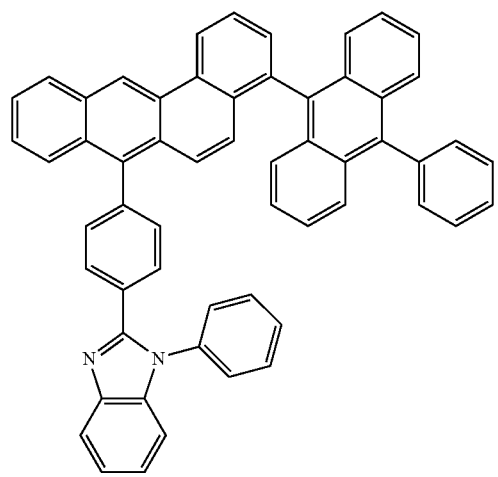 [SMILES: c1ccc(-c2c3ccccc3c(-c3cccc4c3ccc3c(-c5ccc(-c6nc7ccccc7n6-c6ccccc6)cc5)c5ccccc5cc34)c3ccccc23)cc1]

In a flask which has been thoroughly dried by heating, 20 g (34.2 mmol) of 7-(p-benzaldehyde)-4-(9-phenylanthracen-10-yl)benz[a]anthracene and 23 g (123 mmol) of N-phenyl-o-phenylenediamine are dissolved in 900 ml of DMF, 157.7 g (256 mmol) of potassium hydrogen monopersulfate are added dropwise, and the mixture is subsequently stirred for a further 1 h and then heated at 60° C. for 1 h. After cooling, the precipitated solid is filtered off with suction, washed three times with 50 ml of ethanol:water (1:1, v:v), three times with 100 ml of ethanol and finally dried. Recrystallisation five times from DMF (about 4 ml/g); sublimation (p=5×10$^{-5}$ mbar, T=320° C.). Yield: 10 g (13 mmol), 38%, purity 99.9% (HPLC).

Example 76

Production of OLEDs

OLEDs are produced by a general process as described in WO 04/058911, which is adapted in individual cases to the particular circumstances (for example layer-thickness variation in order to achieve optimum efficiency or colour).

Examples 21 to 34 below show the results for various OLEDs. Glass plates coated with structured ITO (indium tin oxide) form the substrates of the OLEDs. For improved processing, 20 nm of PEDOT (spin-coated from water; purchased from H.C. Starck, Goslar, Germany; poly(3,4-ethylenedioxy-2,5-thiophene)) are applied to the substrate. The OLEDs consist of the following layer sequence; substrate/PEDOT/hole-transport layer (HTM) 40 nm/emission layer (EML) 30 nm/electron-transport layer (ETM) 20 nm and finally a cathode. The materials apart from the PEDOT are thermally vapour-deposited in a vacuum chamber. The emission layer here always consists of a matrix material (host) and a dopant with which the host is admixed by co-evaporation. The cathode is formed by an LiF layer with a thickness of 1 nm and a 100 nm Al layer deposited thereon. Table 1 shows the chemical structures of the materials used to build up the OLEDs.

These OLEDs are characterised by standard methods; for this purpose, the electroluminescence spectra, the efficiency (measured in cd/A), the power efficiency (measured in lm/W) as a function of the luminance, calculated from current/voltage/luminance characteristic lines (IUL characteristic lines), and the lifetime are determined. The lifetime is defined as the time after which the initial luminance has dropped from 6000 cd/m$^2$ to half.

Table 2 shows the results for some OLEDs (Examples 71 to 82). The compounds of Examples 7, 8 and 11 are used as host materials according to the invention. Host H1 in accordance with the prior art is used as comparison.

Table 3 shows the results for OLEDs (Examples 83 and 84) which comprise the compound from Example 18 as electron-transport material according to the invention. As comparison, AlQ$_3$ is used as electron-transport material in accordance with the prior art.

TABLE 1

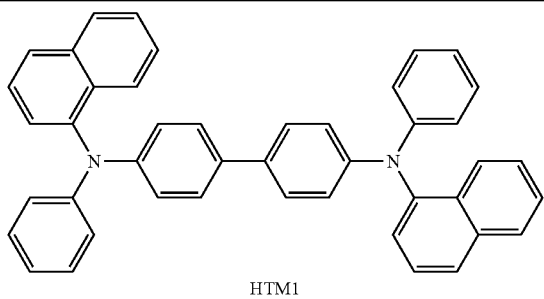

HTM1

TABLE 1-continued

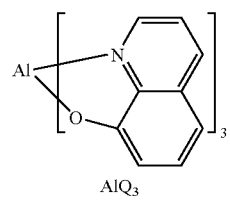

AlQ$_3$

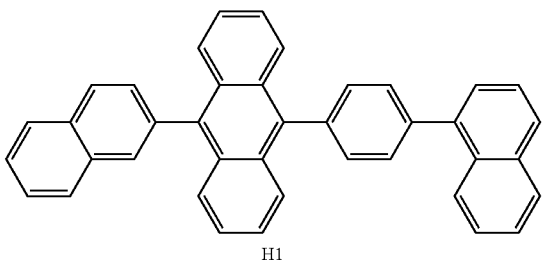

H1

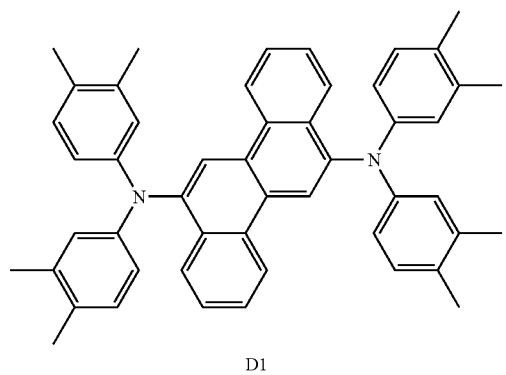

D1

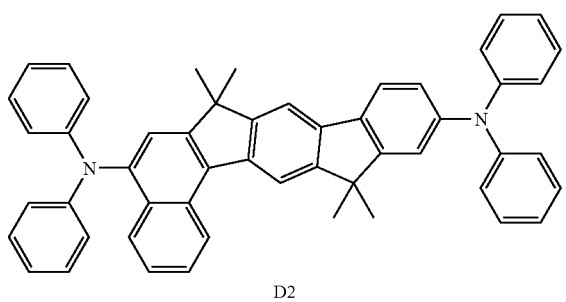

D2

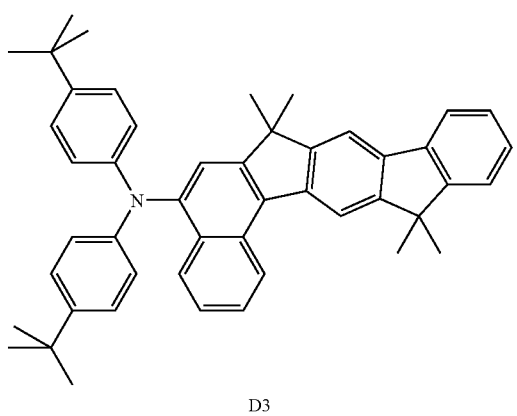

D3

TABLE 1-continued

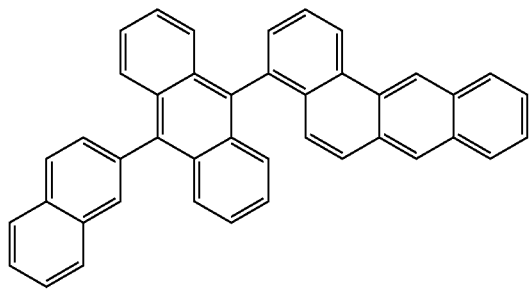 [SMILES: c1ccc2cc(-c3c4ccccc4c(-c4cccc5c4ccc4cc6ccccc6cc45)c4ccccc34)ccc2c1]

Ex. 7

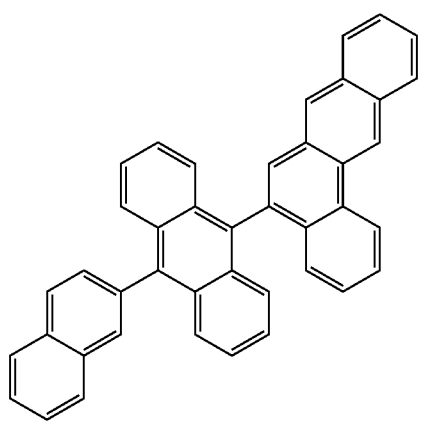 [SMILES: c1ccc2cc(-c3c4ccccc4c(-c4cc5cc6ccccc6cc5c5ccccc45)c4ccccc34)ccc2c1]

Ex. 11

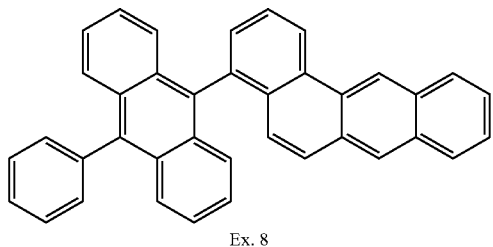

Ex. 8

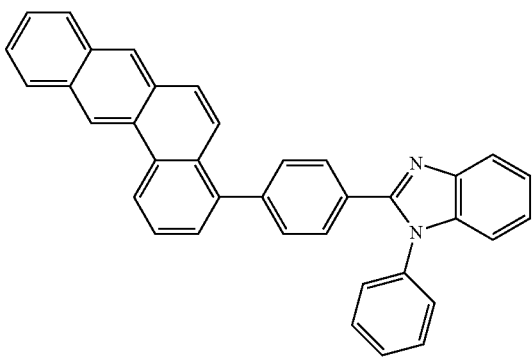 [SMILES: c1ccc(-n2c(-c3ccc(-c4cccc5c4ccc4cc6ccccc6cc45)cc3)nc3ccccc32)cc1]

Ex. 18

TABLE 2

| Example | EML | Max. efficiency (cd/A) | Voltage (V) at 1000 cd/m² | CIE | Lifetime (h) at 6000 cd/m² |
|---|---|---|---|---|---|
| 77 (comparison) | H1 + 5% of D1 | 6.8 | 5.8 | x = 0.14/ y = 0.19 | 210 |
| 78 (comparison) | H1 + 5% of D2 | 7.0 | 5.9 | x = 0.14/ y = 0.18 | 240 |
| 79 (comparison) | H1 + 5% of D3 | 6.9 | 5.7 | x = 0.14/ y = 0.21 | 280 |
| 80 | Ex. 7 + 5% of D1 | 7.1 | 5.9 | x = 0.14/ y = 0.20 | 270 |
| 81 | Ex. 7 + 5% of D2 | 7.4 | 5.6 | x = 0.14/ y = 0.17 | 280 |
| 82 | Ex. 7 + 5% of D3 | 7.3 | 6.1 | x = 0.14/ y = 0.22 | 340 |
| 83 | Ex. 11 + 5% of D1 | 7.2 | 5.9 | x = 0.14/ y = 0.19 | 270 |
| 84 | Ex. 11 + 5% of D2 | 7.5 | 5.5 | x = 0.14/ y = 0.17 | 310 |
| 85 | Ex. 11 + 5% of D3 | 7.6 | 5.9 | x = 0.14/ y = 0.21 | 400 |
| 86 | Ex. 8 + 5% of D1 | 7.0 | 5.8 | x = 0.14/ y = 0.19 | 260 |
| 87 | Ex. 8 + 5% of D2 | 7.3 | 5.4 | x = 0.14/ y = 0.17 | 300 |
| 88 | Ex. 8 + 5% of D3 | 7.1 | 5.4 | x = 0.14/ y = 0.20 | 430 |

TABLE 3

| Example | EML | ETM | Max. efficiency (cd/A) | Voltage (V) at 1000 cd/m² | CIE |
|---|---|---|---|---|---|
| 89 (comparison) | Ex. 7 + 5% of D2 | AlQ₃ | 7.4 | 5.6 | x = 0.14/ y = 0.17 |
| 90 | Ex. 7 + 5% of D2 | Ex. 18 | 7.6 | 5.2 | x = 0.14/ y = 0.17 |

As is evident from the examples given above, the organic electroluminescent devices according to the invention which comprise the compounds according to the invention as host materials have higher efficiencies and longer lifetimes than devices in accordance with the prior art. If, in addition, a material according to the invention is used instead of AlQ₃ as electron-transport material, as in Example 84 above, the efficiency of the device can be improved further and the voltage reduced.

Example 91

Production of OLEDs in Modified Layer Structure

The results for various OLEDs are presented in Examples 86 to 105 below. The OLEDs here consist of the following layer sequence: substrate/hole-injection layer (HIL1) 5 nm/hole-transport layer (HTM x) 60 nm/hole-transport layer (HTM3) 20 nm/emission layer (EML) 40 nm/electron-transport layer (ETM) 20 nm and finally a cathode. The materials are processed as indicated in Example 70. The cathode is formed by an LiF layer with a thickness of 1 nm and a 150 nm Al layer deposited thereon. Table 4 shows the chemical structures of the materials used to build up the OLEDs.

These OLEDs are characterised by standard methods; for this purpose, the electroluminescence spectra, the efficiency (measured in cd/A), the power efficiency (measured in lm/W) as a function of the luminance, calculated from current/voltage/luminance characteristic lines (IUL characteristic lines), and the lifetime are determined. The lifetime is defined as the time after which the initial luminance has dropped to half from 6000 cd/m² (in the case of blue) or 25,000 cd/m² (in the case of green).

Tables 5 to 7 show the results for some OLEDs (Examples 86 to 105). The compounds shown in Table 4 are used as dopants or host materials or electron-transport materials according to the invention. Dopant D1 and host material H1 in accordance with the prior art are used in the comparative examples.
TABLE 4
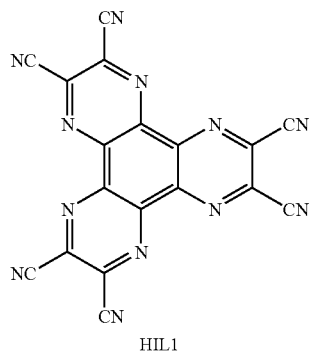
HIL1
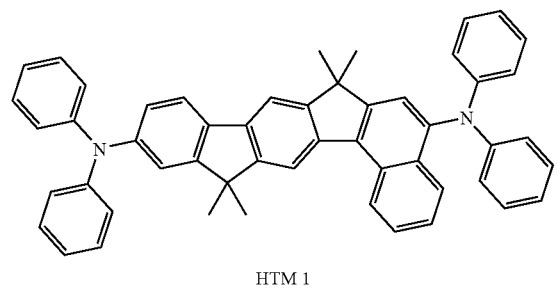
HTM 1
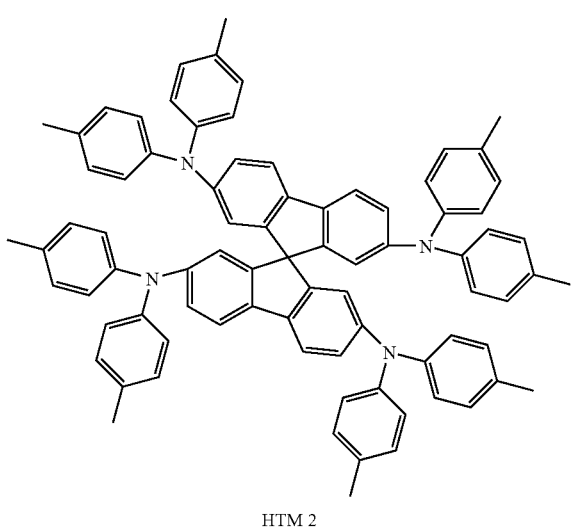
HTM 2
TABLE 4-continued
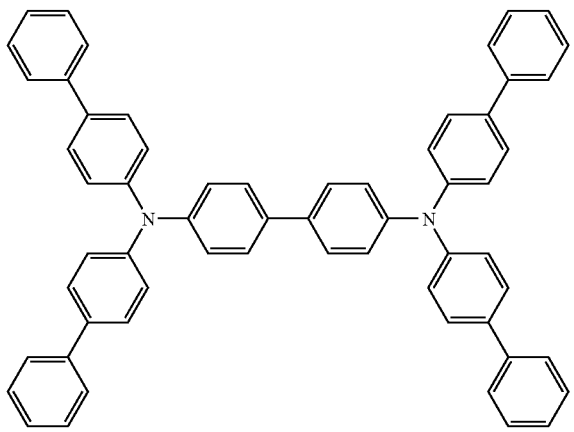 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1]
HTM 3
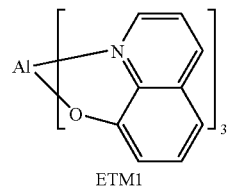
ETM1
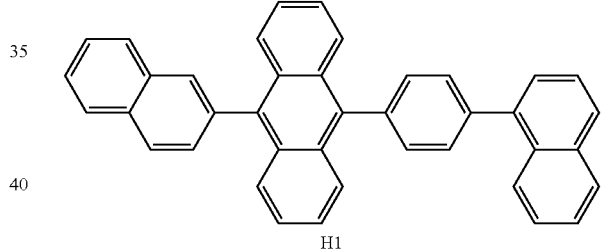
H1
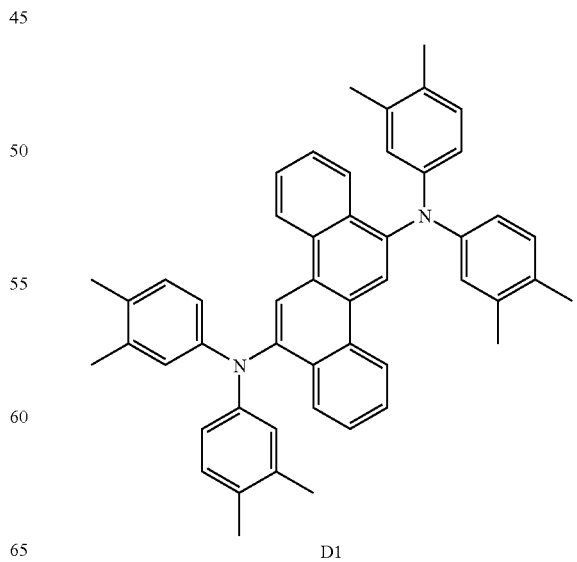
D1

TABLE 4-continued
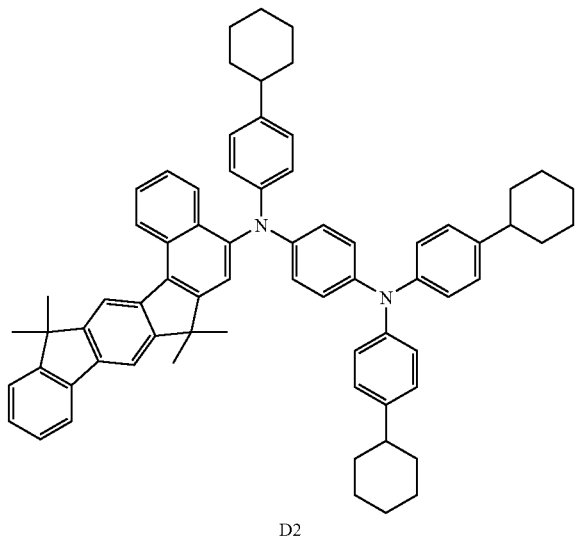
D2
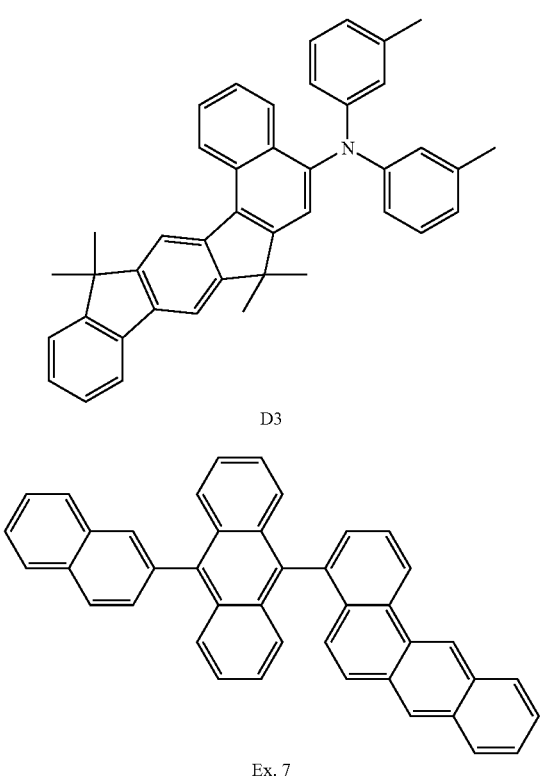
D3
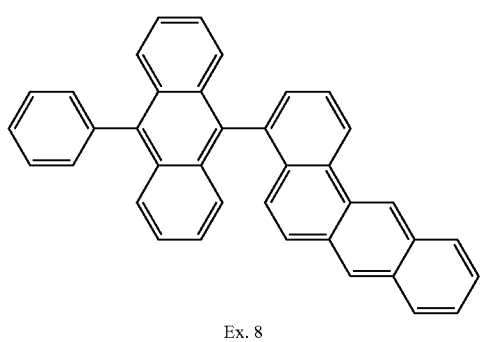
Ex. 7
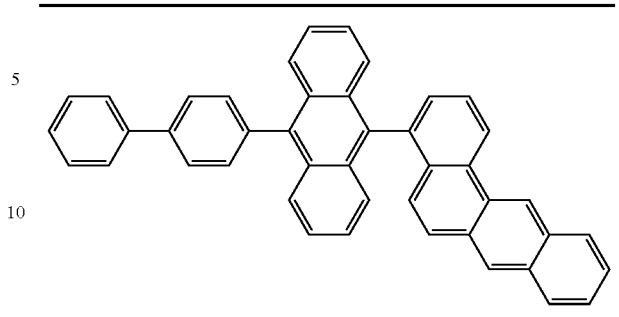
Ex. 9
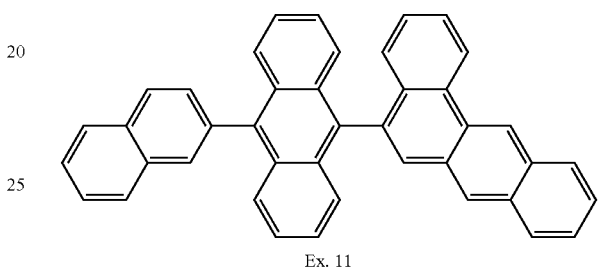
Ex. 11
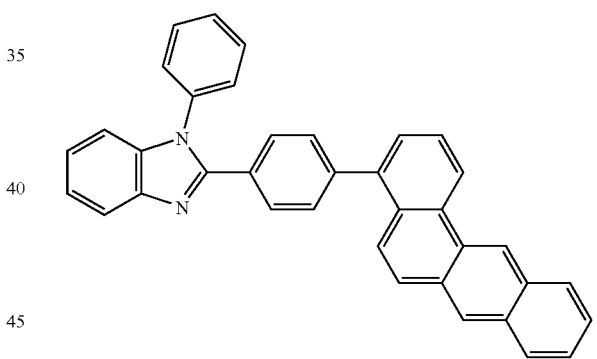
Ex. 18
TABLE 4-continued
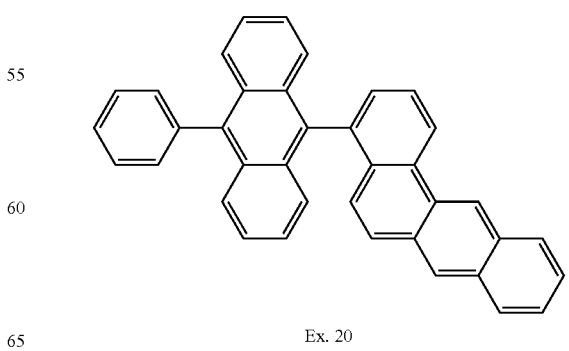
Ex. 20
Ex. 8

TABLE 4-continued

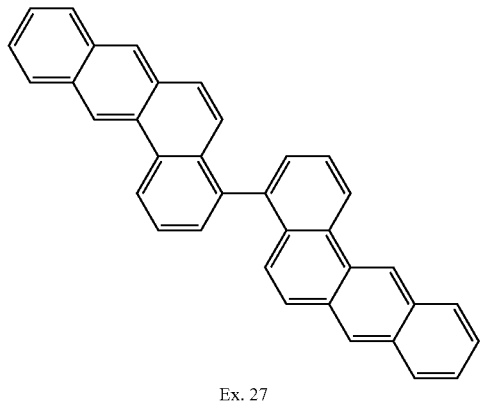

Ex. 27

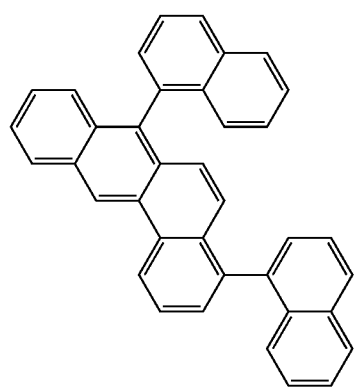 [SMILES: c1ccc2c(-c3cccc4c3ccc3c(-c5cccc6ccccc56)c5ccccc5cc34)cccc2c1]

Ex. 35

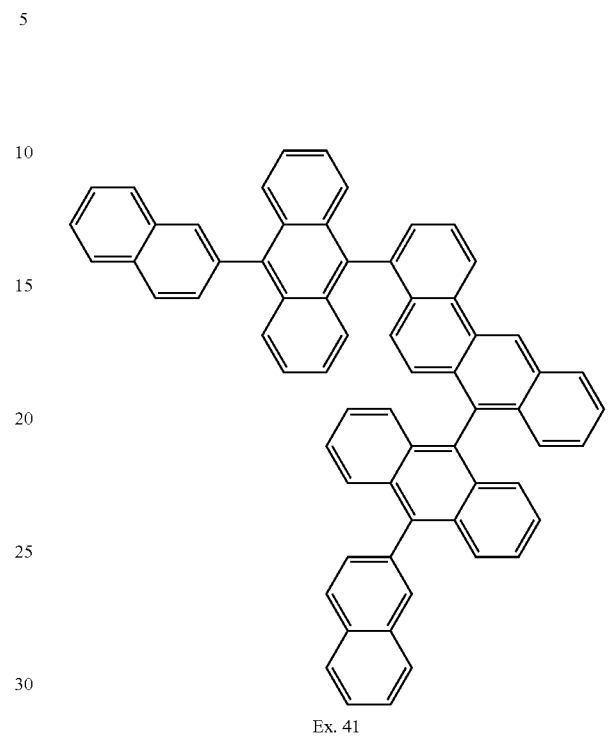

Ex. 41

TABLE 5

| Example | HTM | EML | ETM | Colour | Max. efficiency (cd/A) | Voltage (V) at 1000 cd/m$^2$ | CIE | Lifetime at 6000 cd/m$^2$ (h) |
|---|---|---|---|---|---|---|---|---|
| 92 (comparison) | HTM2 | H1 + 5% of D1 | ETM1 | blue | 6.5 | 5.5 | x = 0.14/ y = 0.18 | 450 |
| 93 | HTM2 | Ex. 7 + 5% of D1 | ETM1 | blue | 6.9 | 5.6 | x = 0.14/ y = 0.19 | 530 |
| 94 | HTM2 | Ex. 8 + 5% of D1 | ETM1 | blue | 7.0 | 5.5 | x = 0.14/ y = 0.20 | 580 |
| 95 | HTM2 | Ex. 20 + 5% of D1 | ETM1 | blue | 7.2 | 5.6 | x = 0.14/ y = 0.19 | 460 |
| 96 | HTM2 | Ex. 27 + 5% of D1 | ETM1 | blue | 6.5 | 5.3 | x = 0.14/ y = 0.18 | 430 |
| 97 | HTM2 | Ex. 8 + 5% of D1 | Ex. 18 | blue | 8.5 | 5.1 | x = 0.14/ y = 0.18 | 560 |
| 98 | HTM2 | Ex. 20 + 5% of D1 | Ex. 18 | blue | 8.7 | 5.2 | x = 0.14/ y = 0.17 | 580 |

TABLE 6

| Example | HTM | EML | ETM | Colour | Max. efficiency (cd/A) | Voltage (V) at 1000 cd/m$^2$ | CIE | Lifetime at 25000 cd/m$^2$ (h) |
|---|---|---|---|---|---|---|---|---|
| 99 (comparison) | HTM1 | H2 + 5% of D2 | ETM1 | green | 18.5 | 5.1 | x = 0.29/ y = 0.60 | 380 |
| 100 | HTM1 | H2 + 5% of D2 | Ex. 18 | green | 24.5 | 4.8 | x = 0.29/ y = 0.62 | 430 |
| 101 | HTM1 | Ex. 8 + 5% of D2 | ETM1 | green | 21.5 | 5.0 | x = 0.29/ y = 0.60 | 550 |
| 102 | HTM1 | Ex. 8 + 5% of D2 | Ex. 18 | green | 26.0 | 4.7 | x = 0.29/ y = 0.63 | 540 |
| 103 | HTM1 | Ex. 8 + 5% of D2 | ETM1 | green | 21.5 | 5.0 | x = 0.29/ y = 0.60 | 550 |

TABLE 6-continued

| Example | HTM | EML | ETM | Colour | Max. efficiency (cd/A) | Voltage (V) at 1000 cd/m² | CIE | Lifetime at 25000 cd/m² (h) |
|---|---|---|---|---|---|---|---|---|
| 104 | HTM1 | Ex. 9 + 5% of D2 | ETM1 | green | 22.5 | 4.9 | x = 0.29/ y = 0.60 | 530 |
| 105 | HTM1 | Ex. 11 + 5% of D2 | ETM1 | green | 23.0 | 4.8 | x = 0.29/ y = 0.63 | 500 |

TABLE 7

| Example | HTM | EML | ETM | Colour | Max. efficiency (cd/A) | Voltage (V) at 1000 cd/m² | CIE | Lifetime at 6000 cd/m² (h) |
|---|---|---|---|---|---|---|---|---|
| 106 (comparison) | HTM2 | H1 + 5% of D3 | ETM1 | blue | 4.5 | 5.8 | x = 0.14/ y = 0.12 | 150 |
| 107 | HTM2 | Ex. 27 + 5% of D3 | ETM1 | blue | 4.8 | 5.9 | x = 0.14/ y = 0.11 | 110 |
| 108 | HTM2 | Ex. 35 + 5% of D3 | ETM1 | blue | 4.9 | 5.8 | x = 0.14/ y = 0.10 | 130 |
| 109 | HTM2 | Ex. 8 + 5% of 3 | Ex. 18 | blue | 4.8 | 5.6 | x = 0.14/ y = 0.12 | 230 |
| 110 | HTM2 | Ex. 8 + 5% of D3 | ETM1 | blue | 4.5 | 5.8 | x = 0.14/ y = 0.12 | 250 |
| 111 | HTM2 | Ex. 35 + 5% of D3 | ETM1 | blue | 3.9 | 5.6 | x = 0.14/ y = 0.09 | 90 |

The invention claimed is:

1. An uncharged compound of the formula (1)

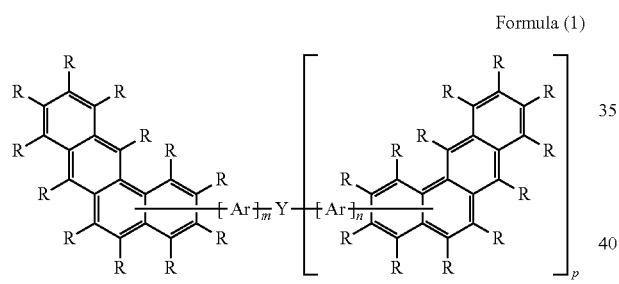

Formula (1)

wherein the group Ar or Y is bonded via one of positions 2, 3, 4, 5 or 6 of the benz[a]anthracene and correspondingly no radical R is bonded at this position and where the following applies to the symbols and indices:

Ar is on each occurrence, identically or differently, a divalent aromatic or heteroaromatic ring system having 5 to 40 aromatic ring atoms, which is optionally substituted by one or more radicals R;

Y is a selected from the formula (25)-(31)

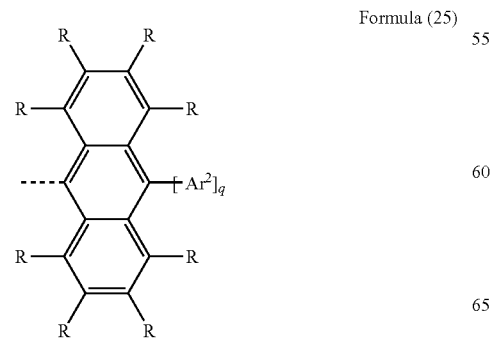

Formula (25)

-continued

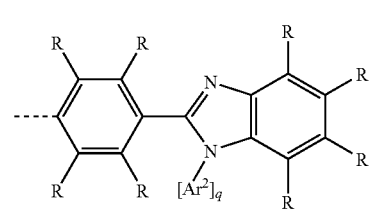

Formula (26)

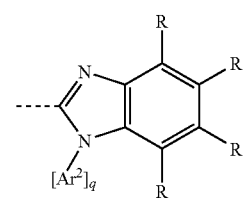

Formula (27)

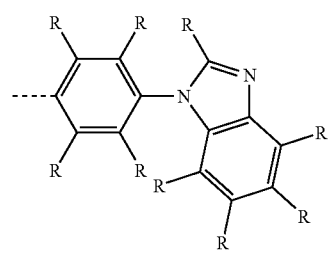

Formula (28)

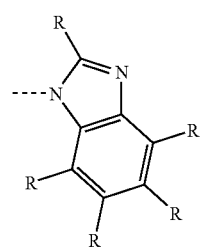

Formula (29)

Formula (30)

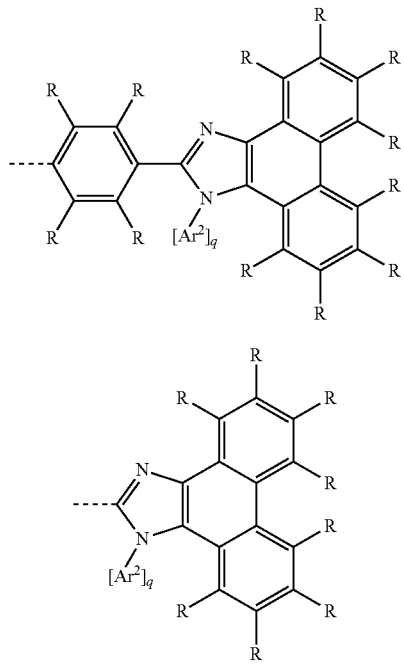

Formula (31)

wherein
R is, identically or differently on each occurrence, H, D, F, Cl, Br, I, CHO, N(Ar$^1$)$_2$, N(R$^1$)$_2$, C(=O)Ar$^1$, P(Ar$^1$)$_2$, P(=O)(Ar$^1$)$_2$, S(=O)Ar$^1$, S(=O)$_2$Ar$^1$, CR$^1$=CR$^1$Ar$^1$, CN, NO$_2$, Si(R$^1$)$_3$, B(OAr$^1$)$_2$, B(OR$^1$)$_2$, OSO$_2$R$^1$, OH, a straight-chain alkyl or thioalkoxy group having 1 to 40 C atoms or a straight-chain alkoxy group having 2 to 40 C atoms or a branched or cyclic alkyl, alkoxy or thioalkoxy group having 3 to 40 C atoms, each of which is optionally substituted by one or more radicals R$^1$, where one or more non-adjacent CH$_2$ groups is optionally replaced by R$^1$C=CR$^1$, C≡C, Si(R$^1$)$_2$, Ge(R$^1$)$_2$, Sn(R$^1$)$_2$, C=O, C=S, C=Se, C=NR$^1$, P(=O)(R$^1$), SO, SO$_2$, NR$^1$, O, S or CONR$^1$ and where one or more H atoms is optionally replaced by F, Cl, Br, I, CN or NO$_2$, or an aromatic or heteroaromatic ring system having 5 to 60 aromatic ring atoms, which is optionally substituted by one or more non-aromatic radicals R, or an aryloxy or heteroaryloxy group having 5 to 60 aromatic ring atoms, which is optionally substituted by one or more non-aromatic radicals R, or a combination of these systems; two or more adjacent substituents R here optionally form a mono- or polycyclic aliphatic ring system with one another;
wherein R in positions 7 and 12 of the benzanthracene is hydrogen;
Ar$^1$ is on each occurrence, identically or differently, an aromatic or heteroaromatic ring system having 5 to 30 aromatic ring atoms, which is optionally substituted by one or more non-aromatic radicals R; two radicals Ar$^1$ which are bonded to the same nitrogen or phosphorus atom is optionally linked to one another here by a single bond or by a bridge selected from B(R$^1$), C(R$^1$)$_2$, Si(R$^1$)$_2$, C=O, C=NR$^1$, C=C(R$^1$)$_2$, O, S, S=O, SO$_2$, N(R$^1$), P(R$^1$) and P(=O)R$^1$;
R$^1$ is on each occurrence, identically or differently, H or an aliphatic, aromatic and/or heteroaromatic hydrocarbon radical having 1 to 20 C atoms, in which, in addition, one or more H atoms is optionally replaced by F; two or more adjacent substituents R$^1$ here optionally form a mono- or polycyclic aliphatic or aromatic ring system with one another;
Ar$^2$ is an aryl or heteroaryl group having 5 to 16 aromatic ring atoms, each of which is optionally substituted by one or more radicals R$^1$, or in formula (25) a group of the formula (32) or (33)

Formula (32)

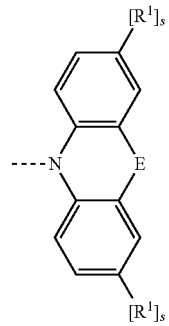

Formula (33)

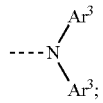

Ar$^3$ is, identically or differently on each occurrence, an aryl or heteroaryl group having 5 to 20 aromatic ring atoms or a triarylamine group having 15 to 30 aromatic ring atoms, each of which is optionally substituted by one or more radicals R$^1$;
E stands for a single bond, O, S, N(R$^1$) or C(R$^1$)$_2$, where the two radicals R$^1$ optionally forms a Spiro system through ring formation;
q is 1, 2 or 3;
s is on each occurrence, identically or differently, 0 or 1;
m is on each occurrence, identically or differently 0 or 1; and
n is 0;
p is 0.
2. The compound according to claim 1, wherein the compound of formula (1) is of the formula (2)

Formula (2)

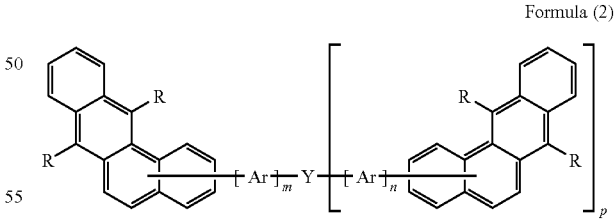

where
R is hydrogen,
the group Ar or Y is bonded via one of positions 2, 3, 4, 5 or 6 of the benz[a]anthracene and where the symbols and indices have the same meaning as described in claim 1.
3. The compound according to claim 1, wherein
Ar$^2$ is phenyl, 1-naphthyl, 2-naphthyl, 9-anthryl, chrysenyl, 1-pyrenyl, 2-pyrenyl, 2-phenanthrenyl, 3-phenanthrenyl, 9-phenanthrenyl, 2-benzimidazole, 2-fluorenyl, 2-spirobifluorenyl, fluoranthenyl, 2-benz[a]anthracenyl, 3-benz[a]-anthracenyl, 4-benz[a]anthracenyl, 5-benz[a]anthracenyl or 6-benz[a]anthracenyl, each of which is optionally substituted by one or more radicals R¹, or in formula (25) a group of the formula (32) or (33); and Ar³ is, identically or differently on each occurrence, an aryl or heteroaryl group having 6 to 14 aromatic ring atoms or a triarylamine group having 15 to 22 aromatic ring atoms, each of which may be substituted by one or more radicals R¹.

4. The compound according to claim 1, wherein the symbol Ar stands, identically or differently on each occurrence, for an arylene or heteroarylene group selected from 1,2-phenylene, 1,3-phenylene, 1,4-phenylene, 1,4-naphthylene, 9,10-anthrylene, 2,7-phenanthrenylene, 3,6-phenanthrenylene, 1,6-pyrenylene, 2,7-pyrenylene, 2,6-pyridinylene, 2,5-pyridinylene, 2,2'-biphenyl, 3,3'-biphenyl, 4,4'-biphenyl, 2,7-fluorenyl and 2,7-spirobifluorenyl.

5. The compound according to claim 1, wherein the compound is selected from formulae (3)-(7)

Formula (3)

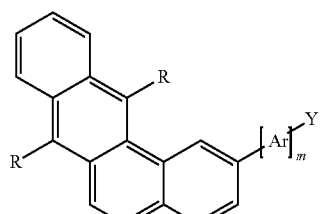

Formula (4)

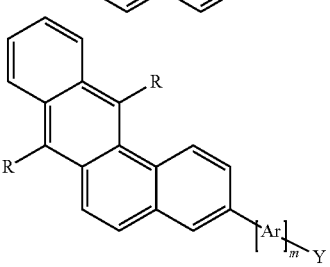

Formula (5)

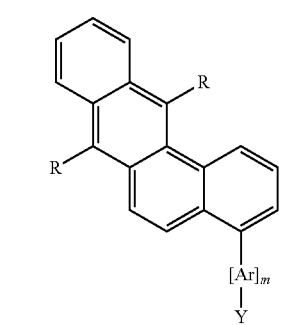

Formula (6)

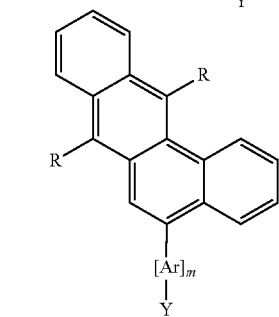

Formula (7)

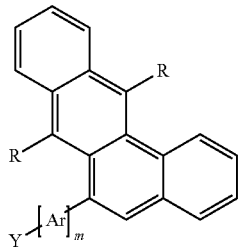

wherein the symbols and indices have the same meaning as described in claim 2, and R is H, wherein the benz[a]anthracene skeleton optionally carries deuterium instead of hydrogen.

6. The compound according to claim 1, wherein

Ar² is an aryl or heteroaryl group having 5 to 16 aromatic ring atoms, each of which is optionally substituted by one or more radicals R¹.

7. An organic electronic device which comprises the compound as claimed in claim 1.

8. The organic electronic device as claimed in claim 7, wherein the device is an organic electroluminescent device, an organic field-effect transistor (O-FET), an organic thin-film transistor (O-TFT), an organic light-emitting transistor (O-LET), an organic integrated circuit (O-IC), an organic solar cell (O-SC), an organic field-quench device (O-FQD), a light-emitting electrochemical cell (LEC), an organic laser diode (O-laser) or an organic photo receptor.

9. The organic electronic device as claimed in claim 8, wherein the device is an electroluminescent device and the compound is employed as host material for a fluorescent dopant, wherein the fluorescent dopant is a monostyrylamine, a distyrylamine, a tristyrylamine, a tetrastyrylamine, a styrylphosphine, a styryl ether or an arylamine.

10. The organic electroluminescent device according to claim 8, wherein the compound is employed as emitting material (dopant), as hole-transport material, as hole-injection material or as electron-transport material.

11. A process for the preparation of the compound according to claim 1, which comprises bonding the group Ar or Y in the 6-position of the benz[a]anthracene, by reacting an optionally substituted 2-(2'-arylacetylene)phenylnaphthalene with an electrophile.

12. A process for the preparation of the compound according to claim 1, which comprises substituting a benz[a]anthracene by a reactive leaving group and coupling to a functionalised aromatic compound or to a mono- or disubstituted amine.

13. The process according to claim 12, wherein the reactive leaving group is chlorine, bromine, iodine, triflate, tosylate, boronic acid or boronic acid ester and the coupling is by a Suzuki coupling with palladium catalysis or by a palladium-catalysed coupling by the Hartwig-Buchwald method.

14. A compound of the formula (34)

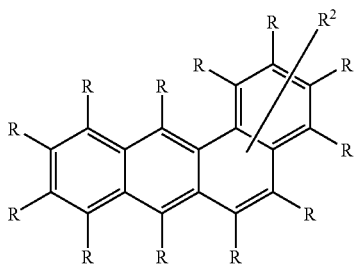

Formula (34)

wherein

R is, identically or differently on each occurrence, H, D, F, Cl, Br, I, CHO, N(Ar$^1$)$_2$, N(R$^1$)$_2$, C(=O)Ar$^1$, P(Ar$^1$)$_2$, P(=O)(Ar$^1$)$_2$, S(=O)Ar$^1$, S(=O)$_2$Ar$^1$, CR$^1$=CR$^1$Ar$^1$, CN, NO$_2$, Si(R$^1$)$_3$, B(OAr$^1$)$_2$, B(OR$^1$)$_2$, OSO$_2$R$^1$, OH, a straight-chain alkyl or thioalkoxy group having 1 to 40 C atoms or a straight-chain alkoxy group having 2 to 40 C atoms or a branched or cyclic alkyl, alkoxy or thioalkoxy group having 3 to 40 C atoms, each of which is optionally substituted by one or more radicals R$^1$, where one or more non-adjacent CH$_2$ groups is optionally replaced by R$^1$C=CR$^1$, C≡C, Si(R$^1$)$_2$, Ge(R$^1$)$_2$, Sn(R$^1$)$_2$, C=O, C=S, C=Se, C=NR$^1$, P(=O)(R$^1$), SO, SO$_2$, NR$^1$, O, S or CONR$^1$ and where one or more H atoms is optionally replaced by F, Cl, Br, I, CN or NO$_2$, or an aromatic or heteroaromatic ring system having 5 to 60 aromatic ring atoms, which is optionally substituted by one or more non-aromatic radicals R, or an aryloxy or heteroaryloxy group having 5 to 60 aromatic ring atoms, which is optionally substituted by one or more non-aromatic radicals R, or a combination of these systems; two or more adjacent substituents R here optionally form a mono- or polycyclic aliphatic ring system with one another;

Ar$^1$ is on each occurrence, identically or differently, an aromatic or heteroaromatic ring system having 5 to 30 aromatic ring atoms, which is optionally substituted by one or more non-aromatic radicals R; two radicals Ar$^1$ which are bonded to the same nitrogen or phosphorus atom is optionally linked to one another here by a single bond or by a bridge selected from B(R$^1$), C(R$^1$)$_2$, Si(R$^1$)$_2$, CO=O, C=NR$^1$, C=C(R$^1$)$_2$, O, S, S=O, SO$_2$, N(R$^1$), P(R$^1$) and P(=O)R$^1$;

R$^1$ is on each occurrence, identically or differently, H or an aliphatic, aromatic and/or heteroaromatic hydrocarbon radical having 1 to 20 C atoms, in which, in addition, one or more H atoms is optionally replaced by F; two or more adjacent substituents R$^1$ here optionally form a mono- or polycyclic aliphatic or aromatic ring system with one another;

and R$^2$ is bonded in position 2, 3, 4, 5 or 6 of the benz[a]anthracene and correspondingly no group R is bonded at this position, and furthermore:

R$^2$ stands for B(OR$^1$)$_2$ or B(OAr$^1$)$_2$.

15. An oligomer, polymer or dendrimer which comprises one or more compounds according to claim 1, where one or more radicals R or Ar or Y represent bonds from the compound according to claim 1 to the polymer, oligomer or dendrimer.

16. An electronic device which comprises the oligomer, dendrimer or polymer according to claim 15.

17. The electronic device according to claim 16 wherein the electronic device is an organic electroluminescent device.

* * * * *